United States Patent
Kaminaga et al.

[11] Patent Number: 5,904,418
[45] Date of Patent: May 18, 1999

[54] AUTOMATIC KNEADING APPARATUS AND FALLEN MATERIAL RETURNING APPARATUS

[75] Inventors: Kenzo Kaminaga; Masaaki Suzuki; Takashi Kimura; Keisuke Kato; Yuji Nogami; Yoshihisa Hirakuri; Takashi Chino; Takao Kawamura; Atsushi Tsutsumi, all of Tokyo; Masaru Takeuchi; Hideo Yoshikoshi, both of Ibaraki-ken, all of Japan

[73] Assignees: Nikkiso Company Limited; Shin-Etsu Chemical Company Limited, both of Tokyo, Japan

[21] Appl. No.: 08/377,746

[22] Filed: Jan. 25, 1995

Related U.S. Application Data

[63] Continuation-in-part of application No. 08/325,373, Dec. 7, 1994, abandoned.

[30] Foreign Application Priority Data

| Feb. 25, 1993 | [JP] | Japan | P5-37118 |
| Feb. 25, 1993 | [JP] | Japan | P5-37119 |
| Feb. 25, 1993 | [JP] | Japan | P5-37120 |
| Feb. 18, 1994 | [JP] | Japan | 6-021279 |
| Feb. 18, 1994 | [JP] | Japan | 6-021280 |

[51] Int. Cl.$^6$ ..................................................... B01F 7/12
[52] U.S. Cl. .................................. 366/71; 366/72; 366/73; 425/201; 425/217; 425/230
[58] Field of Search ................................. 366/69, 71–74; 425/215, 217, 201, 230, 367; 100/72, 174, 168, 173, 327

[56] References Cited

U.S. PATENT DOCUMENTS

| 2,062,215 | 11/1936 | Dubus | 425/215 X |
| 2,624,068 | 1/1953 | Dobry | 425/230 X |
| 2,728,103 | 12/1955 | Benedict et al. | 425/230 |
| 4,111,626 | 9/1978 | Funakoshi et al. | 425/367 X |
| 4,889,429 | 12/1989 | Heinzmann et al. | 366/73 X |
| 5,198,243 | 3/1993 | Shimizu et al. | 425/230 |
| 5,295,803 | 3/1994 | Ogawa et al. | 425/367 X |
| 5,336,076 | 8/1994 | Waldherr et al. | 425/367 X |
| 5,456,871 | 10/1995 | Harada et al. | 425/367 X |

FOREIGN PATENT DOCUMENTS

| 621525 | 10/1935 | Germany | 425/230 |
| 49-26703 | 7/1974 | Japan | 425/215 |
| 52-10962 | 1/1977 | Japan | 425/201 |
| 52-10963 | 1/1977 | Japan | 425/201 |
| 60-36116 | 2/1985 | Japan | 100/161 |
| 60-73814 | 4/1985 | Japan | 425/201 |

*Primary Examiner*—Charles E. Cooley
*Attorney, Agent, or Firm*—Browdy and Neimark

[57] ABSTRACT

A sheet-testing apparatus including kneading rolls, a frame feeder, sheet applicator, foreign material detector, a frame with a light transparent window and a cutter for cutting a sheet. A sheet-testing sample-making apparatus has a cluster of kneading rolls, frame feeder, and sheet applicator. A sheet thickness detection apparatus outputs an electric signal to a memory. A kneading apparatus has a pair of heating rolls separated by a gap. The directions and speeds of rotations of the rolls are adjustable. A sensor detects the gap and a bank sensor detects the condition of a bank in the gap. The distance between the rolls, their temperatures, rotations, and speeds are automatically controlled. A pair of blades peel a sheet from the sheet-winding roll. Material dropped through the gap between the heating rolls is returned to a point above the gap. A cutting device has a length of wire sprung onto a rolled sheet to sever the sheet. A heating roll cleaning device brings cleaning rolls into sliding engagement with the heating rolls. A heating roll cleaning device feeds an elongated cloth-like cleaning member for cleaning heating rolls.

4 Claims, 32 Drawing Sheets

FIG. 39
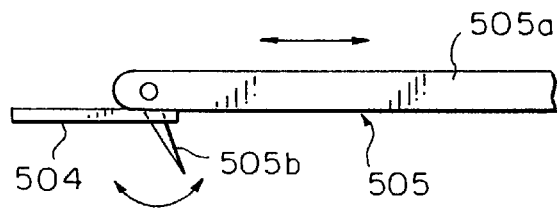
FIG. 40
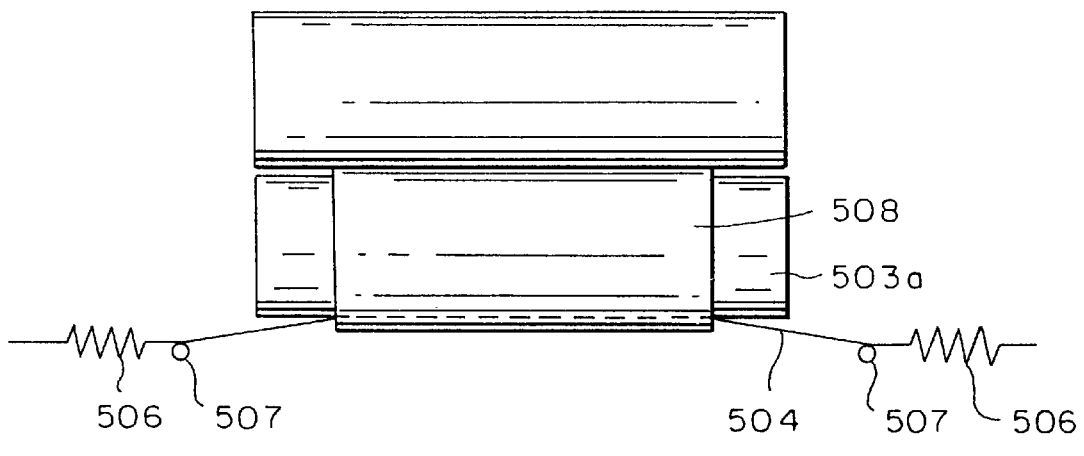
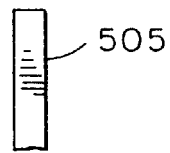

AUTOMATIC KNEADING APPARATUS AND FALLEN MATERIAL RETURNING APPARATUS

CROSS-REFERENCE TO RELATED APPLICATION

This is Continuation-In-Part of application Ser. No. 08/325,373, filed Dec. 7, 1994, now abandoned which is hereby incorporated herein by reference.

FIELD OF THE INVENTION

The present invention relates to a sheet testing apparatus including a frame, a sheet testing sample making apparatus, and a frame feeding apparatus. More particularly, the present invention is concerned with a fully automatic sheet testing apparatus that optically detects a sheet automatically cut from rolled sheet material that is produced by kneading, wound on a roll, removed from the roll and applied to and held by a frame. The apparatus determines whether or not the tested sheet contains a foreign matter with a frame of a simple structure. The apparatus includes a sheet testing sample making apparatus which automatically makes a sheet testing sample, and a frame feeding apparatus which automatically feeds a frame, required for the production of a sheet testing sample, toward a roll.

The present invention also relates to an automatic sheet thickness detection apparatus and, more particularly, to an automatic sheet thickness detection apparatus that automatically detects the thickness of a sheet wound on a kneading roll heated to a high temperature.

The present further invention relates to an automatic kneading apparatus and, more particularly, to an automatic kneading apparatus to knead powdered material fed to a point above a gap between a pair of heating rolls and to wind a rolled sheet on a heating roll.

The present invention relates to a kneading apparatus and, more particularly, to a kneading apparatus which is operative to carry out kneading by means of a sheet winding roll and a counter roll and to adjust the width of a sheet wound on the sheet winding roll to thereby efficiently produce a kneaded sheet of a predetermined width.

The present invention relates to a kneading apparatus and a fallen material returning apparatus used with the kneading apparatus. More particularly, the invention is concerned with a kneading apparatus and a fallen material returning apparatus which is operative to return, to a point above a gap between a pair of heating rolls, a powdered material or a melted or partly melted fallen material dropped through the gap between the heating rolls during a kneading operation, to thereby prevent the consumption of the raw material in the case where the fallen material is powdered material in the initial stage of the kneading operation and, in the case where the fallen material is a melted or partly melted sheet-like material, to automatically wind such a sheet material on a heating roll without any manual operation being needed.

The present invention relates to a rolled sheet cutting apparatus and, more particularly, to a rolled sheet cutting apparatus of a simple structure which accurately cuts a rolled sheet wound on a sheet winding roll of a kneading roll apparatus.

The present invention relates to a heating roll cleaning apparatus and, more particularly, to a heating roll cleaning apparatus which is operative to clean the surfaces of heating rolls used to knead synthetic resin and produce a sheet.

BACKGROUND OF THE INVENTION

In general, a producer of synthetic resin or the like is required to check, as part of quality control, whether or not gel or fish eye is generated in the synthetic resin produced.

The manufacturer who obtains synthetic resin from the producer to manufacture various kinds of products is also required to check the resin thus obtained to see if there is fish eye or gel in the resin and to consider to what extent fish eye or gel is generated in the case where there is a predetermined condition of the work. This is because, if such fish eye or the like exists, an attempt to print on the surface of a product made with the synthetic resin will result in a defective product due to poor adhesion of ink to the surface.

A test roll apparatus is an apparatus for testing whether or not fish eye or gel is generated in synthetic resin.

The test roll apparatus has a pair of heating rolls disposed in parallel relationship. The pair of heating rolls is arranged such that the gap therebetween is freely adjustable and the direction and speed of the rotation are also freely adjustable. In addition, the temperature of the heating rolls may be variously set. The gap between the heating rolls may initially be set at, for example, 0.2 mm.

The heating rolls are used to make a resin testing sheet as follows:

A predetermined amount of a certain powdered resin is fed to a gap between the heating rolls. Since a small gap is formed between the pair of heating rolls, a very small part of the powdered resin would fall through the gap, but major part of the resin of the powdered resin forms a mound-like deposit rising from the gap.

The heating rolls are heated to a predetermined temperature and rotated at either the same rotational speed or at different rotational speeds to impart shearing force and thermal energy to the powdered resin on the heating rolls. As a result of the shearing, the powder of the resin itself also generates heat.

By the heat generated in the resin powder itself through shearing and also the heat imparted by the heating rolls, the resin is partly melted and extruded in the form of a sheet through the gap between the heating rolls, which is slightly widened. The leading end of the extruded sheet is advanced by the rotation of the heating rolls and the sheet is wound on one heating roll. As a result, melted or partly melted resin is wound on one of the pair of heating rolls. In addition, melted resin is deposited into the gap between the pair of heating rolls.

In this state, kneading is continued for a predetermined time period. With time, the size of the resin mound is decreased with a resultant increase in the width of the sheet wound on the heating roll. When the mound of melted resin is completely kneaded, the kneading by the heating rolls is stopped and the sheet of resin is separated from the heating roll.

In order to separate the sheet of resin, the sheet wound on the stopped heating roll is cut or severed parallel to the axis of the heating roll. Then the cut end of the sheet of resin is then pulled, while the heating roll is rotated, to separate the sheet of resin from the heating roll.

The sheet of resin thus produced by the test roll apparatus is used to look for gel or fish eye in the sheet of resin as follows:

The sheet of resin obtained as described above is tensioned by suitable means and light is shined on the back side of the sheet while the front side of the sheet is observed visually. If fish eyes or the like are present in the sheet of resin, they are seen as white lightened spots. Fish eyes or the like is measured by counting the white lightened spots and/or measuring the spot diameters with a slide caliper or rule.

The prior art test roll apparatus described above has required several manual operations, including those to cut a sheet of resin wound on a heating roll, mount the sheet of resin separated from the heating roll, and detect fish eyes or the like in the sheet of resin.

When manually cutting a sheet of resin wound on the heating roll, the operator has been required to work beside the heating roll which was not fully cooled. Thus, there was a danger that the operator would have been burned. In addition, manual sheet cutting has resulted in sheets of irregular shapes, with the disadvantageous result that sheets of resin having uniform dimensions could not be obtained.

Also, it has been troublesome to manually put the separated sheets of resin on a frame and frequently it has been impossible to put the sheets on the frame under uniform tension.

Moreover, when the sheet thus mounted was held to light and inspected to detect fish eyes, count their number, and measure their sizes, there has been the possibility of damage to the operator's eyes. Another big problem has been human error, with differences depending on the particular observers included in the measured data.

In the prior art, the thickness of a resin sheet wound on a heating and kneading roll was measured by first cutting a part of the wound resin sheet with a suitable device such as for example a spatula and then measuring the resin fragment thus obtained with a dial gauge.

However, the operation of manually cutting a part of the resin sheet from the heating and kneading roll during its rotation involved the danger that an operator be burned, have fingers pinched between the heating and kneading rolls, and so on. In addition, manual measurements with a dial gauge caused differences in the measured values of the thicknesses of sheets as between different operators who measured with the gauge.

In the conventional kneading apparatus, which includes the conventional test roll described above, the pair of heating rolls are arranged such that a gap between them is set to a predetermined dimension and the gap is then widened as the thickness of a sheet wound on a heating roll is increased. The heating rolls are rotated during a kneading operation in such directions that a bank or mound of the material is caught and pinched between the rolls.

The conventional kneading apparatus was run by an operator according to his own experience and perception. In the conventional kneading apparatus, therefore, the kneading operations cannot be said to have always been carried out in the best way. Different operators followed different kneading steps, with the result that the degree of kneading was not always constant.

With the conventional kneading apparatus, moreover, the width of a rolled sheet wound about one of the heating rolls (the one hereinafter called the "sheet winding roll") is increased with the kneading time. In order to assure a predetermined width of the rolled sheet, therefore, a pair of width limiting plates are provided on the peripheral surface of the sheet-winding roll. Each plate has a bottom end with a curved surface having the same radius as the sheet-winding roll.

The width limiting plates are only effective to limit the width of rolled sheets and in no way contribute to the kneading operation.

On the other hand, in the conventional kneading apparatus, a rolled sheet enters a bank formed in a gap formed between the sheet winding roll and the other heating roll (hereinafter called the "counter roll") disposed opposite to the sheet winding roll to achieve a kneading operation. In order to render the kneading operation efficient, controls are provided for adjustment of the relative speeds of the counter roll and the sheet winding roll, maintaining the temperatures of these rolls, and so on.

There are problems with the conventional kneading operation described above. The conventional kneading apparatus is not yet satisfactory in that kneading takes a long time and the kneading operation and widthwise offsetting of a rolled sheet are carried out independently. Thus, the kneading operation as a whole is troublesome.

In the production of a kneaded sheet with the conventional kneading apparatus, the heating rolls are heated to predetermined temperatures and rotated in the initial stage of the process of producing the kneaded sheet to apply heat and shearing force to a mound above a gap between the heating rolls, so that mound particles of powdered material are fused and united together and become partly melted. The material thus becomes appropriately fluid and begins to hang from the heating rolls through the gap therebetween.

When the part of the material hanging down through the gap between the heating rolls grows to a suitable length, the operator uses an appropriate tool such as knife, spatula, or the like to guide the part of the material hanging down through the gap between the heating rolls onto and along the peripheral surface of one of the heating rolls until the forward end portion of the hanging part of the material is guided to a point above the gap between the heating rolls.

The conventional kneading apparatus, which inevitably requires such manual operation, involves a danger that the operator pinches his hand or his hands in between the heating rolls.

Moreover, in such a conventional kneading apparatus, even though the gap between the heating rolls is set to a small dimension in the initial stage of kneading operation, the powdered material leaks and falls through the gap between the heating rolls resulting in a substantial loss of the powdered material.

In order to eliminate this loss of powdered material, one might think to dispose a receiving member under the pair of heating rolls to catch the material falling through the gap between the heating rolls and to return the fallen material to a point above the gap between the heating rolls. However, it is quite troublesome to each time dispose such a receiving member under the gap between the heating rolls, take out and lift the receiving member to the gap between the heating rolls, and drop the powdered material from the receiving member toward the gap between the heating rolls. If such operation is to be manually carried out by an operator, there is a danger that the heating rolls may burn the operator.

When the kneading by the heating rolls has proceeded to a certain extent, the end of the sheet of the material, which hangs down from the heating rolls, must be wound on a heating roll. In the past, this operation was also carried out manually. Therefore, there was a great danger that, when the sheet end was wound, the heating rolls would burn the operator.

In the case where the conventional kneading apparatus is used to manufacture a sheet of vinyl chloride resin, silicone resin, or the like, or a sheet of an elastic high molecular compound such as rubber or EPDM, the sheet must be removed from the sheet winding roll. Several methods are conceivable for removing such sheet from the sheet winding roll.

One method might be to first cut or sever the sheet of the material wound on the sheet winding roll by means of a scraper having a thin knife edge. However, it has been found that, when a sheet on the sheet winding roll is cut by the scraper, the cut end of the sheet becomes waved and fail to provide a removed sheet having a linear cut end. It has also been found that, when the scraper is urged against a sheet on the sheet winding roll in order to cut the sheet, the surface of the sheet winding roll is damaged by the edge of the scraper. Accordingly, measures for preventing the sheet winding roll from being damaged are required.

Another method is to cut open a sheet on the sheet winding roll parallel to its axis with a sharp knife.

However, it has been found that, with the method of using the knife, it is difficult to squarely and accurately cut open a sheet along the roll axis. In addition, there is a possibility that the knife damages the surface of the sheet winding roll, as in the case of the scraper. Thus, some measures are demanded for avoiding the damage.

In the past, moreover, because the scraper or the knife was manipulated by an operator to cut a sheet, there was a danger that the operator could be burned by the heat of a very high temperature heating rolls.

With the conventional kneading apparatus, it was required to clean the surfaces of the heating rolls after a sheet produced by kneading was removed from the heating rolls. The operator used a cloth to wipe the surfaces of the heating rolls to remove deposits of material such as synthetic resin or elastic high molecular weight compounds adhered to the heating rolls. However, there was a problem that the removing operation took a long time and lowered the operation rate of the kneading apparatus. In addition, because both heating rolls become substantially hot, there was a danger that the manual operation could involve burns.

The present invention was made in consideration of these circumstances.

Therefore, the present invention has as one object to provide a sheet testing apparatus which automatically detects or measures fish eyes, gel, and so on that are present in a sheet of resin, without requiring any manual operation.

It is another object of the present invention to provide a frame which can be easily charged with a sheet of resin obtained by severing a rolled sheet of resin wound on a kneading roll that also acts as a heating roll and which is easily used with a means for detecting foreign matter to test the resin sheet.

It is a further object of the present invention to provide a sheet testing sample-making apparatus which easily and automatically makes a sheet testing sample which is charged with a sheet of resin and which can be easily mounted on a foreign matter detecting means for detecting foreign matter in sheets of resin.

It is a further object of the present invention to provide a frame feeding apparatus to feed a frame to kneading rolls so that the frame can be suitably used for making the sheet testing sample and so that a rolled sheet wound on the kneading roll can be automatically mounted on and applied to the frame.

It is a still further object of the present invention to provide an automatic sheet thickness detecting apparatus which is operative to automatically, safely and accurately measure, without requiring any manual operation, a sheet formed by heating and kneading rolls.

It is a still further object of the present invention to provide an automatic kneading apparatus which kneads a material uniformly.

It is a still further object of the present invention to provide a kneading apparatus which kneads material effi-cient and which simultaneously performs both kneading and widthwise adjustment of a rolled sheet.

It is a still further object of the present invention to provide a kneading apparatus which kneads efficiently.

It is a still further object of the present invention to provide a kneading apparatus and a fallen material returning apparatus used therewith which effectively returns, to a point above a gap between heating rolls, material fallen through the gap between the heating rolls.

It is a still further object of the present invention to provide a kneading apparatus and a fallen material returning apparatus used therewith which are operative to automatically return, to a point above a gap between heating rolls, powdered material dropped through the gap between the heating rolls in an initial stage of kneading operation to thereby reduce loss of the powdered material.

It is a still further object of the present invention to provide a kneading apparatus and a fallen material returning apparatus used therewith which are operative to automatically return, to a point above a gap between heating rolls, powdered material dropped through the gap between the heating rolls in an initial stage of kneading operations to thereby reduce loss of the powdered material and which also automatically wind on a heating roll an end of a sheet of the material hanging down through the gap between the heating rolls in a later stage of the kneading operation.

It is a still further object of the present invention to provide a roll cutting apparatus which is operative to sever, without any manual operation, a rolled sheet wound on a sheet winding roll to form an accurately linear cut end and which does not damage the surface of the sheet winding roll.

It is a still further object of the present invention to provide a heating roll cleaning apparatus which is operative to automatically clean the surfaces of a pair of heating rolls to improve the rate of operation and assure safety.

SUMMARY OF THE INVENTION

To solve the problems discussed above, the present invention relates to a sheet testing apparatus comprising kneading rolls; frame feeding means for feeding a frame with a light transparent window toward a sheet winding roll of said kneading rolls, said sheet winding roll having a surface adapted to be covered with a sheet of a predetermined width; sheet application means for urging the frame, which has been fed by said frame feeding means toward said sheet winding roll, against said sheet winding roll to cut the sheet covering said sheet winding roll and for transferring and applying the thus cut sheet to said frame; and foreign material detecting means for detecting foreign material contained in the sheet applied to said frame.

The sheet testing apparatus may be structured such that said sheet application means comprises a pinch roll for urging the frame, which has been fed to said sheet winding roll, against said sheet winding roll.

The sheet testing apparatus may be structured such that said frame feeding means is so designed as to feed the frame into a gap between said sheet winding roll and a counter roll disposed in opposed relationship therewith, and such that said sheet application means comprises said counter roll.

The sheet testing apparatus may be structured such that said foreign material detecting means comprises light irradiation means for irradiating one side of the sheet-applied frame with light, image pick-up means for picking up an image of the frame irradiated by the light irradiation means, and judgement means for judging a foreign material in said sheet based on a video signal from said image pick-up means.

The sheet testing apparatus may further include a memory for being written in/read from identification data obtained by reading an identification mark provided on said frame, and data obtained by the judgement by said judgement means of a foreign material in said sheet.

The frame according to the present invention comprises a plate material of a size large enough to be applied with a sheet cut from a sheet covering a sheet winding roll, a light transparent window formed in a central portion of said plate material, and a linear cutter provided on said plate material adjacent an end thereof.

The frame according to the present invention comprises a plate material of a size large enough to be applied with a sheet cut from a sheet covering a sheet winding roll, a light transparent window formed in a central potion of said plate material, and a tapered or rounded portion formed on an edge of said window.

The frame of the structure pointed out above is structured such that said plate material has a surface to which a sheet is to be applied, and said surface is coated with adhesive.

The sheet testing sample-making apparatus according to the present invention comprises kneading rolls, frame feeding means for feeding a frame with a light transparent window toward a sheet-winding roll of said kneading rolls, said sheet winding roll having a surface adapted to be covered with a sheet of a predetermined width; and sheet application means for urging the frame, which has been fed by said frame feeding means toward said sheet winding roll, against said sheet winding roll to cut the sheet covering said sheet winding roll and for transferring and applying the thus cut sheet to said frame.

A first frame feeding apparatus according to the present invention comprises a housing for accommodating a plurality of frames, frame selection means for selecting one of the frames in said housing, and guiding means for guiding the thus selected frame toward a sheet winding roll.

A second frame feeding apparatus according to the present invention comprises a housing for accommodating a plurality of frames and including a front portion having formed therein an upper opening and a lower opening, a pressing member for urging the frames in said housing against a back surface of said front portion, a lower end pressing member for pressing a lower end of a frame in said housing to urge the frames, excepting a frame to be withdrawn, inwardly of said back surface of said front portion into said housing, the forwardmost frame in said housing being adjacent the back of said front portion and having a surface exposed to said upper opening, pick up means for lifting said forwardmost frame while said surface of said forwardmost frame is attracted by a first attracting member, and guide means for guiding the thus lifted forwardmost frame toward a sheet winding roll adapted to be covered with a sheet of a predetermined width while a lower end of the forwardmost frame is attracted by a second attracting member.

The invention pointed out above will be described in more detail.

The sheet testing apparatus of the present invention comprises kneading rolls which in turn comprise at least one pair of heating rolls. A material such as resin is kneaded by the kneading rolls. A sheet of material such as resin, for example, is wound in a roll shape around one kneading roll. The kneading roll around which the sheet is wound in roll shape is referred to as sheet winding roll. Another roll which is disposed in opposed relationship to the sheet winding roll with an axis extending parallel to that of the sheet winding roll is referred to as a counter roll.

A frame having a light transparent window is fed toward the sheet winding roll. The frame comprises a plate material of a size large enough to be applied with a sheet cut from a sheet covering the sheet winding roll and the light transparent window formed in a central portion of the plate material. The frame may be structured such that a sheet or film of resin cut away from a sheet or film wound on the sheet winding roll can be applied to the frame so as to extend across the light transparent window. In order that the sheet or film of resin wound on the sheet winding roll may be smoothly cut away therefrom, the frame may preferably be provided with a linear cutting edge disposed adjacent the forward end of the plate material. In the case where the frame is passed through a gap between the sheet winding roll and the counter roll, the cutting edge may be unnecessary on the surface of the frame and, instead, an edge portion of an opening which forms the light transparent window may be of a tapered or rounded shape so that the sheet or film of resin wound on the sheet-winding roll is cut and the cut sheet or film of resin is transferred to the frame such that the sheet or film is applied to the frame without slack.

When the forward end of the frame is moved by the frame feeding apparatus to a point adjacent the sheet on the sheet winding roll, a sheet applying means urges the frame against the sheet wound on the sheet winding roll. Because the cutting edge is provided on the surface of the forward end portion of the frame, the sheet is cut or severed when the frame is urged against the sheet on the sheet winding roll. Because the frame feeding apparatus continues to move the frame forwardly after the sheet has been cut or severed, the thus cut or severed sheet is peeled away from the surface of the sheet winding roll and transferred and applied to the surface of the frame as the frame is moved past the sheet-winding roll. The sheet transferred and applied to the frame is inspected by a foreign matter detecting apparatus so that a foreign matter such as fish eye in the sheet is detected.

The operation of the sheet testing apparatus of the present invention is as described above. In the case where the sheet applying means discussed above comprises a pinch roll operative to urge against the sheet winding roll a frame fed to the sheet-winding roll, the pinch roll urges the frame against the sheet on the sheet-winding roll so that the cutting edge of the frame cuts or severs the sheet.

In the case where the frame feeding means is so structured as to feed the frame into a gap defined between the sheet winding roll and the counter roll disposed in opposed relationship thereto and the sheet applying means comprises the counter roll, the frame fed by the frame feeding means into the gap between the counter roll and the sheet-winding roll is pinched between the counter roll and the sheet-winding roll so that the cutting edge of the frame cuts or severs the sheet on the sheet-winding roll, whereby, when the frame is moved through the gap between the counter roll and the sheet-winding roll, the thus cut sheet on the sheet-winding roll is transferred therefrom and applied to the frame.

An adhesive is needed on the surface of the frame as the case may be. In case that a sheet is a thin film made by polyvinylchloride resin, there is no need of the adhesive on the surface of the frame and such a thin film can adhere on the surface of the frame. In case the sheet is thick and it is adhered on the surface of the frame without adhesive, it may be peeled out from the surface of the frame. Therefore, there needs adhesive on the surface of the frame in such a case. The adhesive may be selected from the known ones. It is preferable to use a solution-type adhesive such as a chloroprene rubber, a nitrocellulose, a vinyl acetate resin and a nitrile and an emulsion-type adhesive such as a chloroprene rubber, a vinyl acetate resin and an acrylic resin.

In the case where the foreign material detecting means comprises light irradiation means for irradiating one side of the sheet-applied frame with light, image pick-up means for picking up an image of the frame irradiated by the light irradiation means, and judgement means for judging a foreign material in the sheet based on a video signal from the image pick-up means, one side of the sheet applied to the frame is irradiated with light. The image pick-up means is disposed on the other side of the sheet and picks up the image of the thus light-irradiated sheet. The judgement means detects foreign matters, counts the number thereof, or measures the sizes thereof on the basis of the video signal output from, for example, the image pick-up means.

The sheet-testing sample making apparatus according to the present invention is structured such that the frame feeding means feeds a frame, having a cutting edge on a surface adjacent a forward end and a light transparent window, toward a sheet-winding roll of the kneading rolls, the sheet-winding roll having a surface adapted to be covered with a sheet of a predetermined width, and the sheet application means urges the thus fed frame against the sheet-winding roll to cut the sheet covering the sheet winding roll and transfers and applies the thus cut sheet to the frame, whereby a sheet-testing sample comprising the frame and the thus cut sheet applied thereto is made.

The first and second frame feeding apparatus are preferred examples of the frame feeding means.

According to the first frame feeding apparatus of the structure pointed out above, the frame selection means selects one of the frames in the housing and the thus selected frame is guided by the guiding means toward the sheet winding roll.

In the second frame feeding apparatus of the structure pointed out above, a plurality of frames accommodated in the housing is initially urged by the pressing member against a back surface of the front portion of the housing. Then, when it is required to feed a frame toward the sheet winding roll, the first attracting member attracts that surface of the forwardmost frame adjacent the back of the front portion which is exposed to said upper opening. Then, the frame is released from the urging force applied by the urging member. The pick up means lifts the forwardmost one of the plurality of frames accommodated in the housing while the forwardmost frame is attracted by the first attracting member. When the forwardmost frame is so lifted, said pressing member and the lower end pressing member cooperate to pinch therebetween the lower portions of the plurality of frames excepting the forwardmost one and move these frames inwardly away from the back surface of the front portion of the housing. This releases the forwardmost frame from the urging force applied by the pressing member. Then, the forwardmost frame is released from the attraction by the first attracting member and the lower portion of the forwardmost frame is attracted by the second attracting member. With the lower portion of the forwardmost frame kept attracted by the second attracting member, the guide means withdraws the frame out of the housing and guides the frame toward the sheet winding roll. When the forwardmost frame is completely withdrawn from the housing, the pressing member and the lower end pressing member are moved toward the front portion of the housing while the plurality of frames excepting the forwardmost one are pinched by the pressing member and the lower end pressing member. Thus, the second frame now becomes to be the forwardmost frame and the above-described steps will be repeated.

The automatic sheet thickness detection apparatus according to the present invention comprises at least two measuring elements spaced one from the other by a predetermined distance and disposed on a base movable toward and away from a kneading roll, a displacement detection section for outputting an electric signal representative of a displacement of the measuring elements, a memory for storing data output by said displacement detection means when said measuring elements are in contact with said kneading roll when no sheet is wound thereon, and an operating and processing section for calculating a thickness of a sheet based on data output by said displacement detection means when said measuring elements are in contact with said kneading roll when said sheet is wound thereon and the data read out of said memory.

In the automatic sheet thickness detection apparatus of the present invention, the measuring elements are positioned in contact with a kneading roll before the kneading rolls form a sheet. The data output from the displacement detection section at this time is stored in the memory. The data indicates "0" point. When a sheet has been formed by the kneading rolls, the measuring elements are again positioned in contact with the surface of the rolled sheet. The difference between the data output from the displacement detection section at this time and the date already stored in the memory is calculated by the operating and processing section to obtain the thickness of the sheet.

As such, the thickness of a sheet on a kneading roll is automatically measured without any manual operation needed. Thus, the possibility of an accident is now completely eliminated and, in addition, the sheet thickness can be accurately obtained by calculation.

The automatic kneading apparatus according to the present invention comprises a pair of heating rolls arranged such that a dimension of a gap therebetween is adjustable and that the directions and speeds of rotations of said rolls are variable, a temperature sensor operative to detect the temperatures of said heating rolls and output measured data representative of the thus measured temperatures, a rotation number sensor for detecting the numbers of rotations of respective heating rolls and outputting detection data representative of the thus detected numbers of rotation, a position sensor for detecting the gap between the pair of heating rolls, a bank sensor for detecting the condition of a bank existing in said gap between said heating rolls, and control means for receiving data from the various sensors to automatically control the distance between the pair of heating rolls and the temperatures, directions of rotations and speeds of rotations of the pair of heating rolls so that the formation and vanishing of the bank are repeated by a predetermined number.

For the heating rolls, the kneading rolls heated by known methods can be used. As an example, the kneading rolls having high frequency induction coils built-in and connected with power supply are preferably used.

According to the automatic kneading apparatus of the present invention, the gap defined between the pair of heating rolls is adjusted to be of the minimum dimension and a predetermined amount of powdered material is fed to a point above the gap between the heating rolls. The heating rolls are heated to predetermined temperatures and rotated in the normal or reversed directions so that the heating rolls apply heat and shearing force to the powdered material. The temperatures of the heating rolls are monitored by the temperature sensor. The condition of a bank formed in the gap between the heating rolls is monitored by the bank sensor. The bank sensor may be a sensor that is operative to detect the presence of a bank which is being formed or has been formed between the heating rolls, such as sensor comprising a light emitting component and photo detector. The word "bank" used herein is intended to mean an amount of resin accumulated or stored in the gap or valley defined between the pair of rolls. The amount of resin may be in either a melted condition or powdery condition.

As the powdered material is gradually kneaded by the heat of the heating rolls and the shearing force caused by the rotations of the heating rolls, the gap between the heating rolls, the heating temperature, and the directions and speeds of rotations of the heating rolls are further adjusted by the control means and the kneading of the material by the heating rolls is continued.

When a bank of melted material is formed as a result of the kneading, the control means determines the optimum gap between the heating rolls, the heating temperature and the directions and speeds of the rotations and the kneading is continued in the optimum condition.

After the kneading has been continued for a determined time period with the bank formed, the control means widens the gap between the heating rolls and adjusts the heating temperature and the speeds and directions of rotations of the heating rolls to be the optimum until the bank between the heating rolls melts and a sheet of the kneaded material is wound around one of the heating rolls.

After the sheet of the material has been wound on one of the heating rolls to form a rolled sheet and the bank between the heating rolls has vanished, the control means is again operated to narrow the gap between the heating rolls and adjust the heating temperature of the heating rolls and the speeds and directions of rotations thereof so that a bank is formed in the gap between the heating rolls. With the bank so formed, the material is kneaded by the heating rolls for a determined time period.

After the kneading has been continued for a determined time period with the bank formed, the control means widens the gap between the heating rolls and adjusts the heating temperature and the speeds and directions of rotations of the heating rolls to be the optimum ones to assure that the bank between the heating rolls melts and a sheet of the kneaded material is wound on one of the heating rolls.

The formation and vanishing of the bank as described are repeated a desired number of times, with the result that a sufficiently kneaded sheet is obtained.

The first kneading apparatus of the present invention comprises a counter roll, a sheet winding roll disposed in opposed relationship with said counter roll and a pair of blades each disposed on said sheet winding roll and having a scooping surface operative to peel a rolled sheet from said sheet winding roll, a rear guide surface operative to guide, by the rotation of said sheet winding roll, the thus peeled sheet backwardly of the direction of the movement of said rolled sheet for thereby folding the peeled sheet backwardly and a lateral guide surface operative to guide, by the rotation of said sheet winding roll, the peeled sheet toward a center line of said rolled sheet for thereby folding the sheet toward said sheet center line. The term "rolled sheet" used herein is intended to mean a sheet of resin wound on the sheet winding roll.

The second kneading apparatus of the present invention comprises a counter roll, a sheet-winding roll disposed in opposed relationship with said counter roll and a single blade disposed on said sheet winding-roll and having a scooping surface operative to peel a rolled sheet from said sheet-winding roll, a rear guide surface operative to guide, by the rotation of said sheet-winding roll, the thus peeled sheet backwardly of the direction of the movement of said rolled sheet for thereby folding the peeled sheet backwardly and lateral guide surfaces operative to guide, by the rotation of said sheet-winding roll, the peeled sheet toward the ends of said rolled sheet for thereby folding the sheet toward said ends of said sheet.

Any of the first and second kneading apparatuses pointed out above may be structured such that the pair of blades or single blade is disposed on the sheet winding roll for movement axially thereof by a driver.

According to the first kneading apparatus, the scooping surface is operative to peel away from the surface of the sheet-winding roll the rolled sheet wound thereon. The thus peeled rolled sheet is folded by the rear guide surface in the direction opposite to the direction of rotation of the rolled sheet and also folded by the lateral guide surface toward the center of the rolled sheet. The rolled sheet peeled away from the surface of the sheet winding roll is fed into a bank positioned above the gap between the counter roll and the sheet-winding roll while the sheet is folded in the direction opposite to the direction of rotation of the rolled sheet and folded toward the center of the sheet, whereby the kneading is further carried out by the rotations of the counter roll and the sheet-winding roll.

The pair of blades are also operative to limit the width.

According to the second kneading apparatus, the scooping surface is operative to peel away from the surface of the sheet winding roll the rolled sheet wound thereon. The thus peeled rolled sheet is folded by the rear guide surface in the direction opposite to the direction of rotation of the rolled sheet and also folded by the lateral guide surfaces outwardly of the rolled sheet, i.e., toward the ends of the rolled sheet. The rolled sheet peeled away from the surface of the sheet winding roll is fed into a bank positioned above the gap between the counter roll and the sheet winding roll while the sheet is folded in the direction opposite to the direction of rotation of the rolled sheet and folded toward the ends of the sheet, whereby the kneading is further carried out by the rotations of the counter roll and the sheet-winding roll.

Each of the pair of blades of the first kneading apparatus and the single blade of the second kneading apparatus is movable by a driver axially of the sheet winding roll to assure optimum kneading.

The third kneading apparatus of the present invention comprises a pair of heating rolls, and fallen material returning means for returning material, dropped through a gap between said heating rolls, to a point above said gap.

The fallen material returning means according to the present invention comprises a pair of supporting bases each having a first support so disposed as to face tops of a pair of heating rolls, a second support so disposed as to face bottoms of said heating rolls, and a third support interconnecting said first and second supports, said supporting bases being disposed in opposed relationship; a group of driven rolls comprising at least a first driven roll rotatably disposed between the pair of first supports, a second driven roll rotatably disposed between the pair of said second supports and a movably supported third driven roll; an endless belt extending around the rolls of said group of driven rolls; and base driving means operative to move said supporting bases forwardly and backwardly to bring said endless belt into and out of contact with a heating roll.

The fallen material returning means may further include a first blade for scraping a surface of said endless belt engaged with said first driven roll and a second blade disposed adjacent said second driven roll to scrape one of said heating rolls which is not engaged by said endless belt.

The third kneading apparatus is structured such that the fallen material returning means receives powdered material dropped through the gap between the heating rolls, returns the thus received material to a point above the gap between the heating rolls and, in addition, drops transferred powdered material into the gap between the heating rolls. Therefore, any powdered material which would fall through the gap between the heating rolls in the initial stage of kneading can be used in the kneading for economy.

When the kneading by means of the heating rolls has proceeded to a certain extent, the kneaded material hangs down in a sheet-like configuration extending downwardly through the gap between the heating rolls. The fallen material returning means receives the thus hanging sheet-like kneaded material and guides the same to the gap between the heating rolls. Accordingly, the sheet-like portion of the melted or partially melted powdered material can be easily and reliably wound on a heating roll without any manual operation needed.

The fallen material returning device of the present invention has an initial position in which, by the base driving means, the endless belt is moved away from the heating rolls and the supporting bases are retracted to predetermined positions. When a kneading operation by means of the heating rolls starts, the base driving means is operated to drive the base toward the heating rolls to bring the endless belt into engagement with a heating roll. At this time, the third driven roll has a take-up to cause the endless belt to extend around the peripheral surface of the heating roll over a predetermined length thereof as well as to subject the endless belt to a predetermined tension.

When the heating rolls are rotated, the endless belt extending around the first driven roll, second driven roll and third driven roll is rotated following the rotation of the heating roll engaged with the endless belt. Because the second driven roll is disposed below and in facing relationship to the heating rolls, the endless belt receives fallen material dropped between the heating rolls. The rotation of the endless belt carries the fallen material on the endless belt to the peripheral surface of a heating roll. Because the first driven roll is disposed above and in facing relationship to the top surfaces of the heating rolls, a part of the fallen material carried to the peripheral surface of the heating roll is removed away from the endless belt, adhered to the peripheral surface of the heating roll and transported to the gap between the heating rolls, while the rest of the fallen material is adhered to the conveyance surface of the endless belt, transported to the first driven roll and dropped at a point adjacent thereto toward the heating rolls.

In this case, if a first blade is provided for scraping the surface of the endless belt adjacent the first driven roll, the fallen material can be reliably returned from the conveyance surface of the endless belt adjacent the first driven belt to the heating rolls. If a second blade is provided adjacent the second driven roll for scraping the surface of the counter heating roll disposed in opposed relationship to the heating roll which is engaged with the endless belt, the deposit on the counter heating roll can be scraped by the second blade and returned onto the endless belt.

The rolled sheet cutting device according to the present invention comprises a length of wire disposed adjacent a sheet winding roll in parallel relationship to an axis of a sheet winding roll and tensioned by a biasing member, said sheet winding roll constituting a kneading roll and surrounded by a rolled sheet wound thereon, and engagement means for forcibly moving said wire away from said sheet winding roll and then releasing said wire.

The rolled sheet cutting device may include biasing members connected to the opposite ends of the length of wire.

The rolled sheet cutting device may be structured such that the wire is formed into an endless shape through a pair of driven rolls movable by biasing members and a driving roll.

In the rolled sheet cutting device according to the present invention, the length of wire is engaged by the engagement means and pulled thereby away from the sheet winding roll. Thereafter, the wire is released from the engagement means. Therefore, the wire is sprung by the spring force of the biasing members toward the sheet wound on the sheet-winding roll and strikes and instantaneously cuts or severs the sheet. Because the length of wire is disposed adjacent the sheet-winding roll so as to extend parallel to the axis thereof, the wire cuts the sheet such that the cut end of the sheet is parallel to the axis of the sheet-winding roll. The sheet separated from the sheet-winding roll has an accurately linear cut end.

In this rolled sheet cutting device, the wire cuts the sheet in such a manner as to strike the sheet. In other words, the sheet is not cut by a sharp cutting knife. Thus, the surface of the sheet-winding roll is prevented from being damaged.

When the frame does not have the cutting edge on its surface and, instead, has an opening, which forms the light transparent window, with an edge portion of a tapered or rounded shape, transferring the sheet or film wound on the sheet winding roll to the frame after cutting the sheet or film with this rolled sheet cutting device results in a good sample. In this case, it is important to set the cut position of the sheet or film to the edge portion of the opening. This setting will be explained later.

The first heating roll cleaning device according to the present invention comprises a cleaning roll for cleaning surfaces of a pair of heating rolls, cleaning roll moving means for bringing said cleaning roll into sliding engagement with each of the surfaces of said heating rolls, and a dirt removing member for removing dirt from the surface of said cleaning roll.

The second heating roll cleaning device of the present invention comprises a cleaning roll for cleaning surfaces of a pair of heating rolls, cleaning roll moving means for selectively bringing said cleaning roll into sliding engagement with either one of the surfaces of said heating rolls, and a dirt removing member for removing dirt from the surface of said cleaning roll.

The operation of the first and second heating roll cleaning device of the structures pointed out above is described hereinunder.

A material such as a synthetic resin is fed into a gap between a pair of heating rolls which are driven in such a manner as to catch the material, whereby a kneaded product is made. The motions of such heating rolls cause melted or partly melted synthetic resin to adhere to both heating rolls to form residual deposits thereon after the kneading.

The cleaning roll for cleaning the surfaces of the heating rolls is moved by the cleaning roll moving means into sliding engagement with the heating rolls. It is preferred that the rotations of respective rolls be so adjusted as to be in the opposite directions, respectively. In the case where the respective rolls are rotated in the same directions, the rolls may be driven at different speeds.

Accordingly, the cleaning roll is rotated while wiping away from the heating rolls the synthetic resin adhered to the surfaces of the rolls. As a result of the operation of the cleaning roll, the surface of the cleaning roll becomes dirty by the synthetic resin wiped away from the heating rolls. The dirt removing member removes the dirt from the surface of the cleaning roll.

Accordingly, the surfaces of both heating rolls can be cleaned reliably and automatically, so that the rate of operation of the heating rolls can be improved.

The manual cleaning operation, which was needed in the past, becomes unnecessary; this assures safety.

The cleaning roll moving means comprises a support for the cleaning roll and a hydraulic cylinder or air pressure cylinder for driving the cleaning roll.

The cleaning roll may preferably be cylindrical and made of a material the same as the synthetic resin which adheres to the heating rolls. The surface of the cleaning roll may preferably be of a lesser hardness (i.e. softer) than those of the heating rolls.

The dirt removing member comprises a scraper operative to scrape dirt on the surface of the cleaning roll.

It is preferred that both heating rolls and the cleaning roll be driven by independent drive sources so that they are rotated at different speeds and in different directions.

In the second heating roll cleaning device, the roll moving means moves the cleaning roll into sliding engagement with the surface of either one of the heating rolls.

Accordingly, the cleaning roll is rotated while scraping the synthetic resin adhered to the surfaces of the heating rolls. As a result of the operation of the cleaning roll, the surface of the cleaning roll becomes dirty by the synthetic resin wiped away from the heating rolls. The dirt removing member removes the dirt from the surface of the cleaning roll.

Accordingly, the surfaces of both heating rolls can be cleaned reliably and automatically, so that the rate of operation of the heating rolls can be improved.

The third heating roll cleaning device according to the present invention comprises cleaning member feeding means for feeding and transporting an elongated cloth-like cleaning member for cleaning surfaces of a pair of heating rolls, and cleaning member contacting means for bringing into sliding engagement with said pair of heating rolls a part of said cleaning member in its way in a path of feed by said cleaning member feeding means.

The fourth heating roll cleaning device of the present invention comprises cleaning member feeding means for feeding and transporting an elongated cloth-like cleaning member for cleaning surfaces of a pair of heating rolls, and cleaning member contacting means for selectively bringing into sliding engagement with either one of said pair of heating rolls a part of said cleaning member in the feed path of said cleaning member feeding means.

The operations of the third and fourth heating roll cleaning devices is described hereinunder.

A material such as a synthetic resin is fed into a gap between a pair of heating rolls which are driven in such a manner as to catch the material, whereby a kneaded product is made. The motions of such heating rolls cause melted or partly melted synthetic resin to adhere to both heating rolls to form residual deposits thereon after the kneading.

The cleaning member contacting means brings into sliding engagement with the heating rolls a part of the cleaning member in the feed path of the cleaning member feeding means. Thus, the cleaning member wipes away from the surfaces of the heating rolls the synthetic resin adhered to the rolls while the cleaning member is being fed and transported. The feeding of the cleaning member is continued to assure that the surfaces of both heating rolls are always in sliding engagement with fresh parts of the cleaning member, whereby the surfaces of the heating rolls can be reliably and automatically cleaned to improve the rate of operation of the heating rolls.

The manual cleaning operation, which was needed in the past, is made unnecessary to assure safety.

The cleaning member feeding means may comprise feeding and take-up rolls for feeding the cleaning member and for taking up the cleaning member, or a feeding cassette accommodating the cleaning member in folded state and a take-up roll. Alternatively, the cleaning member may be transported in an endless manner.

The cleaning member may comprise a fabric material (woven, knitted, or non-woven material) impregnated with an organic solvent, a leather sheet, or synthetic leather.

The cleaning member contacting means may comprise a combination of a feeding roll in contact with the cleaning member and an engaging/disengaging mechanism section for moving the feeding roll under said two rolls into and out of contact therewith, for example, a support for the feeding roll and a hydraulic cylinder for driving the support.

In the fourth heating roll cleaning means, the cleaning member contacting means brings into sliding engagement with either one of the pair of heating rolls a part of the cleaning member in a feed path of the cleaning member feeding means. In this case, the cleaning member may be alternately brought into engagement with the pair of heating rolls in such a manner that one of the heating rolls may be kept in sliding engagement with the cleaning member for a fixed period of time, and, thereafter, the other heating roll may be in sliding engagement with the cleaning member. Alternatively, only the heating roll that becomes heavily dirty may be engaged by the cleaning member so as to simplify the cleaning operation.

BRIEF DESCRIPTION OF THE DRAWING FIGURES

FIG. 39 is a schematic illustration of the engagement means shown in FIG. 38;

FIG. 40 is a schematic illustration of the operation of the rolled sheet cutting apparatus shown in FIG. 37;

DETAILED DESCRIPTION OF THE PREFERRED EMBODIMENT

A preferred embodiment of the present invention is described.

Figure 1:
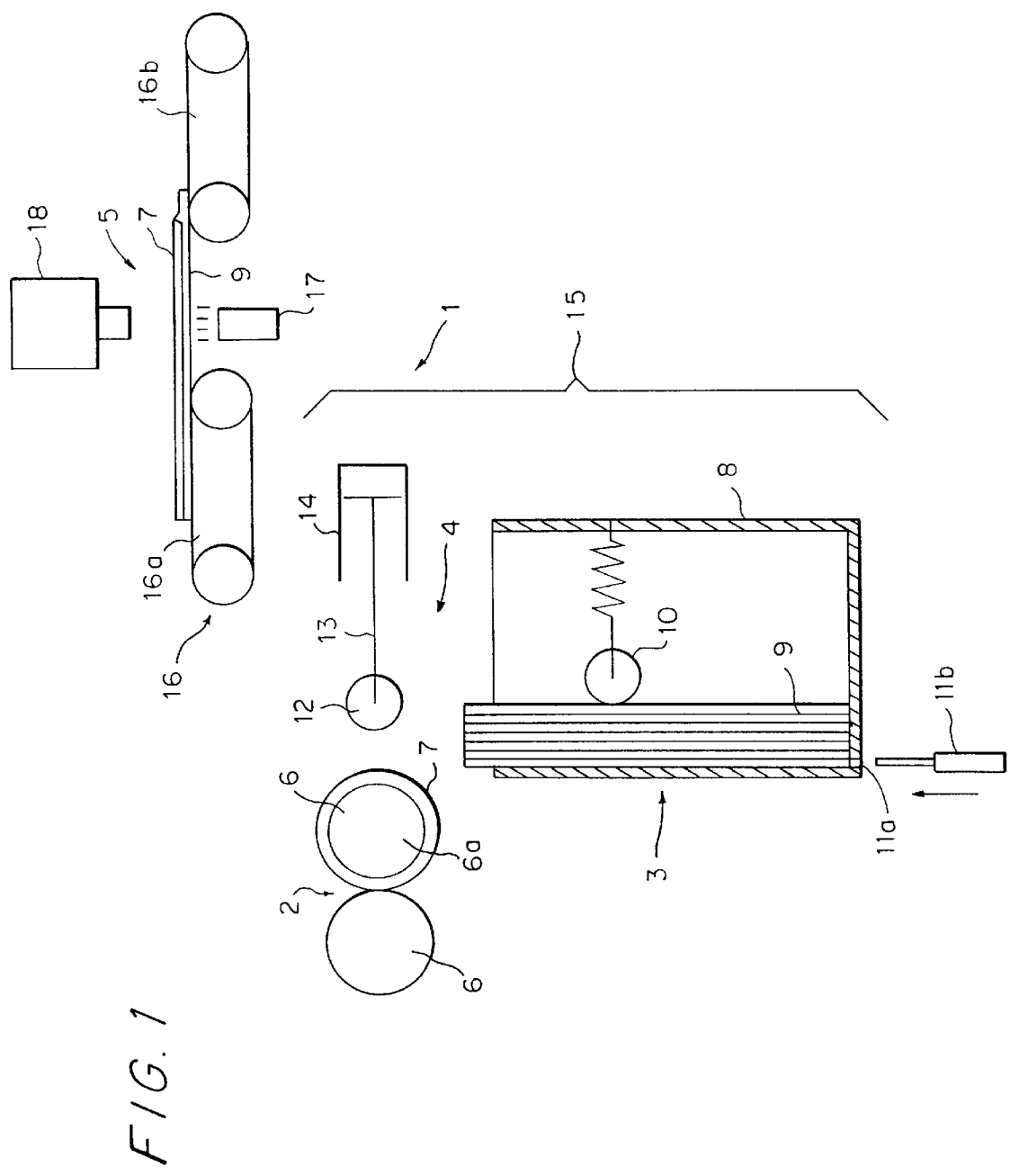
FIG. 1 is a schematic illustration of a sheet testing apparatus which incorporates a sheet testing sample-making apparatus and utilizes a frame.

FIG. 1 is a schematic illustration of a sheet testing apparatus of the invention, which incorporates a sheet testing sample-making apparatus and which utilizes a frame.

As shown in FIG. 1, the sheet testing apparatus 1 comprises a kneading roll 2, a frame-feeding means 3, a sheet applying means 4 and a foreign matter detecting means 5.

The kneading rolls 2 comprises at least one pair of heating rolls 6 disposed in parallel relationship. One of the heating rolls 6 is intended to wind up a sheet and thus is also termed a "sheet-winding roll" 6a. The pair of heating rolls 6 are so arranged that the gap therebetween can be adjusted to be wide or narrow and the temperatures of the heating rolls can be freely set by suitable heating means. In addition, the rotational speeds of the heating rolls 6 can be freely set by a driver such as a motor.

The kneading rolls 2 can be used to carry out mixing of, for example, a resin such as a thermoplastic resin or an elastic material such as rubber. In a kneading operation, a predetermined amount of powdered raw material is fed into the space between the pair of heating rolls 6 so as to be subjected to treatments such as compression, heating and shearing, with a result that a sheet 7 of fully mixed material is formed in a roll-like shape on the peripheral surface of the sheet winding roll 6a.

On the other hand, the frame-feeding means 3 has a pushing pin 11b operative to feed, toward the peripheral surface of the sheet winding roll 6a, a plurality of frames 9 stored in a frame storing box 8 disposed below the mixing rolls 2. The frame storing box 6 is provided with a pushing roll 10 operative to urge a plurality of frames 9 against an inner wall of the frame storing box 8 so that the pushing roll 10 sets a predetermined frame in a position ready to be fed out of the box. The bottom surface of the frame storing box 8 is formed therein with a hole 11a through which the pushing pin 11b is movable. The pushing pin 11b moves through the hole 11a to upwardly push the surface of the bottom end of a predetermined frame 9 to force the same out of the frame storing box 8.

Figure 2:
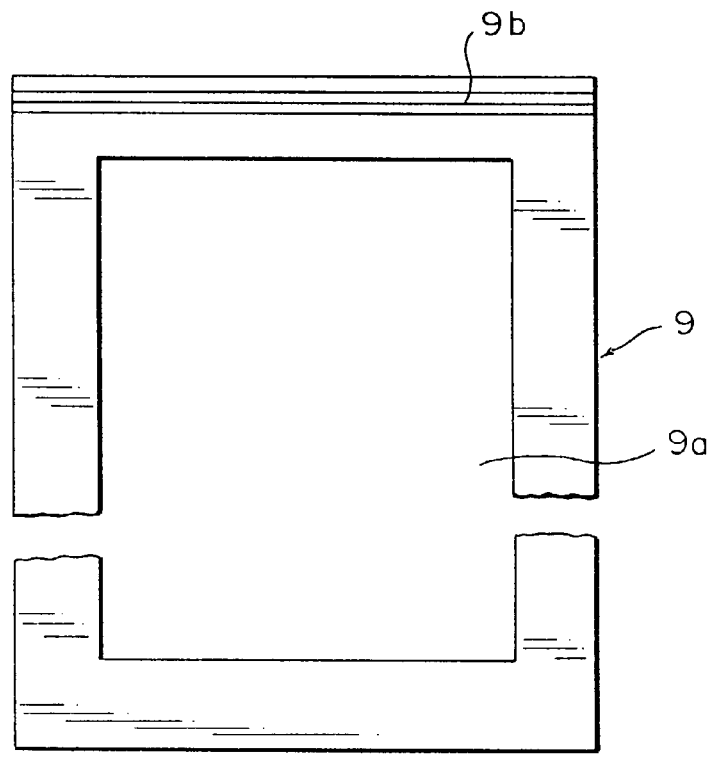
FIG. 2 is a schematic illustration of a frame of an embodiment of the present invention with a part of the frame cut away.
Figure 3:
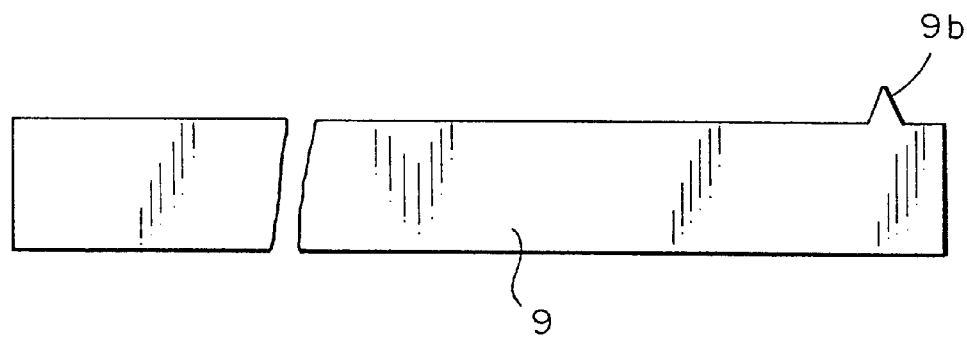
FIG. 3 is a side view of the frame shown in FIG. 2 with a part of the frame cut away.

Each frame 9 is a plate-like member of a generally rectangular shape, as shown in FIGS. 2 and 3, and has a central portion formed therein with a generally rectangular window 9a. A cutting edge 9b of a substantially triangular section is formed along a short end of the frame 9 between a short side of the window 9a and an adjacent short side of the frame 9. The cutting edge 9b has a straight ridge which acts as a knife edge and extends in the direction of the short side of the frame from one of the ends thereof to the other. The frame 9 is dimensioned such that the dimension of the frame along the short sides is greater than the width of the roll-like sheet 7 wound on the sheet-winding roll 6a while the dimension of the frame 9 in the longitudinal direction is greater than the dimension of the circumference of the sheet-winding roll 6a.

The window 9a in the frame 9 may be a simple opening free from any attachment or, alternatively, may have a transparent member such as a plate of acrylic acid resin or glass attached to the opening. The frame 9 has a surface adapted to support a sheet 7 applied thereto. This surface of the frame 9 should preferably be coated with a suitable pressure-sensitive adhesive to assure a reliable application of sheet 7.

The sheet applying means 4 may include a pinch roll 12 disposed in opposed relationship with its axis parallel to the sheet winding roll 6a and suitable drive means for driving the pinch roll 12 forwardly and backwardly, toward and away from the winding roll 6a. For example, the drive means may comprise a piston unit having a rod 13 connected at one end to the pinch roll 12 and a cylinder 14. The drive means for driving the pinch roll 12 forwardly and backwardly is not limited to the piston unit referred to above and may be of any other means that is operative to move the pinch roll forwardly and backwardly.

A sheet testing sample-making device 15 of the present invention comprises the above-described kneading rolls 2, frame feeding means 3 and sheet applying means 4.

As will be seen in FIG. 1, the foreign matter detecting means 5 includes a light irradiation means 17 disposed beneath a frame 9 carrying a sheet 7 applied thereto and an image pick-up means 18. The image pick-up means 18 is so disposed above the frame 9 as to face the light irradiation means 17. Judgement means 19 (see FIG. 8) is operative to discriminate foreign matter in the sheet 17 based on video signals from the image pick-up means 18. The sheet 7 is conveyed by suitable conveyance means such as a belt conveyor device 16.

The belt conveyor device 16 comprises at least two belt conveyors 16a and 16b arranged such that one 16a of the two conveyors is disposed upstream of the other 16b and the light irradiation means 17 and the image pick-up means 18 are disposed between the upstream and downstream belt conveyors 16a and 16b.

The light irradiation means 17 may be any one of the known light sources that can uniformly irradiate the sheet 7 applied to the frame 9 being conveyed.

The image pick-up means 18 may be any conventional device that is operative to pick up the image of the sheet 7 being irradiated and to output a video signal of the image thus picked up. An example of the image pick-up means is a video camera having a CCD pick-up element. The image pick-up means 18 may preferably be so structured as to not only pick up the image of the sheet 7 but also read identification marks provided on the frame 9, such as, for example, a reference number or bar code provided on the surface of the frame 9 by printing or stamping, and to output the discriminating data.

Figures 8, 9:
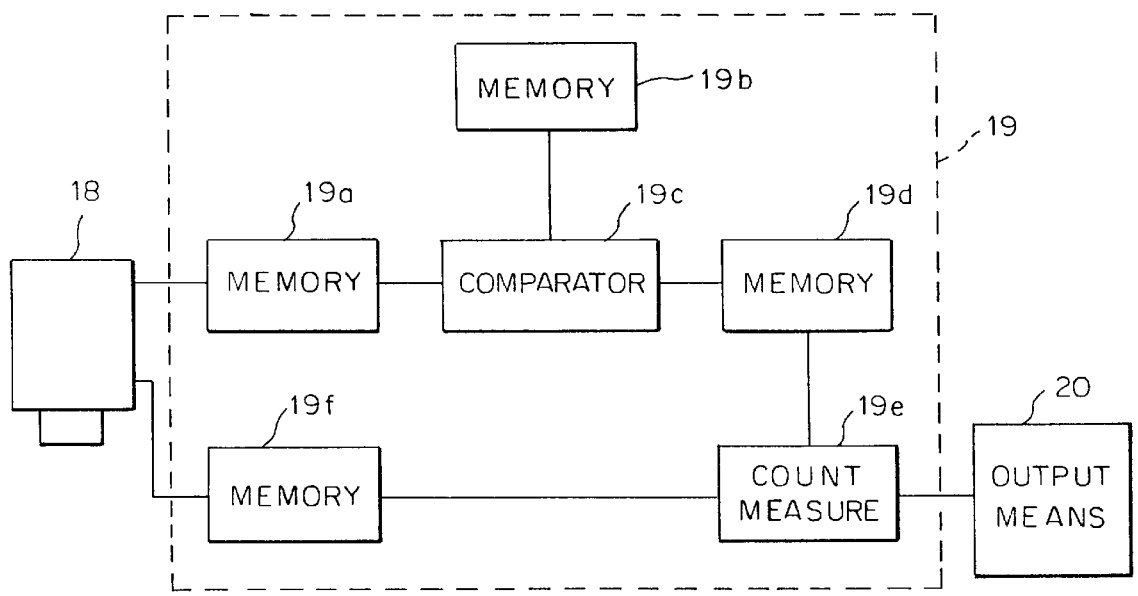
FIG. 8 is a block diagram of a judgement means in the sheet-testing apparatus.
FIG. 9 illustrates the principle of the judgement of the profile of a foreign material conducted by the judgement means.

The judgement means 19 comprises, as shown in FIG. 8, a first memory 19a for storing pickup signal values output from the image pick-up means for respective image elements; a second memory 19b for storing reference pick-up values obtained from an image of a sheet 7 free from any foreign matter; a comparator 19c operative to compare a pick-up value read from a predetermined address in the first memory 19a with a reference pick-up value read from a corresponding predetermined address in the second memory 19b and to output a judgement signal (for example, a signal "1" when the thus compared values are not in agreement with each other within a predetermined range of error and a signal "0" when the compared values are in agreement with each other); a third memory 19d for storing judgement signals "1" or "0" for respective addresses output from the comparator 19c; a processor 19e for generating a count of the number of, for example, fish eyes and gels, and a measure or measures of the sizes thereof, based on the judgement signals read out of the third memory 19d; and an output means 20, such as CRT or printer, for displaying the results of the counting or measuring operation.

The judgement means 19 may further include a fourth memory 19f in which the identification data on the various respective frames 9 imaged by the pick-up means 18 and and the data on foreign matter counted or measured by the processor 19e are written and from which they are read.

The sheet testing means 1 is provided with suitable transfer means (not shown in the drawings) that feed, to the conveyance means 16 of the foreign matter detecting means 5, a frame 9 that carries a sheet 7 after it has passed through the sheet-winding roll 6a and the sheet applying means 4.

Such transfer means may be in the form of a frame transfer means which comprises a chuck means operative to grip the upper end of a frame 9 to which has been applied (from the sheet winding roll 6a) the sheet 7, as the frame 9 was being lifted and pinched between the sheet-winding roll 6a and the pinch roll 12, and a chuck transfer means for transferring to the conveyance means the chuck means which grips the frame 9, which carries the sheet 7 applied thereto, after it is completely disengaged from the sheet winding roll 6a and the pinch roll 12. The transfer means may alternatively be in the form of a frame transfer means which comprises a guide means operative to guide directly to the conveyance means a frame 9 which has been pinched between the sheet-winding roll 6a and the pinch roll 12 and to which has been applied the sheet 7 from the sheet winding roll 6a while the frame 9 is being lifted.

The operation of the sheet testing means 1 having the described structure will be described hereunder.

In the initial stage of operation, an amount of elastic material such as a thermoplastic resin or rubber has been wound around the sheet winding roll 6a of the mixing rolls 2. The frame storing box 8 accommodates a plurality of frames 9 which are urged against one wall of the frame storing box 8 by the pressing roll 10. The pinch roll 12 is in its retracted position so that the sheet winding roll 6a and the pinch roll 12 are spaced to provide a sufficiently large gap therebetween.

Figure 4:
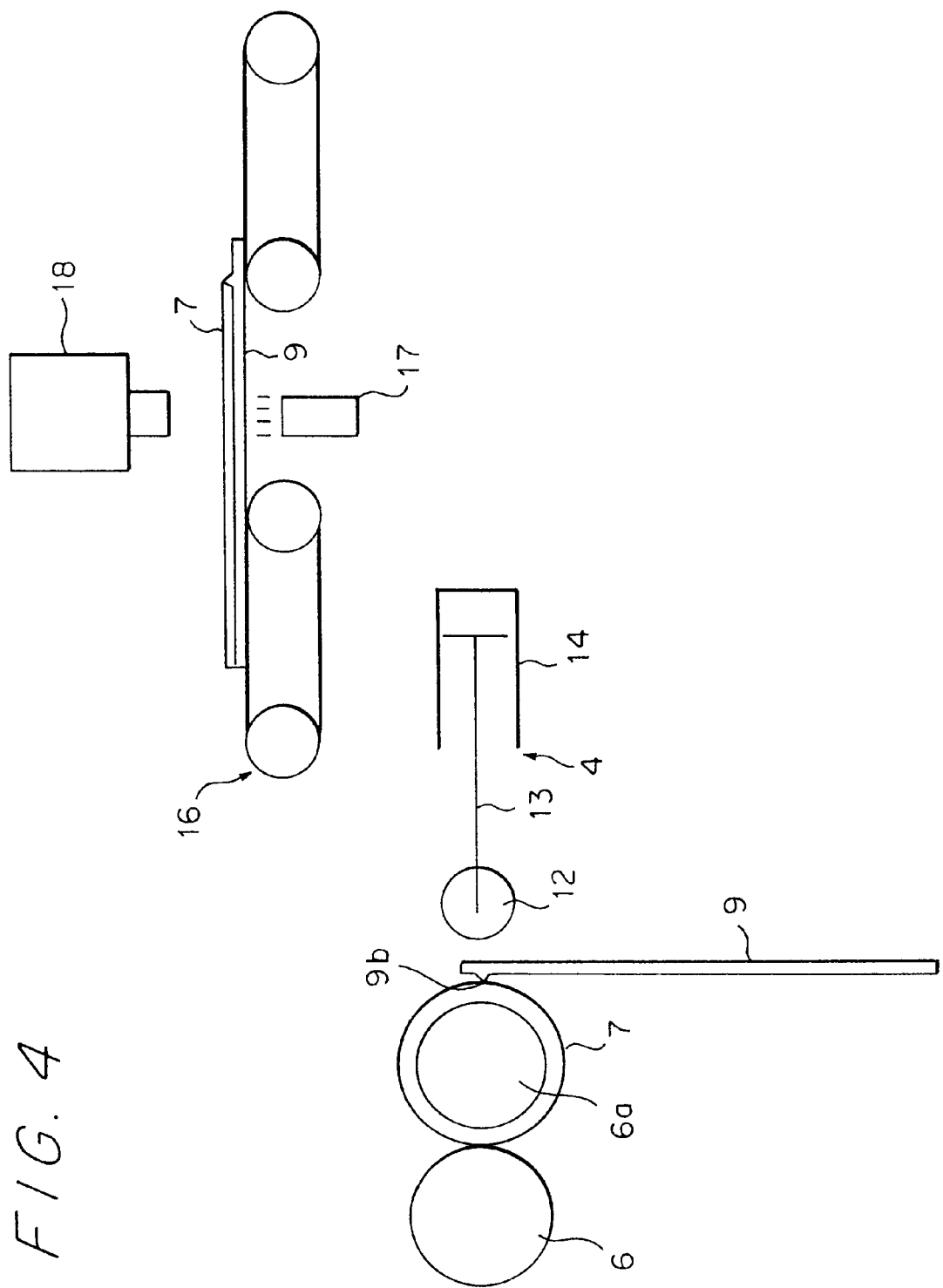
FIG. 4 is a schematic illustration of the operations of the sheet testing sample-making apparatus and the sheet-testing apparatus.

With the pinch roll 12 in this position, the bottom end surface of the outermost frame 9 which is urged against the wall of the frame storing box 8 is selected by the frame selection means (not shown), and by transporting operation of the guiding means 9g, the upper end of the frame 9, which end has the cutting edge 9b, reaches a point between the sheet-winding roll 6a and the pinch roll 12, as shown in FIG. 4, in such a manner that the cutting edge 9b is directed toward the sheet winding roll 6a.

Whether the upper end of the frame 9 reaches the point between the sheet winding roll 6a and the pinch roll 12 can be judged by known methods. An example will be presented below. The guiding means 9g is provided with the following control means 9c. The control means includes measuring device, judging device and instructing device. Full distance in which the frame is to be transported is first measured. The measured value of the full distance is inputted in the judging device. While the frame 9 is transported from the frame storing box 8 to the point between the sheet winding roll 6a and the pinch roll 12, the measuring device continues measuring the distance which the frame 9 is transported from the frame storing box 8. The measured value of the transportation is immediately transmitted to the judging device. The judging device continues comparing the measured value of the transportation with the full distance value and judging whether the measured value of the transportation meets the full distance value.

When the judging device judges that the measured value of the transportation meets the full distance value, the information of the meeting is transmitted to the instructing device. The instructing device instructs drive means 14 to drive the pinch roll 12 forwardly.

Figure 5:
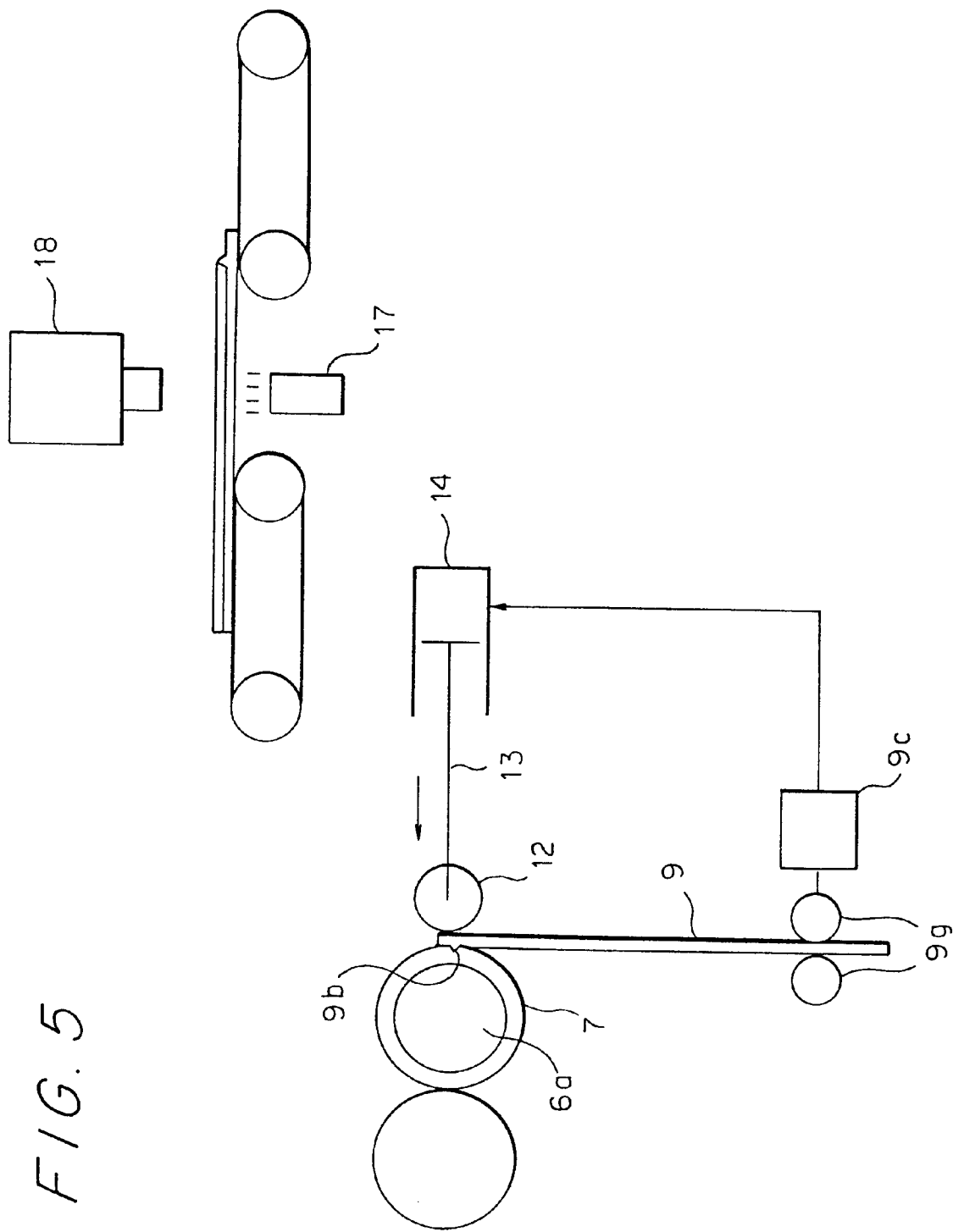
FIG. 5 is a schematic illustration of the operations of the sheet testing sample-making apparatus and the sheet-testing apparatus.

Then, the pinch roll 12 is driven by the drive means toward the sheet winding roll 6a until the frame 9 is pinched between the sheet 7 on the sheet-winding roll 6a and the pinch roll 12, as shown in FIG. 5. Because the cutting edge 9b (shown in FIG. 3) is formed on that surface of the end portion of the frame 9 which is directed toward the sheet-winding roll 6a, the pressing operation of the pinch roll 12 causes the cutting edge 9b to cut the sheet 7 on the sheet winding roll 6a.

Figure 6:
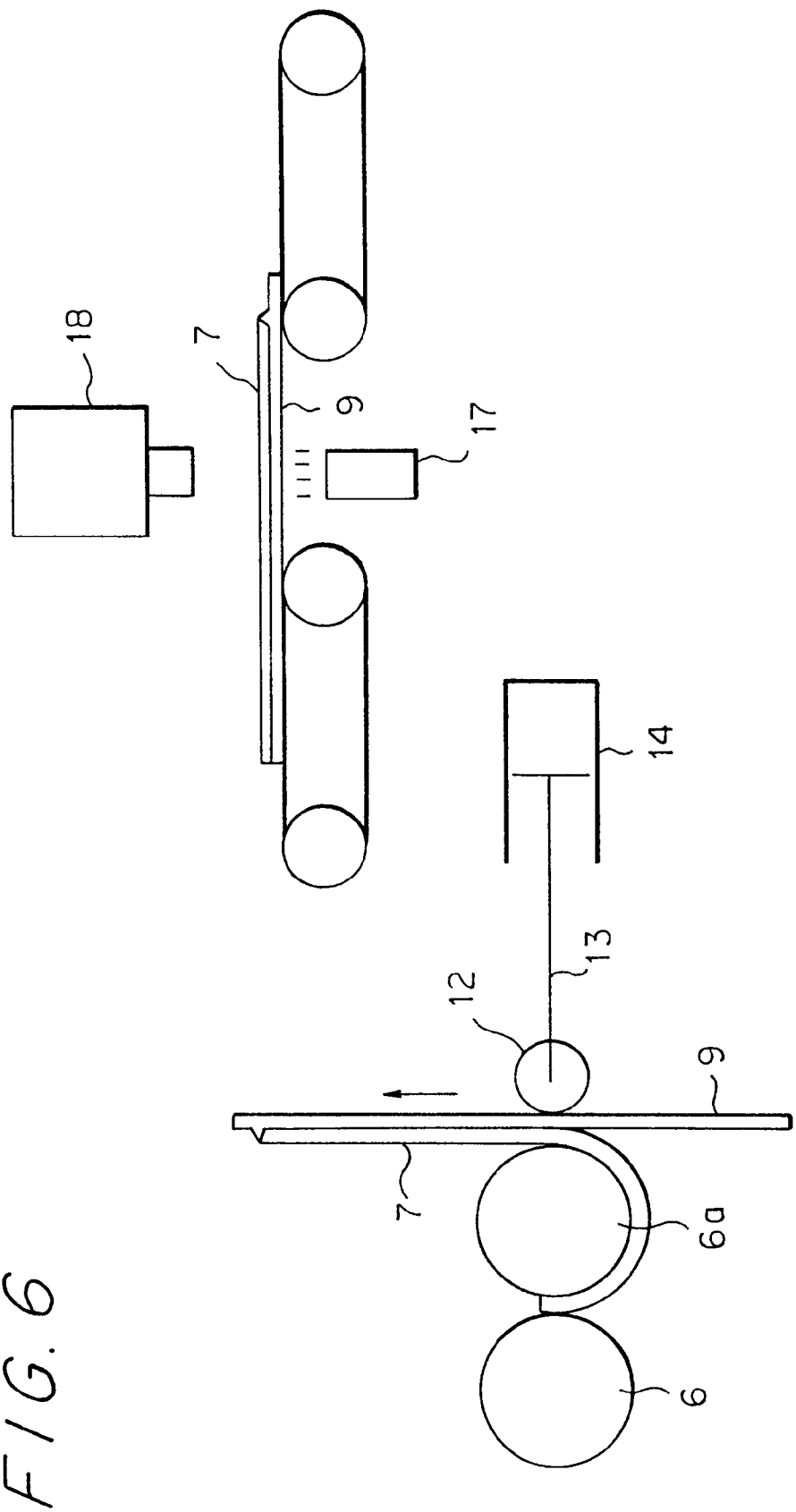
FIG. 6 is a schematic illustration of the operations of the sheet testing sample-making apparatus and the sheet-testing apparatus.

After the cutting, the frame 9 in question is continuously fed by the guiding means 9b. Thus, when this frame 9 is moved over the peripheral surface of the sheet-winding roll 6a, the sheet 7 is peeled away from the sheet-winding roll 6a and applied to the frame 9, as shown in FIG. 6. The pinch roll 12 only rotates following the upward-moving of the frame 9 and does not have a driver for its rotation.

Figure 7:
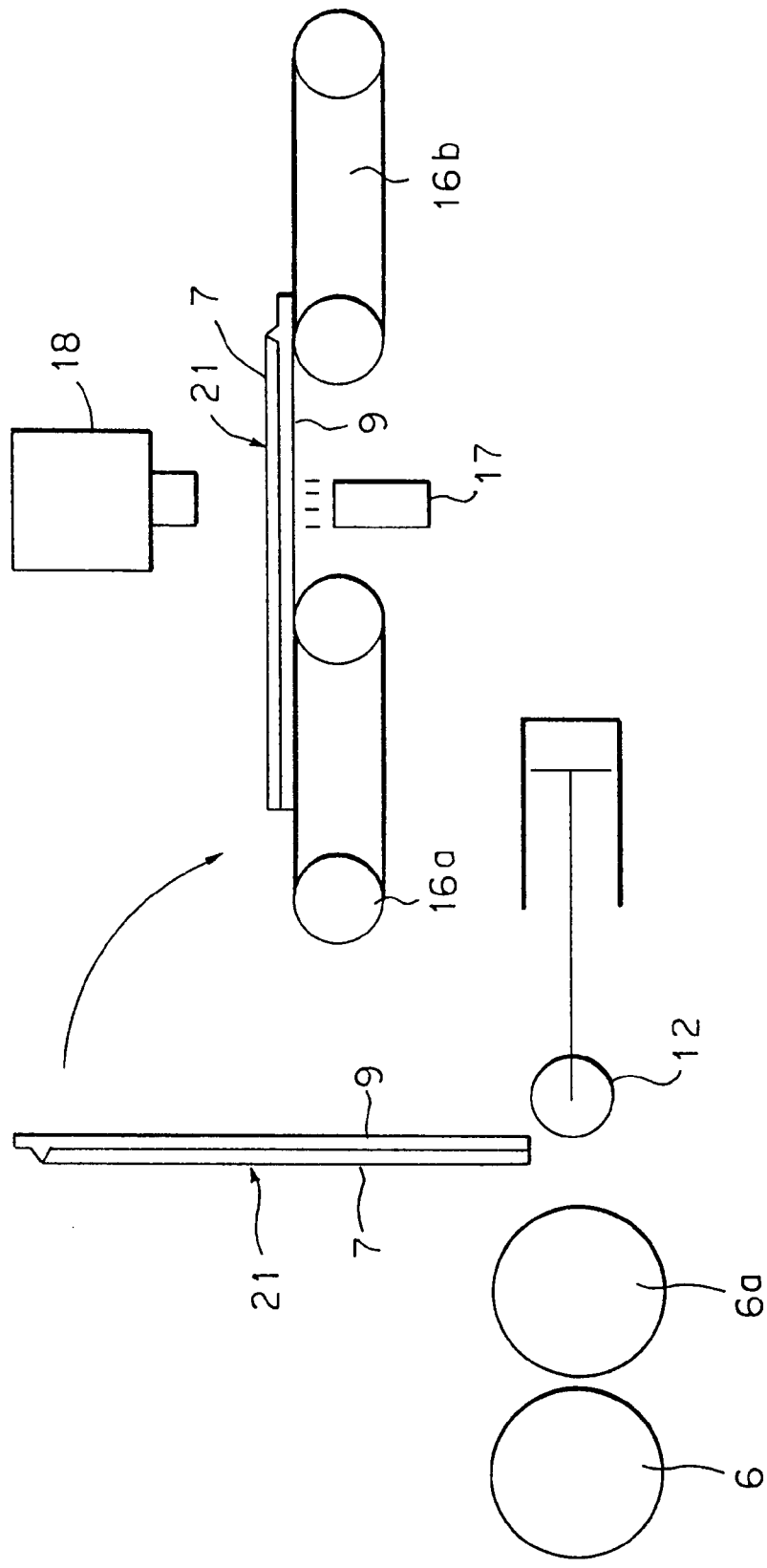
FIG. 7 is a schematic illustration of the operations of the sheet testing sample-making apparatus and the sheet-testing apparatus.

When the frame 9 is moved completely out of engagement with the sheet-winding roll 6a, the sheet 7 has been removed from the sheet-winding roll 6a and completely applied to the surface of the frame 9 that is provided with the cutting edge 9b, as shown in FIG. 7.

When the frame does not have the cutting edge on its surface and, instead, has the opening with the edge portion of a tapered or rounded shape, transferring the sheet or film wound on the sheet winding roll to the frame after cutting the sheet with the rolled sheet cutting device (not shown) results in a good sample. In this case, it is important to set the cut position of the sheet or film to the edge portion of the opening.

To setting the cut position of the sheet or film to the edge portion of the opening, known methods can be applied. For example, the method of judging whether the upper end of the frame 9 with the cutting edge 9b reaches the point between the sheet winding roll 6a and the pinch roll 12, described above, can be modified. The guiding means 9g is provided with the above-described control means 9c. The control means includes measuring device, judging device and instructing device. Full distance between the position of cutting the sheet or film wound on the sheet winding roll and the position of the edge portion of the opening of the frame 9 when the guiding means 9g first grips the frame 9 is measured at the outset. The measured value of the full distance is inputted in the judging device. The remaining steps are the same as those of the case where the frame has the cutting edge 9b on its surface. It is preferable that the sheet or film wound on the sheet winding roll is cut with the rolled sheet cutting device before the frame 9 is taken from the frame storing box 8.

The combination of the frame 9 and the sheet 7 applied thereto forms a sheet testing sample 21. In other words, the mixing roll cluster 2, the frame feeding means 3 and the sheet applying means 4 cooperate together to automatically make the sheet testing sample 21.

The frame 9 with the sheet 7 attached thereto (i.e., the sheet testing sample 21) is mounted on the upstream belt conveyor 16a as depicted in FIG. 7, by the transfer means (not shown). The sheet testing sample 21 is carried by the upstream belt conveyor 16a to the downstream belt conveyor 16b. When the sheet testing sample 21 bridges the upstream and downstream belt conveyors 16a and 16b, the sample 21 is irradiated with light by the light irradiation means 17.

The image pick-up means 18 picks up the image of the thus irradiated sheet 7 and inputs video image signals, corresponding to the sheet 7, to the judgement means 19.

As shown in FIG. 8, in the judgement means 19 the sheet 7 signals are stored in the first memory 19a as image element (pixel) values. Reference video signal values, which have been obtained from a reference sheet 7 free from any foreign matter, have been stored in the second memory 19b. The comparator 19c compares the video signal values read out of the addresses in the first memory 19a with the reference video signal values read out of the corresponding addresses in the second memory 19b. Then, the comparator 19c outputs to the third memory 19d digital signals, such as "1" signal when the thus compared signals are not in agreement with each other within a predetermined range of error, and "0" signal when the compared video signals are in agreement with each other. The operator 19e operates, based on the "0" or "1" signals read out of the third memory 19d, to locate foreign matter by clusters of "1"s. A cluster is shown schematically in FIG. 9. The judgement means 19 counts the number of foreign particles in terms of the number of clusters. The judgement means is also operable to measure the longer and shorter dimensions of each cluster to determine the size of the corresponding foreign particle. The judgment means 19 outputs the results of the counting and measurement to the output means 20 for displaying the results.

In the judgement means 19, the fourth memory 19f, which is capable of being written in and read out, may store the discriminating data which the image pick-up means 18 has produced by reading the identification marks on respective frames 9, and the data produced by counting or measuring the foreign matter. The fourth memory, if provided, makes it possible to access stored data on the foreign matter for any particular sheet 7 by operating an input means, such as keyboard, to input at any desired time discriminating data for the particular frame 9 of that particular sheet 7, and thereby obtain a read-out of the data for that sheet.

With the sheet-testing means 1 described in detail above, it is possible to automatically examine whether there is any foreign matter in the sheets 7 or not. With the described sheet testing sample-making device 15, it is possible to automatically make sheet-testing samples 21 suited for examination of sheets 7. With the described frame 9, it is possible to cut a sheet 7 wound on the sheet winding roll 6a and to apply to the frame surface the thus cut and separated sheet 7 to thereby make a sheet testing sample 21.

Figure 10:
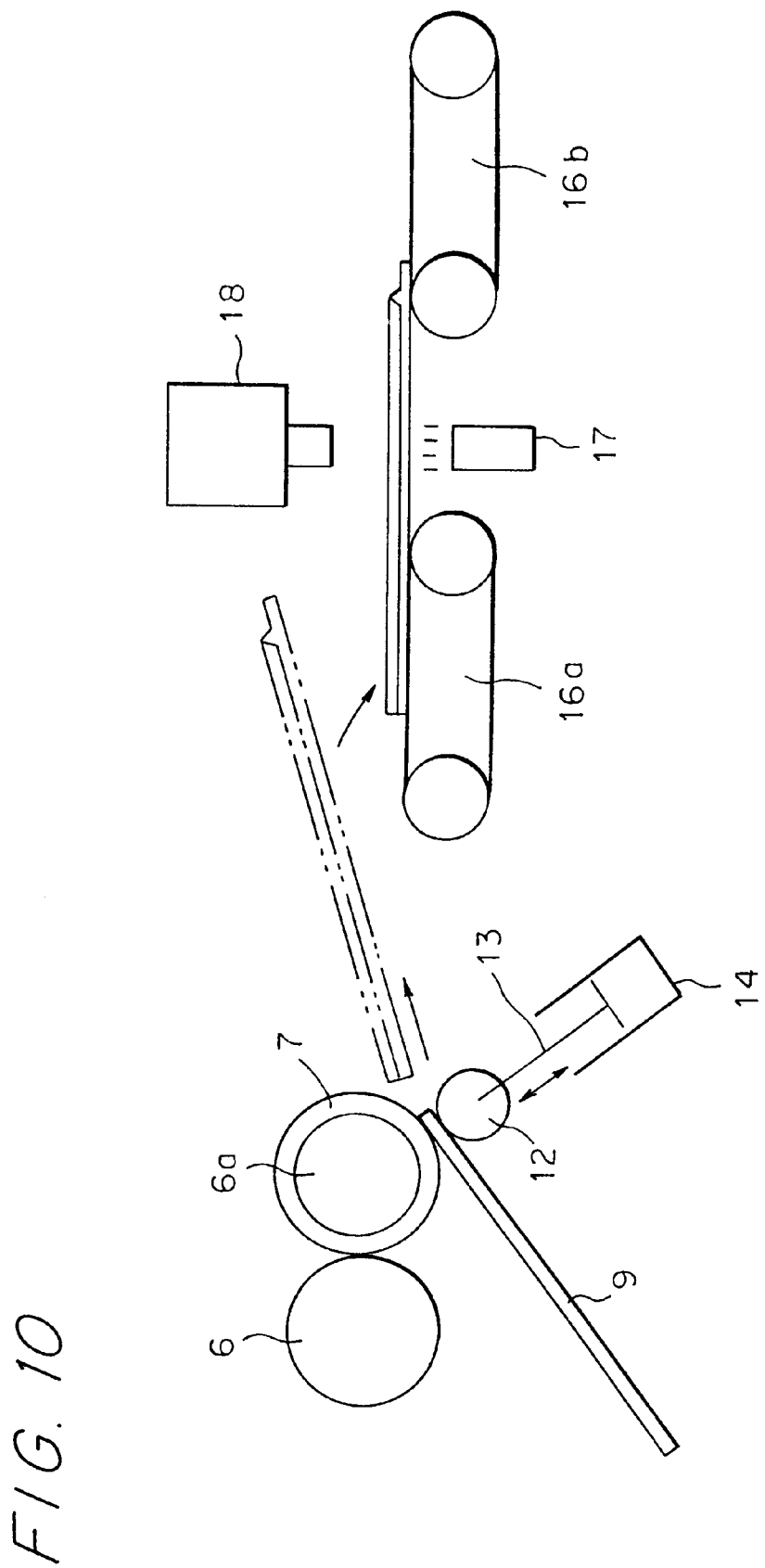
FIG. 10 is a schematic illustration of sheet testing sample-making apparatus and sheet-testing apparatus of another embodiment of the present invention.

In the described embodiment, the frame feeding means is arranged such that the frames are fed in the vertical direction. However, the frames 9 may alternatively be fed from the frame feeding means in an inclined direction, as shown in FIG. 10.

Figure 11:
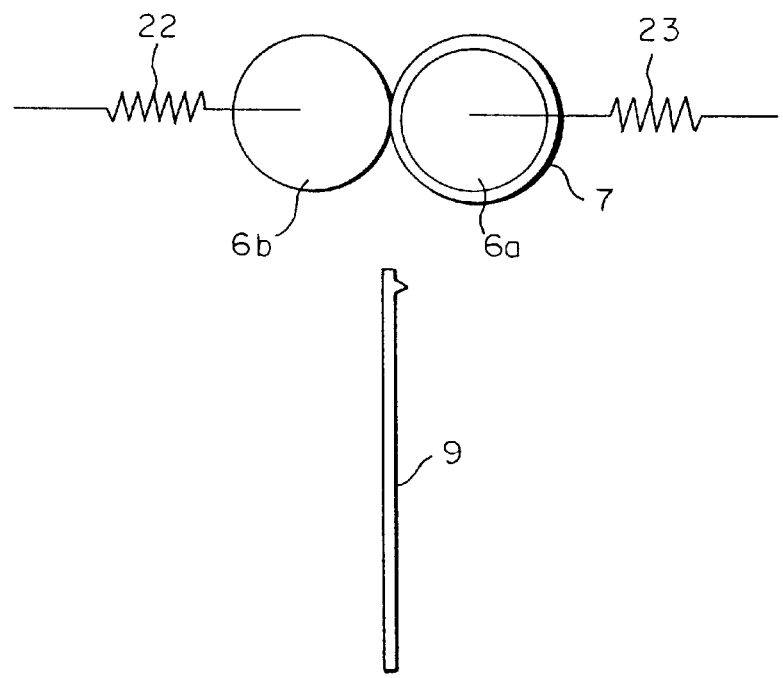
FIG. 11 is a schematic illustration of another example of a sheet application means in a sheet testing sample-making apparatus or a sheet-testing apparatus of another embodiment of the present invention.

In the described embodiment, the sheet applying means has a pinch roll 12 and a suitable drive means operative to drive the pinch roll 12 forwardly and backwardly. However, as shown in FIG. 11, the sheet applying means may alternatively have an opposing roll 6b disposed in opposed and parallel relationship to the sheet winding roll 6a. The counter roll 6b is movable toward and away from the sheet winding roll 6a by a first biasing member 22, while the sheet winding roll 6a is movable toward and away from the heating roll 6b by a second biasing member 23.

With this arrangement the frame 9 is adapted to be fed toward a gap between the sheet winding roll 6a and the counter roll 6b. The forward end of the frame 9 which has reached the gap is inserted into the gap to forcibly separate the sheet-winding roll 6a and the counter roll 6b away from each other. Because the end portion of the frame 9 which has entered the gap is squeezed by the first and second biasing members 22 and 23, the cutting edge 9b provided on the frame end portion forcibly cuts a sheet 7 on the sheet-winding roll 6a.

Figure 12:
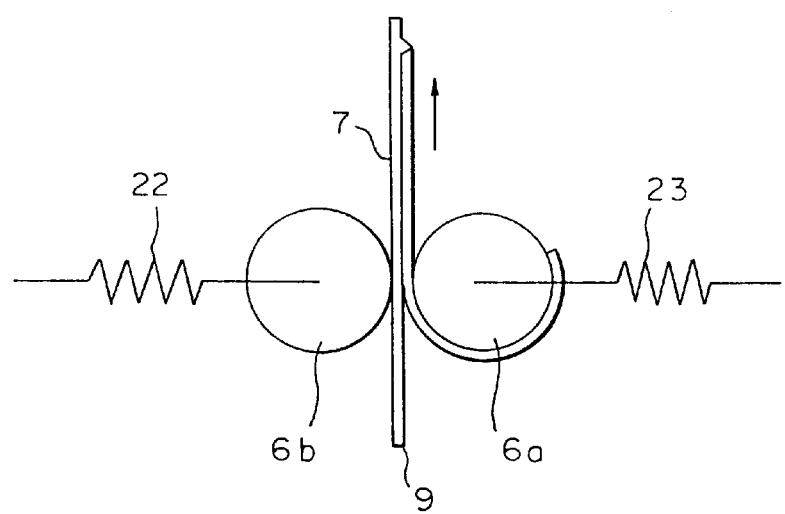
FIG. 12 is a schematic illustration of the operation of the sheet application means shown in FIG. 11.

As shown in FIG. 12, the frame 9 which has cut the sheet 7 is continuously fed by the frame feeding means (not shown in FIG. 12). As the frame 9 is lifted, therefore, the cut sheet 7 is removed from the sheet-winding roll 6a and transferred and applied to the surface of the frame 9. When the frame 9 is completely freed from the gap between the sheet-winding roll 6a and the heating roll 6b, the sheet 7 and the frame 9 now cooperate to form a sheet testing sample. The sheet testing sample is then transferred onto the conveyance means as in the embodiment shown in FIG. 1, so that the sample is tested by the image pick-up means as to whether any foreign matter is contained in the sheet or not.

Figure 13:
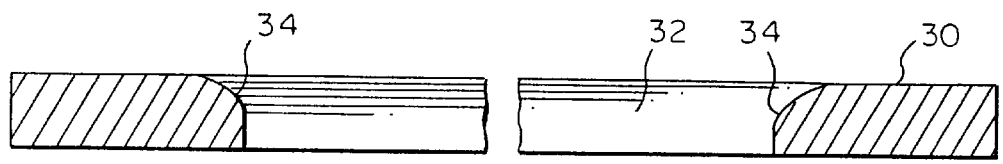
FIG. 13 is a sectional view of the frame of an embodiment of the present invention.
Figure 14:
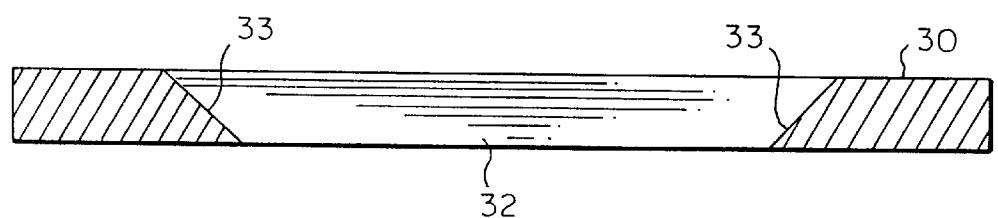
FIG. 14 is a sectional view of the frame of another embodiment of the invention.
Figure 15:
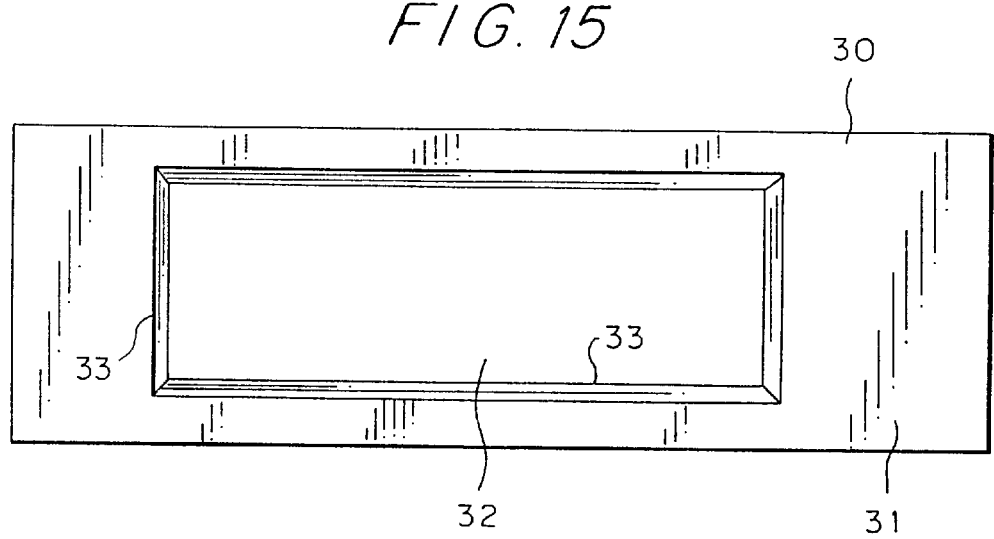
FIG. 15 is a front view of the frame of an embodiment of the present invention.

Other preferred embodiments of the frame of the invention are shown in FIGS. 13–15.

The frame 30, which is another preferred embodiment of the frame of the present invention, has a rectangular front side 31 and a window 32. The inner peripheral edge of the window 32 has an inclined surface which forms a tapered portion 33, as shown in FIG. 14. As an alternative, the inner peripheral edge of the frame 30 has, in place of the tapered portion 33, a rounded portion 34 formed by a rounded surface curved with an appropriate radius of curvature, as shown in FIG. 13.

When the frame 30 having a tapered portion 33 and/or rounded portion 34 along the peripheral edge of the window 32 is employed, a plastic sheet or plastic film wound around the sheet winding roll is separated from the sheet winding roll and is applied to the front side 31 of the frame 30 with the applied sheet tensioned appropriately only if the frame 30 is passed through the gap between the sheet winding roll and the heating roll which also acts as the counter roll.

Another embodiment of the frame feeding means of the invention can be suitably used with the sheet testing sample-making apparatus and the sheet-testing apparatus of the invention disclosed below.

Figure 16:
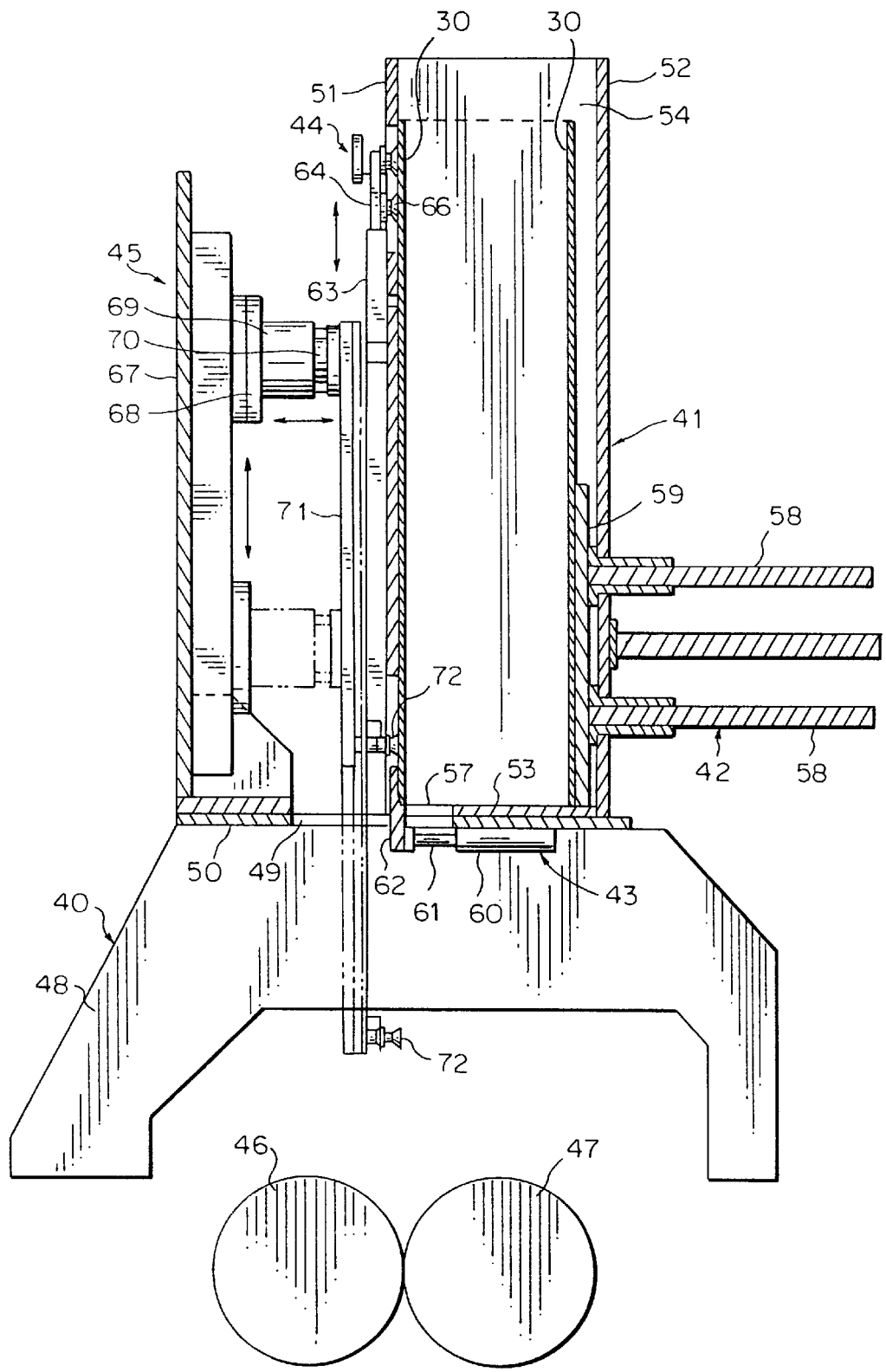
FIG. 16 is a partly sectional side view of a frame-feeding apparatus of an embodiment of the present invention.
Figure 17:
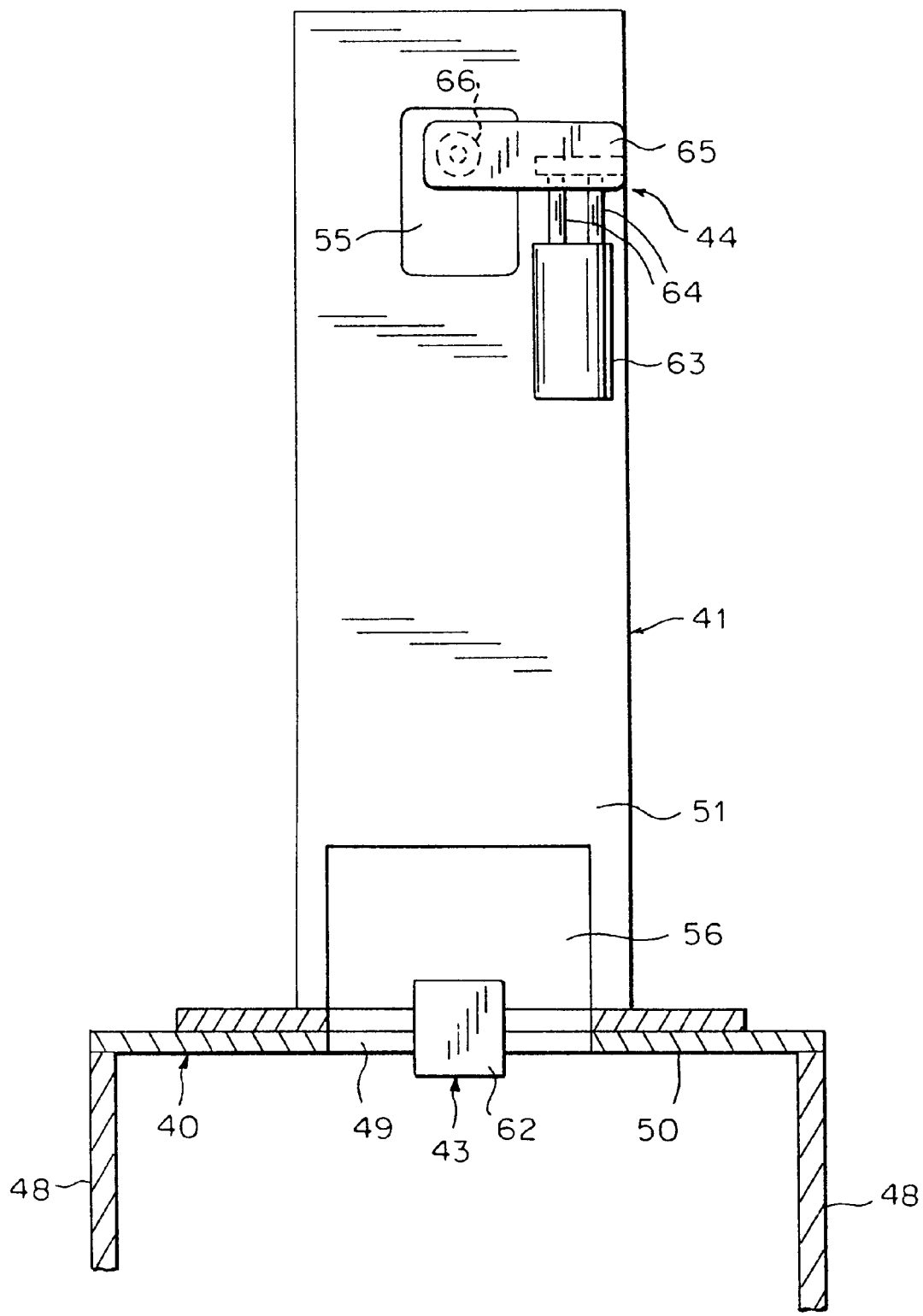
FIG. 17 is a front view of a housing of an embodiment of the frame-feeding apparatus of the present invention.

FIG. 16 is a partly sectional side elevational view of the frame feeding means, while FIG. 17 is a front elevational view of a housing.

As shown in FIGS. 16 and 17, the frame feeding means comprises a base 40, a housing 41, pressing member 42, a bottom pressing member 43, a take-up means 44 and guide means 45.

The base 40 comprises a pair of support plates 48 disposed in opposite relationship so as to support the axles (not shown) of sheet winding roll 46 and counter roll 47, and a top plate 50 mounted on and bridging the tops of the pair of support plates 48 and having formed therein a first opening 49 for allowing frames 30 to be freely moved therethrough.

The housing 41 is disposed on the top plate 50 of the base 40 and has a box-like structure comprising a front plate 51, corresponding to the front portion recited in claim 11, a rear plate 52 opposed to the front plate 51, a bottom plate 53, a pair of side plates 54 and a top plate (not shown). One of the pair of side plates 54 is openable to facilitate storage of frames 30 in the housing 41. As best shown in FIG. 17, an upper part of the front plate 51 is formed therein with an opening (referred to hereinafter as "upper opening 55"), while a lower part of the front plate 51 is formed therein with an opening (referred to hereinafter as "lower opening 56") which has an open bottom side. The bottom wall of the housing 41 has formed therein an opening (referred to hereinafter as "bottom opening 57") continuous with the lower opening 56 in the front plate 51. The length of the bottom opening 57 as measured in the direction extending from the front plate 51 to the rear plate 52 may be so adjusted that the space between the front plate 51 and the bottom pushing member 43 (to be described later) when in its position in the bottom opening 57 exceeds at least the thickness of a frame 30.

The pushing member 42 comprises, as best seen in FIG. 16, a pair of horizontal pushing rods 58 extending through the rear plate 52 of the housing 41, a vertical pushing plate 59 disposed in the housing 41 and connected to the inner ends of the pushing rods 58, and drive means (not shown) for driving the pushing rods 58 forwardly and backwardly.

The bottom pushing member 43 comprises, as best seen in FIG. 16 a first pneumatic cylinder 60 secured to the bottom surface of the housing 41, a first rod 61 movable forwardly and backwardly by the pneumatic force exerted by the pneumatic cylinder 60, and a vertical plate 62 connected to the free end of the first rod 61 and extending upwardly beyond the bottom surface of the housing 41 and terminating in an upper edge so adjusted as to be positioned below the upper edge of the above-mentioned lower opening 56.

The take-up means 44 comprises a second pneumatic cylinder 63 secured to the front plate 51 of the housing 41 adjacent the above-mentioned upper opening 55, a pair of second rods 64 movable upwardly and downwardly by the pneumatic force exerted by the second pneumatic cylinder 63, a horizontal supporting base plate 65 connected to the free ends of the second rods 64, and a first attraction cup 66 corresponding to the first attraction member recited in claim 11. The mounting position of the first attraction cup 66 on the supporting base plate 65, the length of each of the second rods 64 and the vertical stroke of the second rods 64 driven by the second pneumatic cylinder 63 are adjusted such that the second pneumatic cylinder 63 and the second rods 64 drive the first attraction cup 66 to its uppermost position adjacent the upper side of the upper opening 55 and the second pneumatic Cylinder 63 and the second rods 64 drive the first attraction cup 66 to its lowermost position adjacent the bottom side of the upper opening 55. The first attraction cup 66 is so structured that the air in the attraction cup is sucked by suction means, not shown. Accordingly, when the first attraction cup is pushed against a flat plate and the suction means is operated to suck air from the attraction cup, the first attraction cup is strongly attracted against the flat plate.

The guide means 45 comprises, as shown in FIG. 16, a vertical supporting base plate 67 upstanding from the top surface of the base 40 and positioned forwardly of the front plate 51 of the housing 41 with the first opening 49 positioned between the base plate 67 and the housing front plate 51; a first vertical lift mechanism formed by a third pneumatic cylinder (not shown) extending in, for example, the vertical direction and mounted on the surface of the base plate 67 directed toward the front plate 51, a third rod (not shown) vertically movable by the pneumatic force exerted by the third pneumatic cylinder and a first base 68 provided on the third rod; a second forward/backward drive mechanism formed by a fourth pneumatic cylinder 69 secured to the first base 68, a fourth rod 70 movable by the fourth pneumatic cylinder 69 toward and away from the front plate 51 and a vertically elongated second base 71 secured to the free end of the fourth rod 70; and a second attraction cup 72 mounted on the surface of the second base 71 directed toward the front plate 51 and disposed adjacent the lower end of the second base 71. The second attraction cup 72 is so structured that the air in the cup can be sucked therefrom by suction means, not shown. Accordingly, when the second attraction cup is pushed against a flat plate and the suction means is operated to suck air from the second attraction cup 72, the attraction cup 72 can be strongly attracted against the flat plate.

The operation of the frame-feeding means of the described structure is described hereunder.

First, a plurality of frames 30 are accommodated in the housing 41 and are urged against the rearwardly directed surface of the front plate 51 by the pushing plate 59. The positions of the second rod 64 and other associated members are adjusted to assure that the first attraction cup 66 is initially positioned slightly above the bottom side of the upper opening 55 and adjacent the surface of the forwardmost one of the frames 30 accommodated in the housing 41. In addition, the third rod (not shown) is initially set at its uppermost position, while the fourth rod 70 is initially set at its position retracted into the fourth pneumatic cylinder 69.

Then, the suction means for the first attraction cup 66 is operated to reduce the pressure in the first attraction cup 66, whereby the first attraction cup 66 is strongly attracted against the forwardmost frame 30.

Thereafter, the pushing rods 58 are retracted to reduce the force urging the pressing plate 59 against the stack of the frames 30, so that the clamping force exerted by the rearwardly directed surface of the front plate 51 and by the pressing plate 59 against the frames 30 is moderated. The second pneumatic cylinder 63 is then operated to lift the second rod 64, whereby the frame 30, attracted against the first attraction cup 66, is lifted a distance corresponding to the upward stroke of the second rod 64.

When the forwardmost frame 30 has been lifted by the first attraction cup 66, the first pneumatic cylinder 60 is operated to retract the first rod 61. Then, the second frame 30 and all the other frames 30 following the second frame are pushed by the vertical plate backwardly against the pushing plate 59 until these frames 30 are pinched by the vertical plate and the pushing plate 59 and, in addition, the vertical plate 62 is now in a position in which a frame 30 can pass through a gap defined in the bottom opening 57 between the vertical plate 62 and the front plate 51.

The fourth pneumatic cylinder 69 is operated to drive the fourth rod 70 forwardly, so that the second base 71 is moved toward the front plate 51 until the second attraction cup 72 is brought into contact with the surface of a lower portion of the forward-most frame 30. The suction means connected to the second attraction cup 72 is operated to suck gas from the second attraction cup 72, whereby the second attraction cup 72 is strongly attracted against the forwardmost frame 30.

When the second attraction cup 72 has been attracted against the forwardmost frame 30, the operation of the suction means for the first attraction cup 66 is stopped to allow gas to return into the first attraction cup 66, whereby the frame 30 is freed from the attraction by the first attraction cup 66.

Thereafter, the third pneumatic cylinder is operated to downwardly move the first base 68. The downward movement of the first base 68 lowers the fourth pneumatic cylinder 69 connected to the first base 68, the rod 70 of the fourth pneumatic cylinder 69, and the second base 71 connected to the fourth rod 70. The downward movement of the second base 71 lowers the forwardmost frame 30 attracted by the second attraction cup 72 so that the frame is moved downwardly out of the housing 41 through the bottom opening 57.

When the first base 68 is moved to its lowermost position by the operation of the third pneumatic cylinder, the bottom end of the frame 30, attracted and held by the second attraction cup 72 on the second base 71, is in a position to face the gap between a sheet-winding roll 46 and a counter roll 47.

When the operation of the suction means for the second attraction cup 72 is stopped, the frame 30 is freed from the attraction by the second attraction cup 72. Thereafter, the frame 30 is moved by gravity into the gap between the sheet winding roll 46 and the counter roll 47.

After the forwardmost frame 30 has been guided into the gap between the sheet winding roll 46 and the counter roll 47, the first pneumatic cylinder 60 is operated to move the vertical plate 62 to its initial position within the lower opening 56. Simultaneously with or after the forward movement of the first rod 61, the pushing rods 58 are moved forwardly to urge a plurality of frames 30 against the rearwardly directed surface of the front plate 51.

In addition, after the forward-most frame 30 has been guided to the gap between the sheet-winding roll 46 and the counter roll 47, the third pneumatic cylinder will be operated to lift the third rod to its initial position.

In the above-described manner, the frames 30 in the housing 41 can be fed one after another to the gap between the sheet winding roll and the counter roll.

According to the sheet testing apparatus of the invention, it is possible to fully and automatically search for foreign matter in sheets without requiring human operators' intervention. Moreover, because the examination of foreign matter does not rely upon visual observation by humans, the examination provides accurate results, to thereby eliminate the disadvantageous large errors that were in the past caused by visual observation by humans.

The frame according to the present invention is conveniently usable to make a sheet testing sample for use in the sheet-testing apparatus of the invention. Particularly, because the frame of the invention is provided with a cutting edge, the frame is capable of cutting a sheet on the sheet-winding roll so that the thus-cut sheet can be immediately applied to the frame to easily make a sheet-testing sample.

The sheet testing sample-making apparatus of the present invention can be used to make easily, completely, and automatically without requiring any human operation, sheet testing samples to be applied to the sheet testing apparatus of the invention.

The sheet of resin of the sheet testing sample made by the sheet testing sample making apparatus preferably has a uniform thickness of a predetermined dimension. The thickness of the sheet of resin made by the kneading rolls formed by the sheet winding roll and counter roll of the sheet testing sample making apparatus and wound on the sheet winding roll is controlled by an automatic sheet thickness detection device 101 to be described hereunder.

Figure 18:
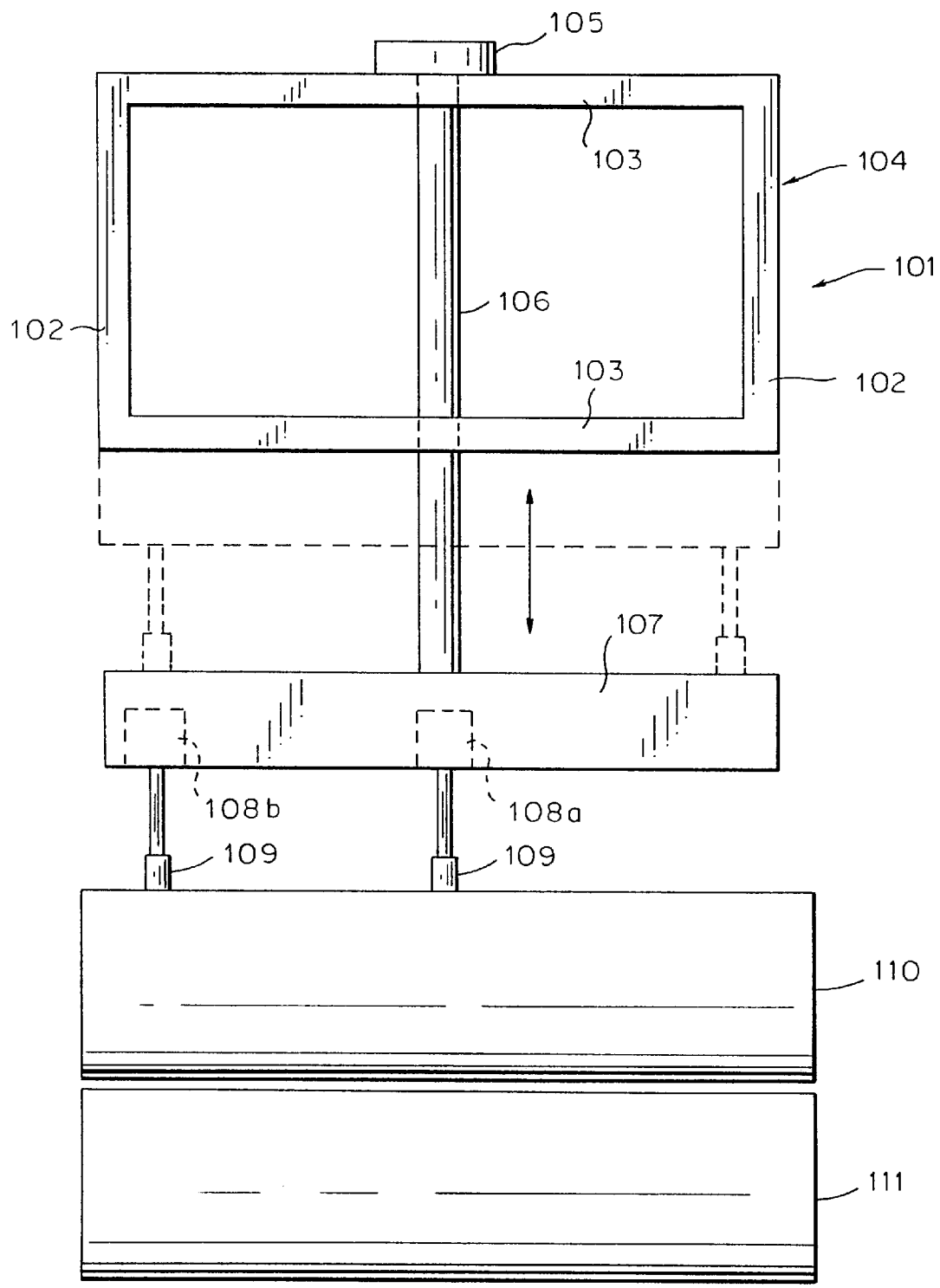
FIG. 18 is a schematic illustration of an automatic sheet-thickness detecting apparatus of the present invention.

As shown in FIG. 18, the automatic sheet thickness detection device 101 comprises a guide frame formed by a pair of longitudinal frame members 102; a rod-like support 106 extending through the pair of lateral frame members 103 of the guide frame 104 and having a stopper 105 at a rear end; a driving means (not shown) for moving the support 106 forwardly and rearwardly; a base 107 connected to the forward end of the support 106 and arranged to extend in parallel to the lateral frame members 103; first and second gauges 108a and 108b mounted on the base 107 and spaced a predetermined distance apart; and measuring elements 109 respectively connected to the first and second gauges 108a and 108b.

One of the measuring elements 109 is so positioned as to contact an end portion of a sheet wound around a sheet-winding roll 110 (or an end portion of the sheet-winding roll 110 itself if no sheet is present), while the other measuring element 109 is so positioned as to contact a central portion of the sheet wound around the sheet winding roll 110 (or a central portion of the sheet winding roll 110). The provision of these measuring elements 109 in this positional relationship makes it possible to measure the thicknesses of the end portion and central portion of the sheet simultaneously to assure the uniformity of the sheet thickness.

The first and second gauges 108a and 108b may be any conventional measuring means, such as a micrometer which, when the associated measuring element 109 is brought into contact with an object, detects the displacement of the measuring element 109 and outputs an electrical signal representative of the thus-detected displacement.

A heating and kneading roll means includes at least the sheet winding roll 110 and a counter roll 111 disposed in opposite relationship to the sheet winding roll and having an axis parallel to the axis of the sheet winding roll 110. The sheet thickness detecting device 101 of the present invention is so structured that the support 106 is moved toward and away from the sheet winding roll 110.

Figure 19:
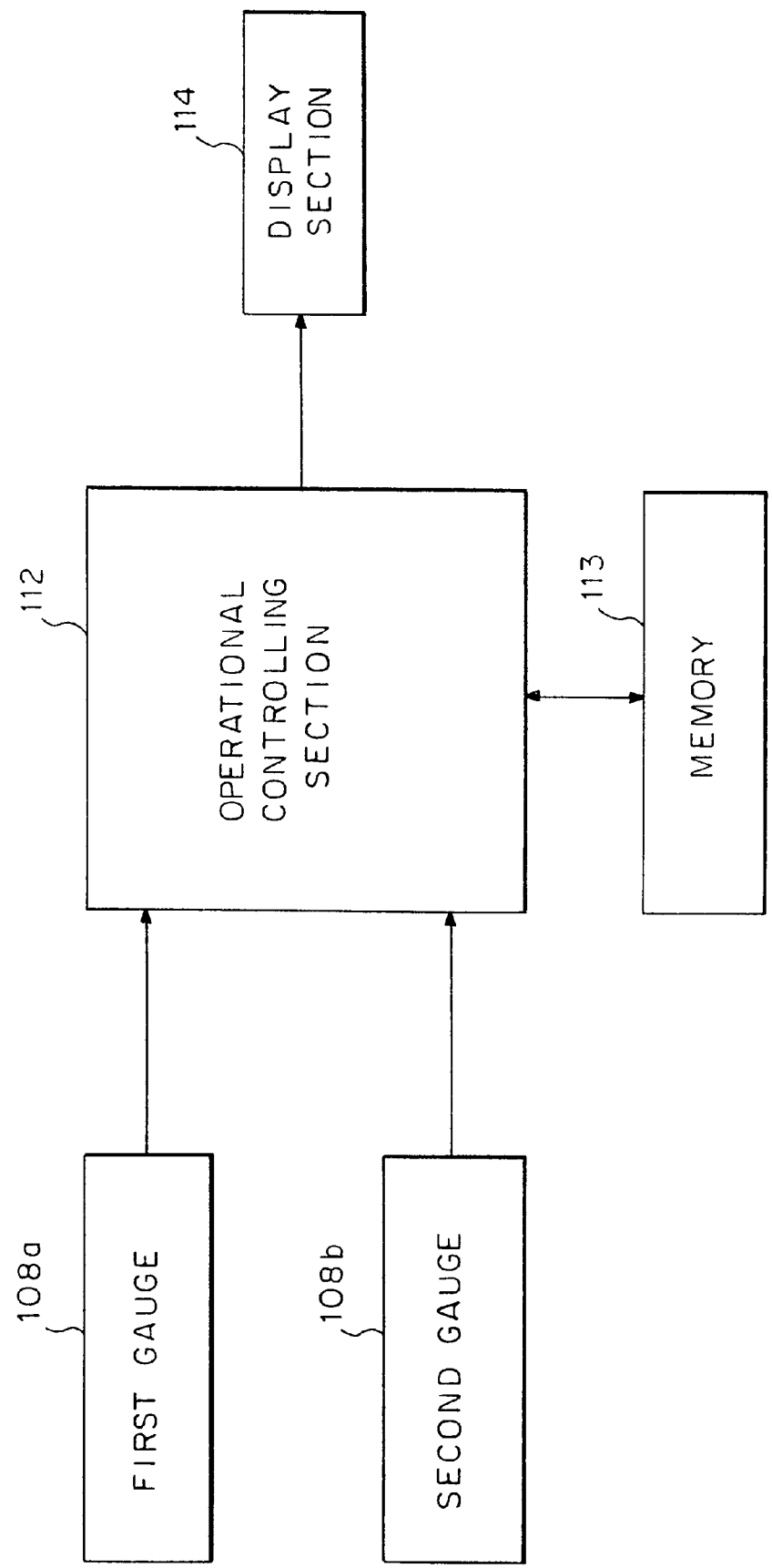
FIG. 19 is a block diagram for a data processor in the automatic sheet thickness detecting apparatus of the present invention.

As shown in FIG. 19, the sheet thickness detecting device 101 further includes an operational controlling section 112 which is operative to calculate the sheet thickness based on the data output by the pair of gauges, first and second gauges 108a and 108b. More specifically, the measuring elements 109 are first moved into contact with the surface of the sheet-winding roll 110 without any sheet wound thereon. The displacements of the measuring elements 109 are detected by the first and second gauges 108a and 108b which output corresponding initial data to the operational controlling section 112. The initial data are provisionally stored in a memory 113. The measuring elements 109 are again moved into contact with a sheet wound on the sheet winding roll 110. The displacements of the measuring elements are detected by the first and second gauges 108a and 108b which output measured data to the operational controlling section 112 in which the initial data are subtracted from the measured data to determine the sheet thicknesses measured by the first and second gauges 108a and 108b. The values thus calculated are then output to a display section 114.

The operation of the automatic sheet thickness detecting device 101 is described hereunder.

In the automatic sheet thickness detecting device 101, the base 107 is initially retracted to a position adjacent the lateral frame member 103 of the guide frame 104. The guide frame 104 has a function of supporting the support 106 and is not limited to the structure shown in FIG. 18 so long as the frame has this function. When a stage is reached in which the heat winding roll 110 is heated to knead an amount of resin, an actuator (not shown) moves the frame 107 toward the sheet winding roll 110 to bring the pair of measuring elements 109 into contact with the surface of the sheet winding roll 110. When the pair of measuring elements 109 are in contact with the surface of the sheet winding roll 110, the first and second gauges 108a and 108b detect the displacements of the measuring elements 109 and output to the operational controlling section 112 electrical signals representative of initial data of the thus-measured displacements. The initial data are then transmitted from the operational controlling section 112 to the memory 113 and provisionally stored therein. When the measurement by the measuring elements 109 is finished, the base 107 is retracted to move the measuring elements 109 away from the sheet winding roll 110 until the base 107 returns to its initial position.

Then, a predetermined amount of powdered resin (not shown in FIG. 18) is fed to a gap between the sheet winding roll 110 and a counter roll and the kneading rolls are rotated to knead the powdered resin, with the result that a sheet of the kneaded resin is formed on the surface of the sheet-winding roll 110. After the lapse of a predetermined time period, the base 107 is moved forward to bring the pair of measuring elements 109 into contact with the sheet on the sheet winding roll 110. As the measuring elements 109 are brought into contact with the sheet, the first and second gauges 108a and 108b output to the operational controlling section 112 an electrical signal representing the displacements of the measuring elements 109. When the measured data has been input into the operational controlling section 112, the base 107 is retracted to its initial position.

The operational controlling section 112 operates to read out of the memory 113 the initial data and subtract it from measured data input to the operational controlling section 112 to thereby determine the sheet thickness which is then displayed on the display section 114.

If the sheet thickness measured by the first gauge 108a and the sheet thickness measured by the second gauge 108b are greatly different beyond an allowable range of error, the kneading is further continued. The measuring operation is repeated to measure the thickness of the sheet on the sheet winding roll 110 until the sheet thickness measured by the first gauge 108a becomes equal to the sheet thickness measured by the second gauge 108b within the allowable range of error. Then, the sheet is removed from the sheet winding roll 110.

As described in detail above, according to the present invention, it is possible to automatically measure the thickness of a sheet on a sheet winding roll. Thus, the present invention can provide a safe automatic sheet thickness detecting device which can eliminate any accident, such as a burn caused when an operator gets in touch with the heating roll or an injury of a finger pinched between rolls.

Moreover, since the automatic sheet thickness detecting device detects sheet thickness without relying upon an operator, the resultant measured data do not suffer from operator error but precisely represent the measured sheet thickness.

In addition, the automatic sheet thickness detecting device measures the thickness of a sheet on the sheet-winding roll at least at two points thereof. Accordingly, it is possible to finely adjust the gap between the kneading rolls whenever the sheet thickness is measured, to thereby easily produce sheets of uniform thickness.

Figure 20:
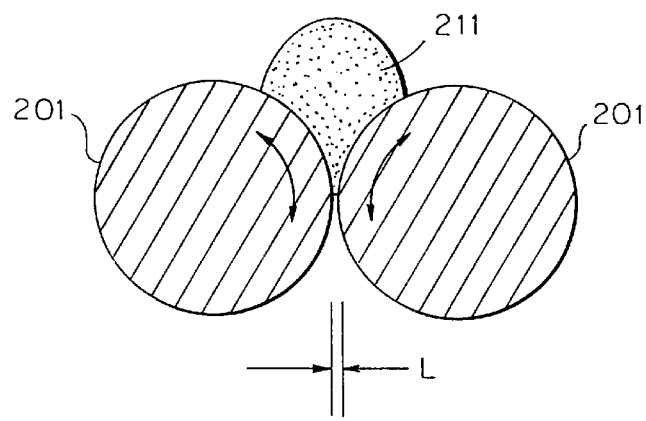
FIG. 20 is a schematic illustration of a mound or deposit of powdered material above a gap between heating rolls.

FIG. 20 shows, in sectional view, a pair of heating rolls of a mixing device in an embodiment of the present invention.

As shown in FIG. 20, the pair of heating rolls 201 are disposed in opposed relationship with their axes extending in parallel relationship. The pair of heating rolls 201 are arranged such that the distance L between the pair of heating roll 201 can be adjusted by drive means, not shown, such that the heating rolls 201 can be heated to respectively predetermined temperatures by heating means, not shown, and such that the pair of heating rolls 201 can be rotated by drive sources, not shown, at independent speeds and directions.

The heating rolls 201 are each provided with a temperature sensor for sensing the raised temperatures thereof, a rotational condition sensor for detecting the directions and speeds of the rotations of the heating rolls 201, a position sensor for detecting the gap between the pair of heating rolls 201, and a bank sensor for sensing a bank of a material deposited above the gap, such as a mound of powdered, partially melted, or melted material.

The temperature sensor may be a thermocouple or infrared radiation thermometer. The rotational condition sensor may comprise, for example, a rotary encoder for detecting the rotational speeds of the heating rolls 201 and a rotary encoder for detecting the directions of rotations of the heating rolls 201. The position sensor may be a laser type displacement sensor or an ultrasonic displacement sensor. The bank sensor may be a non-contact thermometer, such as an infrared radiation thermometer, or a combination of a luminous means, disposed adjacent to the gap between the pair of rolls and radiating light in the axial direction of the rolls, and a light receiving sensor for receiving the thus radiated light.

Figure 21:
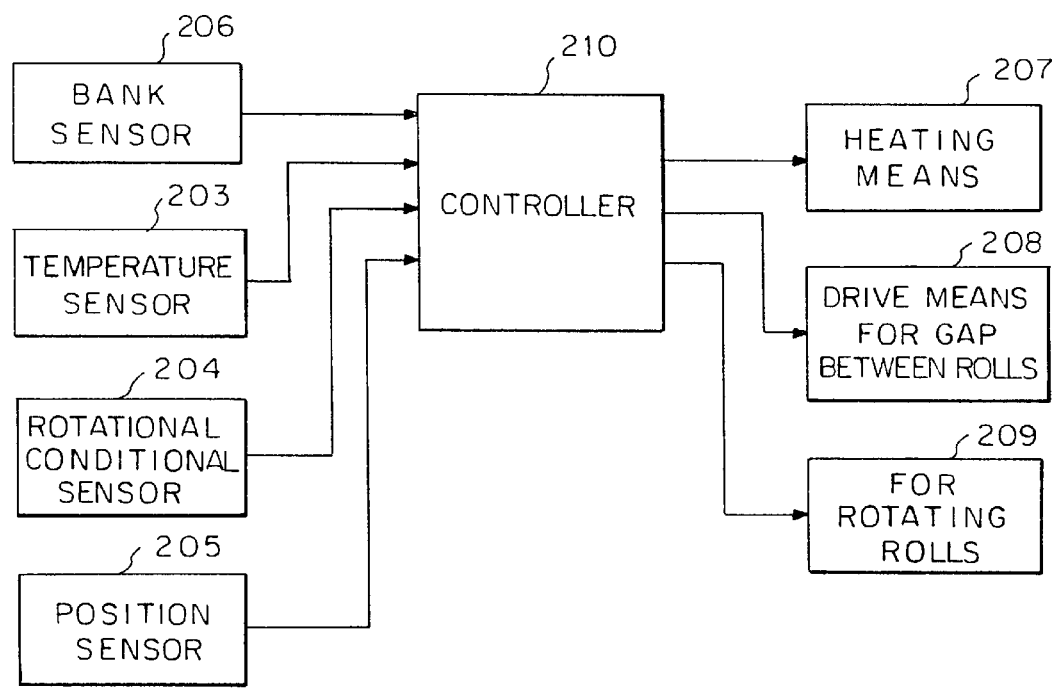
FIG. 21 is a block diagram of a kneading apparatus of an embodiment of the present invention.

The kneading means of this embodiment comprise the above-mentioned pair of heating rolls 201 and, as shown in FIG. 21, the temperature sensor 203, the rotational condition sensor 204, the position sensor 205, the bank sensor 206, heating means 207 for heating the heating rolls 201, drive means 208 for adjusting the gap between the heating rolls 201, a device 209 for driving the heating rolls 201 at the desired rotational speeds and directions, and control means 210 operative to receive detection signals output from the various sensors to control the heating means 207, the drive means 208 and the driving device 209 in accordance with the condition and the amount of the resin deposit existing in the gap between the pair of heating rolls 201. In addition, the kneading means is provided with an input means such as keyboard, not shown in FIG. 21, operable to input various data and control signals into the control means 210.

The operation of this embodiment is described hereunder.

Figure 22:
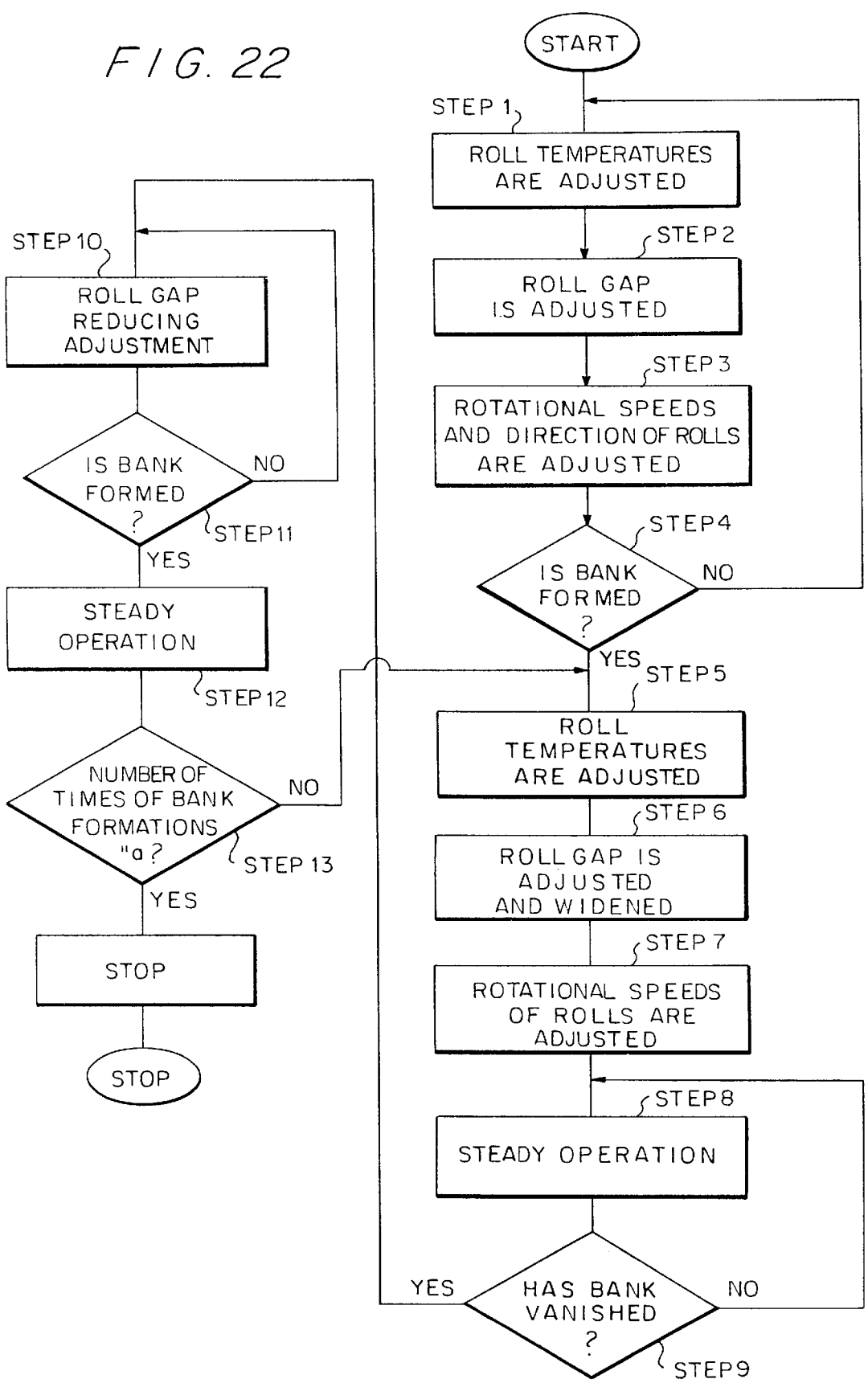
FIG. 22 is a flow chart of a controlling program in the kneading apparatus of an embodiment of the present invention.

As shown at Step 1 in FIG. 22, the control means 210 outputs to the heating means 207 a heating control signal in accordance with heating temperature measurements input in advance by the input means (temperature sensor 203) so that the heating rolls 201 are heated by the heating means 207 to predetermined temperatures. The heating temperatures are variable according to the kind of material. In the case where the material is a vinyl chloride resin or silicon resin, the heating temperature is usually set to about 10° C. higher than the working temperature of the resin. The set temperatures are input in the control means 210 by the keyboard.

As shown at Step 2 in FIG. 22, the control means 210 outputs a gap control signal to the drive means 208 so that the relative position of the heating rolls 201 is adjusted to set the distance L between the pair of heating rolls 201 to be of a predetermined distance. In the initial state, the distance L between the pair of heating rolls 201 is, usually, about 0.1 mm.

As shown in FIG. 20, a predetermined amount of material 211 is deposited above the gap between the pair of heating rolls 201 with the distance therebetween having been adjusted to be L. The amount of the powdery material 211 to be stored in the gap or valley between the heating rolls 201 is, usually, sufficient to form a sheet of resin of predetermined thickness and width to be applied to the frame. This amount of the powdery material to be stored in the above-mentioned valley is generally applicable to the present invention. Because the pair of heating rolls 201 are spaced the above-mentioned distance L, there is a possibility that, when powdered material is fed to the gap between the heating rolls 201, the thus-fed material leaks and falls through the gap. However, the leakage is small. Normally, particles of the powdered material bridge over the distance L between the pair of heating rolls 201, and the leakage of the powdered material through the distance L is almost immediately terminated.

As shown in FIG. 22, the control means 210 outputs drive control signals to the driving device 209 so that the pair of heating rolls 201 are rotated at predetermined speeds and in predetermined directions, respectively. In this case, the rotational speeds and directions of the heating rolls 201 are dependent on the kind of materials and, in general, so determined that particles of the powdered material are fused together and kneaded by the heating rolls 201. For one material, the driving device 209 might be controlled such that the pair of heating rolls 201 are rotated in the opposite directions and at low speeds. For another material, the pair of heating rolls 201 may be rotated in the same direction but at different and low speeds. In summary, the rotational speeds and directions of the heating rolls 201 are determined by the control means 210 such that a large shearing force and thermal energy are imparted by the heating rolls 201 to the powdered material 211 existing on the pair of heating rolls 201 to fuse the particles of the powdered material together.

The kneading is continued with the heating temperatures of the heating rolls 201 and the rotational directions and speeds of the heating rolls maintained unchanged until the particles of the powdered material 211 are fused together, and a bank of the material is formed on the heating rolls 201. At this time, the bank volume is substantially determined and the torques imparted to the heating rolls 201 are reduced. The bank sensors detect such volume of the bank or the reduction in the torques imparted to the heating rolls 201 and thereupon output a detection signal to the control means 210.

Before receiving the detection signal, the control means 210 decides that such a bank has not yet been formed and the process is returned, from Step 4 to the Step 1 of FIG. 22 so as to further adjust the spacing L between the heating rolls 201, the heating temperatures of the heating rolls 201, and the rotational speed and directions of the heating rolls 201.

FIG. 22 shows the adjustment of the temperatures of the heating rolls 201 at the Step 1, the adjustment of the space between the heating rolls 201 at the Step 2, and the adjustment of the rotational speeds and directions of the heating rolls 201 at the Step 3 and indicates these steps to be conducted in this sequential order. However, the sequential order of the Steps 1–3 is not limited to the order shown in FIG. 22. Namely, the Steps 1–3 may alternatively be conducted simultaneously or in the reversed order.

If a bank of the material is formed over the space L between the heating rolls 201, the control means 110 outputs a temperature control signal to the heating means 207 to change the roll temperatures to predetermined levels (Step 5), the space L between the heating rolls 201 is gradually changed (Step 6), and the rotational speeds and directions of the heating rolls 201 are maintained to be constant (Step 7).

Usually, the heating temperature attained at this time at the heating rolls 201 is the working temperature of the material. The directions of rotations of the heating rolls 201 are adjusted to be the opposite directions such that the bank of the material is drawn into the space L between the heating rolls 201. The rotational speeds of the heating rolls are adjusted to be optimum for the particular kinds of material.

Figure 23:
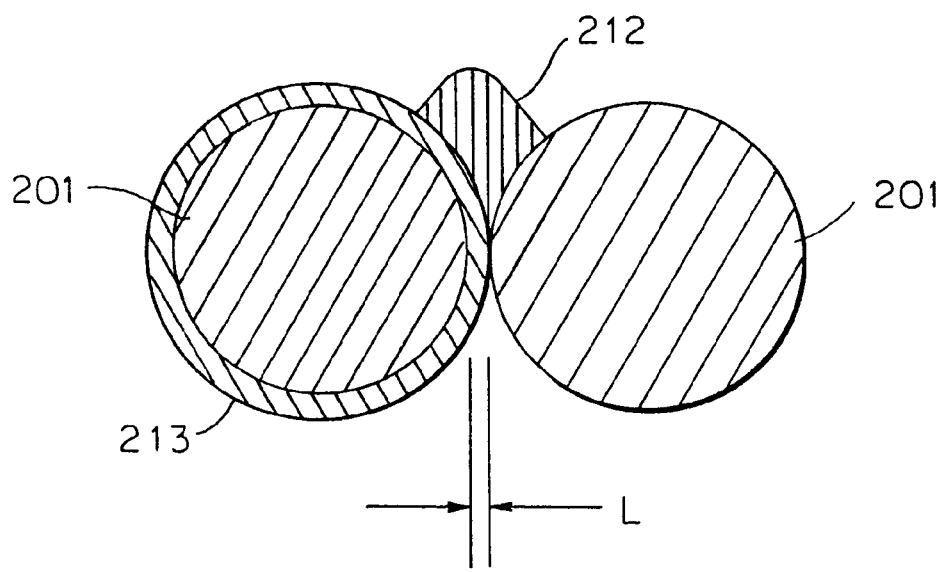
FIG. 23 is a schematic illustration of a bank formed above a gap between heating rolls.
Figure 24:
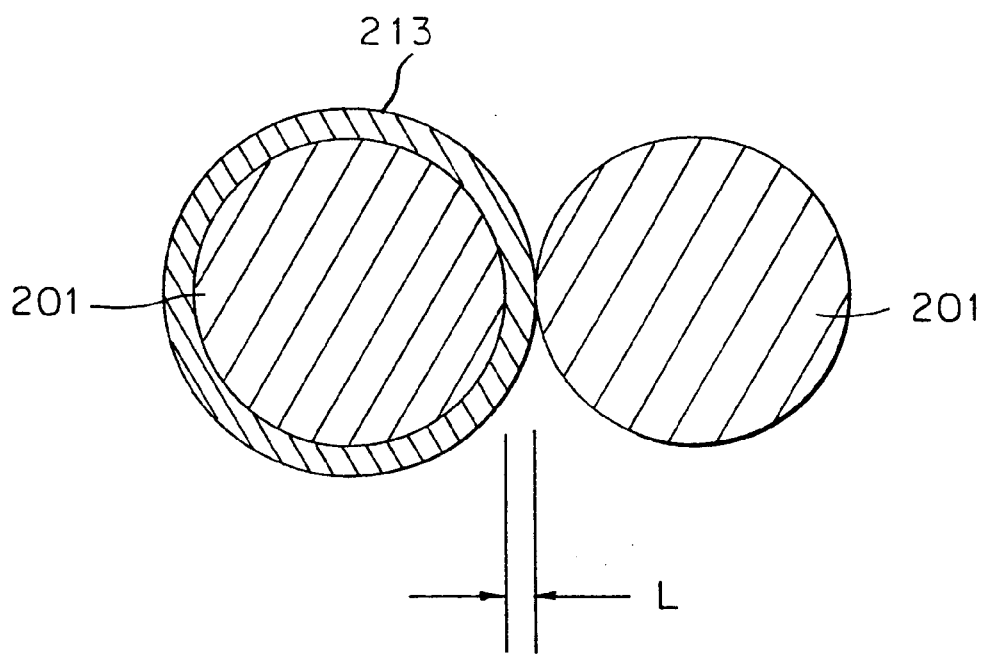
FIG. 24 is a schematic illustration of the heating rolls with the bank above the gap between the heating rolls gone and with a rolled sheet formed on one of the heating rolls.

As shown in FIGS. 23 and 24, as the kneading of the bank 212 is effected by the heating rolls 201 and the space L between the heating rolls 201 is gradually increased, one of the heating rolls 201 becomes to be wound with a roll-like sheet 213 and the thickness of the roll-like sheet 213 thus wound is gradually increased.

In this state, a steady operation of the heating rolls 201 is conducted for a predetermined time to knead the material (Step 8). The bank sensor 206 watches the bank 212 over the space between the heating rolls 201 (Step 9). When the bank sensor 206 detects the presence of the bank 212 on the working rolls 201, the sensor outputs a detection signal to the control means 210 which, upon receipt of the detection signal, directs the heating means 207, the drive means 208 and the driving device 209 to establish a steady operation of the heating rolls 201.

When the steady operation has been continued for a determined time, the bank 212 over the space between the heating rolls 201 vanishes.

When the bank 212 has vanished, the bank sensor 206 outputs a detection signal to the control means 210 which in turn outputs a drive control signal to the drive means 208 so that the space L between the pair of heating rolls 201 is narrowed by the drive means 208 (Step 10). When the space L between the heating rolls 201 is narrowed, the thickness of the roll-like sheet 213 which has been wound on one of the heating rolls 201 is reduced, resulting in the re-formation of the bank 212 over the space between the heating rolls 201.

The bank sensor 206 watches the bank 212 forming over the space between the heating rolls 201. When the bank sensor 206 detects a bank 212 of less than a predetermined volume, a detection signal is sent to the control means 210 causing the space L between the heating rolls 201 to be fine-adjusted and further reduced (Step 11, Step 10).

When the bank sensor 206 detects a bank 212 of the predetermined volume on the heating rolls 201, the bank sensor outputs a detection signal to the control means 210 so that the control means directs the heating means 207, the drive means 208, and the driving device 209 to keep the heating rolls 201 at constant speeds of rotations and at constant heating temperatures for thereby establishing a steady operation (Step 12).

The control means 210 counts the number of the outputs, from the bank sensors 206, of the detection signals representing formation of the bank 212. When the control means 210 judges that the number is less than a preliminary input number, the control means repeats the Steps 5–7; namely, the control means outputs control signals to the heating means 207, the drive means 208 and the driving device 209 so that the bank 212 between the heating rolls vanishes.

As described, the control means 210 receives various signals from the temperature sensor 203, the rotational condition sensor 204, the position sensor 205 and the bank sensor 206 and repeats a predetermined number of times the formation and vanishing of the bank 212 above the space between the heating rolls 201, according to a predetermined program.

After the formation and vanishing of the bank 212 have been repeated a predetermined number of times, the rotation and heating of the heating rolls 201 are terminated to finish the kneading.

As will be seen from the above description of this embodiment, the control means 210 automatically controls the pair of heating rolls 201 so that particles of a mound-like deposit of powdered material stored on the heating rolls 201 are mixed until the particles are completely or partially melted. Thereafter, the material is kneaded to form a bank 212 on the heating rolls 201. The formation and vanishing of the bank are repeated a predetermined number of times to assure a greatly uniform kneading of the material.

According to the automatic kneading apparatus of the present invention, the control means is operative, based on various detection signals from the temperature sensor, the rotational condition sensor, the position sensor and the bank sensor, to control, in accordance with the condition of a bank formed on the heating rolls, the heating means, the drive means 208 for determining the space between the heating rolls, and the driving device for determining the directions and speeds of rotations of the heating rolls, to attain an optimum condition so that the formation and vanishing of a bank on the heating rolls is repeated a predetermined number of times to assure a uniform kneading of the material.

Figure 25:
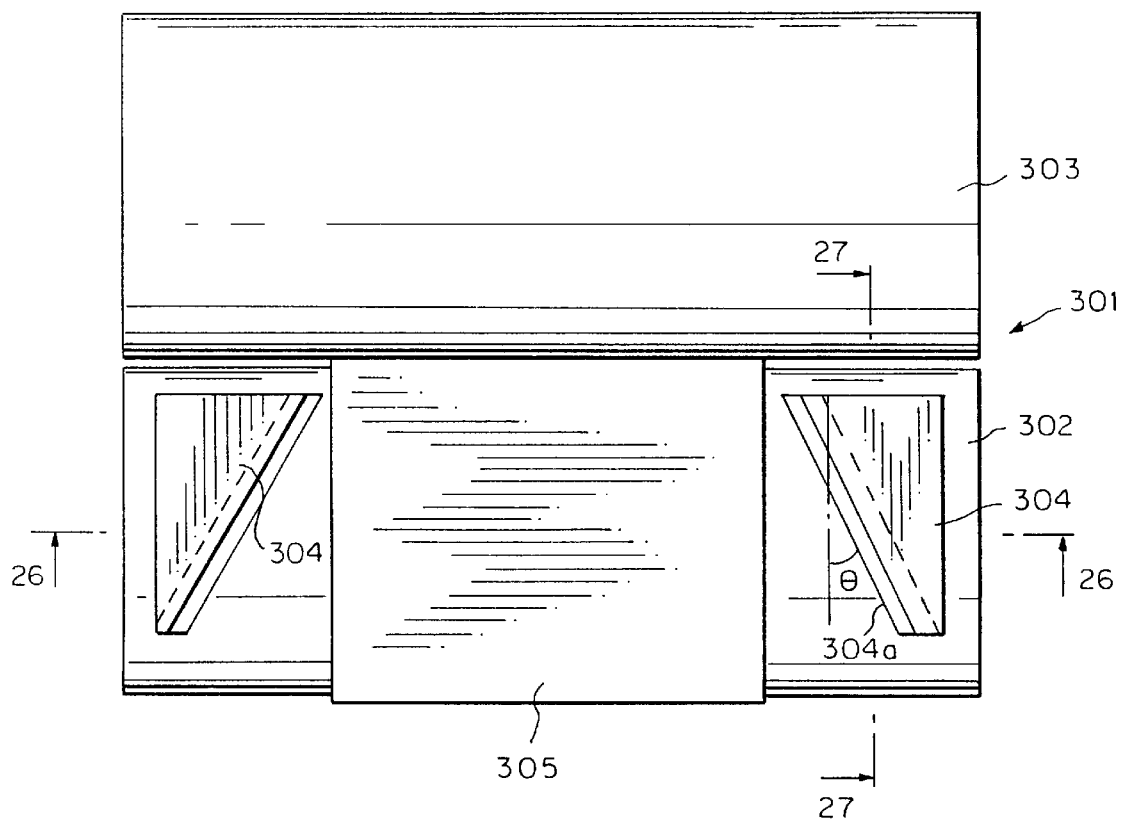
FIG. 25 is a top plan view of a kneading apparatus of an embodiment of the present invention.

FIG. 25 is a schematic illustration of a kneading apparatus in an embodiment of the present invention.

As shown in FIG. 25, the kneading apparatus 301 comprises a sheet winding roll 302, a counter roll 303 disposed in opposed relationship to the sheet winding roll 302 and having an axis parallel to that of the sheet winding roll with a predetermined space defined therebetween, and a pair of blades 304.

The pair of blades 304 have symmetrical or mirror-image shapes and are disposed on the outer surface of the sheet winding roll 302 in opposing positions. They are movable axially along the sheet winding roll by a suitable driver such as a motor. Initially, the pair of blades 304 are positioned on the outer surface of the sheet winding roll 302 outside the width of a rolled sheet 305.

Figure 26:
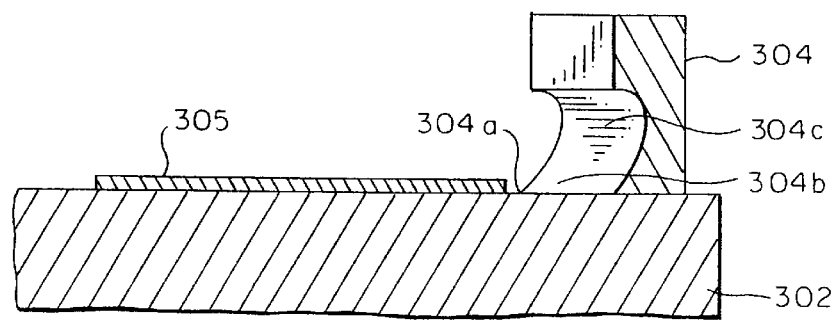
FIG. 26 is a section taken along line 26—26 in FIG. 25.
Figure 27:
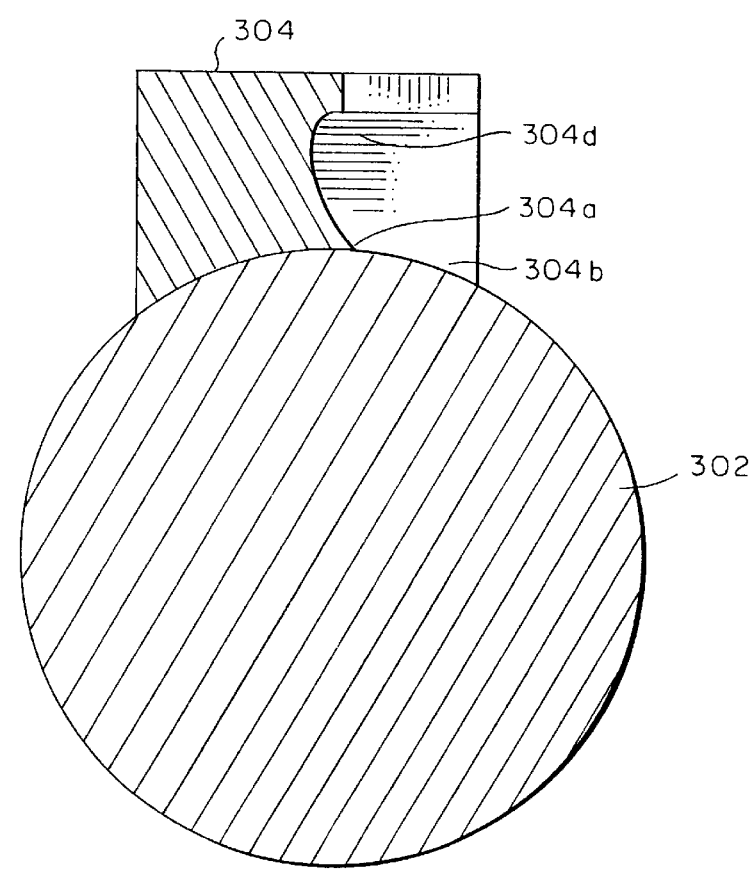
FIG. 27 is a section taken along line 27—27 in FIG. 25.

As shown in FIGS. 26 and 27, each blade 304 is provided with a scooping surface 304b beginning with an edge 304a disposed in contact with the peripheral surface of the sheet winding roll 302 and a laterally guiding surface 304c contiguous with the scooping surface 304b. These surfaces are operative to fold toward the center line of the rolled sheet 305 the part of the rolled sheet 305 peeled by the scooping surface 304b away from the sheet winding roll. A rear guiding surface 304d, as shown in FIG. 27, is continuous with the scooping surface 304b and is operative to fold, in the reverse direction of the movement of the rolled sheet 305, the part of the rolled sheet 305 peeled by the scooping surface 304b away from the sheet winding roll.

As shown in FIG. 25, the edge 304a of the scooping surface 304b of each blade 304 extends obliquely, at an angle theta relative to the circumference about the axis of the sheet-winding roll 302. Since the edge 304a is oblique at an angle theta, when the pair of blades 304 are moved toward each other, the blades are brought into cutting engagement with the rolled sheet 305 formed on the sheet and scoop the cut ends of the rolled sheet 305. The angle defined between the scooping surface 304b of each blade 304 and the peripheral surface of the sheet winding roll 302 should preferably be as sharp as possible. There is no limitation with respect to the radius of curvature of each laterally guiding surface 304c so long as this surface 304c is so curved as to be continuous with the scooping surface 304b, as shown in FIG. 26, and will operate to scoop up an end of the rolled sheet from the sheet-winding roll 302 and fold this end of the rolled sheet toward the center of the rolled sheet, i.e., toward the widthwise center of the rolled sheet 305 on the sheet-winding roll 302. By "fold this end of the rolled sheet toward the center of the rolled sheet", it is meant to say generally not only that the scooped end of the rolled sheet is folded to exactly reach the widthwise center of the rolled sheet 305 but also that the scooped end of the rolled sheet is folded back inwardly of the rolled sheet toward the widthwise center of the rolled sheet. Also, there is no limitation with respect to the radius of curvature of the rear guiding surface 304d so long as this guiding surface is so shaped as to be continuous from the scooping surface 304b, as shown in FIG. 27, and operative to fold backwardly of the direction of rotation of the rolled sheet 305 the end of the rolled sheet scooped up from the sheet-winding roll 302.

The operation of the kneading apparatus 301 is described below.

Initially, the pair of blades 304 are waiting while positioned at a space wider than the width of a rolled sheet 305 which will be wound on the sheet winding roll 302. As an amount of a material such as thermoplastic resin is kneaded by the sheet-winding roll 302 and the counter roll, the thermoplastic resin is formed into a rolled sheet 305 wound on the surface of the sheet-winding roll 302. The rolled sheet 305 as formed has not yet been adjusted in its width, and the widthwise ends of the rolled sheet 305 are of wavy shapes.

Figure 28:
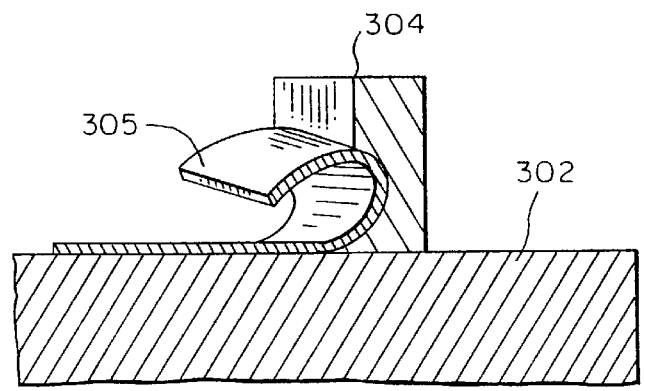
FIG. 28 illustrates in partly sectional view the operation of the present invention.
Figure 29:
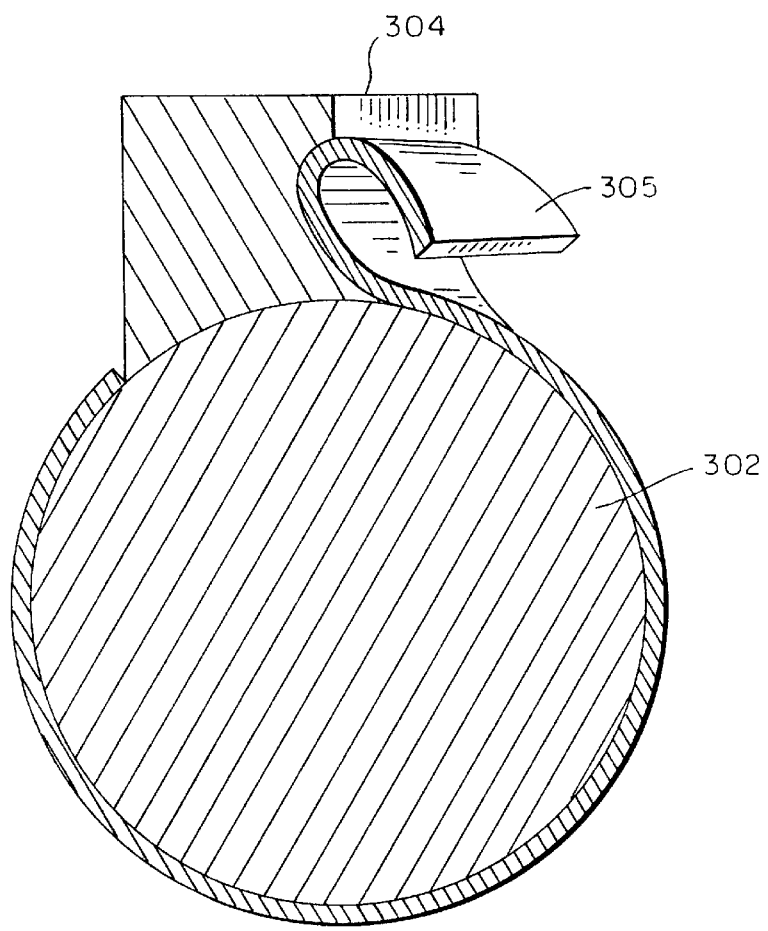
FIG. 29 illustrates in partly sectional view the operation of the present invention.

The pair of blades 304 are moved toward each other. The movements of the blades 304 bring the edges 304a of the scooping surfaces of the blades into cutting engagements with the ends of the rolled sheet 305. The pair of blades 304 are further moved toward each other. When the distance between the pair of blades 304 reaches a predetermined separation, the pair of blades 304 are stopped. In this position, because the sheet winding roll 302 is being rotated, the ends of the rolled sheet 305 are relatively moved toward the scooping surfaces, so that the ends of the rolled sheet 305 are cut and the cut ends of the rolled sheet 305 are scooped up and guided from the scooping surfaces 304b to the laterally guiding surfaces 304c and then folded back inwardly of the rolled sheet 305, as shown in FIG. 28, until the scooped ends of the rolled sheet 305 are folded backwardly of the direction of the rotation of the rolled sheet 305, as shown in FIG. 29.

Figure 30:
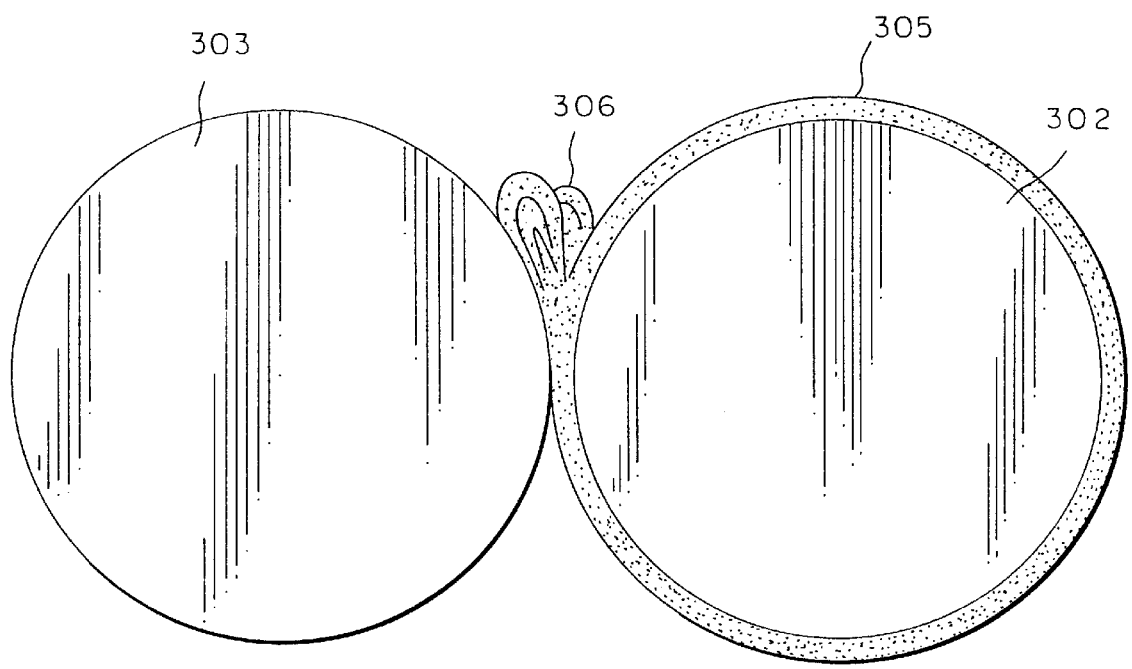
FIG. 30 illustrates in partly sectional view the operation of the present invention.

As a result, the opposite ends of the rolled sheet 305 are scooped up by the pair of blades 304 and the scooped ends are folded backwardly and inwardly of the rolled sheet 305. The folded ends are moved to the gap between the sheet winding roll 302 and the counter roll and are kneaded into the bank 306 present during this operation above the roll gap, as shown in FIG. 30.

The part of the resin which has not been scooped up by the scooping surfaces 304b of the blades 304 is formed into a rolled sheet 305 of a predetermined width rotating with the sheet winding roll 302. In other words, the pair of blades 304 control the width of the rolled sheet 305.

Figure 31:
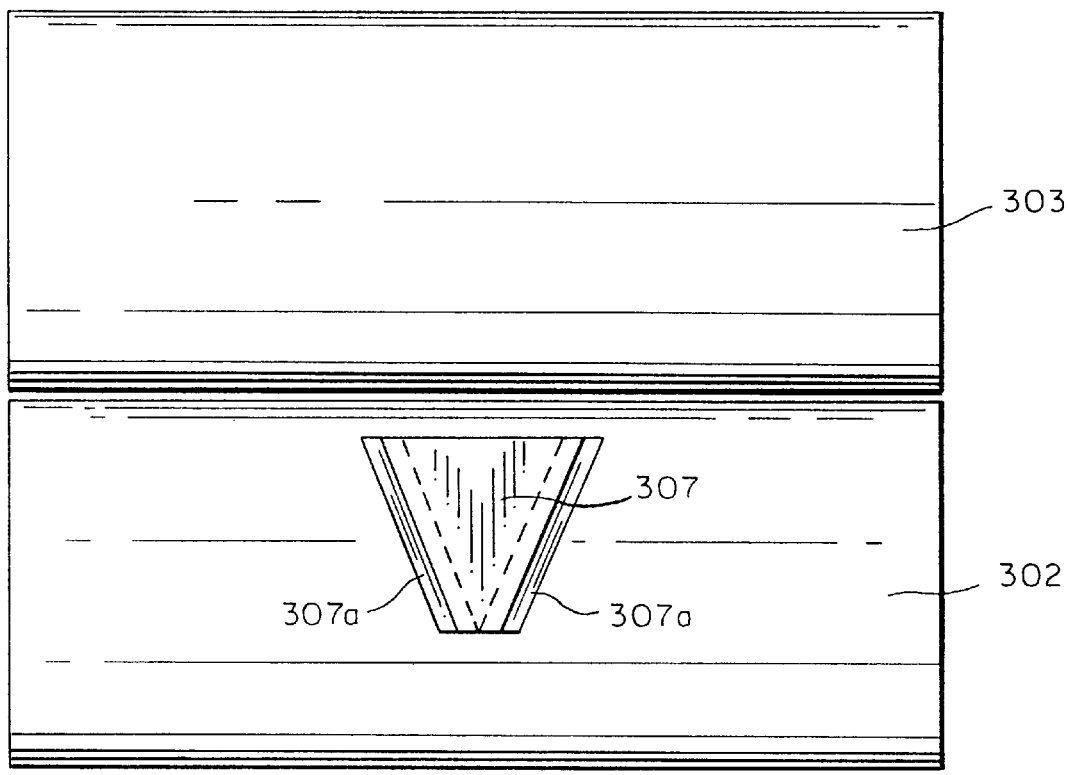
FIG. 31 is a top plan view of a kneading apparatus of an embodiment of the present invention.

FIG. 31 shows the outline of a second kneading apparatus of an embodiment of the present invention.

Figure 32:
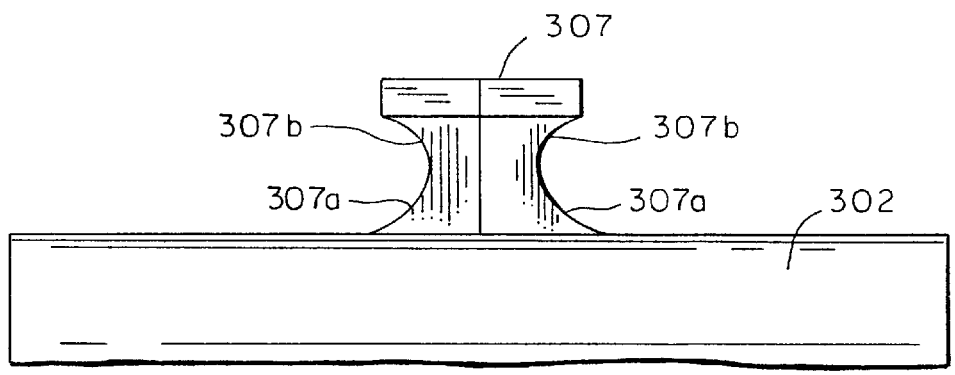
FIG. 32 is a front view of the kneading apparatus of an embodiment of the present invention.

As shown in FIG. 31, this kneading apparatus has a single blade 307 disposed on a sheet-winding roll 302. As shown in FIGS. 31 and 32, the blade 307 has scooping surfaces 307a operative to peel a rolled sheet 302 away from the sheet winding roll 302, rear guiding surfaces (corresponding to the surface shown at 304d in FIG. 27) for guiding the peeled roll sheet in such a manner as to fold the peeled sheet backwardly of the movement of the rolled sheet caused by the rotation of the sheet-winding roll, and laterally guiding surfaces 307b for guiding the peeled rolled sheet in such a manner as to fold the peeled sheet toward the opposite ends of the rolled sheet by the rotation of the sheet winding roll 302.

The blade 307 shown in FIG. 31 is operative to tear the central portion of a rolled sheet wound on the sheet winding roll 302, peel the thus torn portions of the sheet away from the roll surface and fold the thus-peeled portions of the sheet backwardly of the movement of the rolled sheet as well as toward the opposite ends of the rolled sheet.

Figure 48:
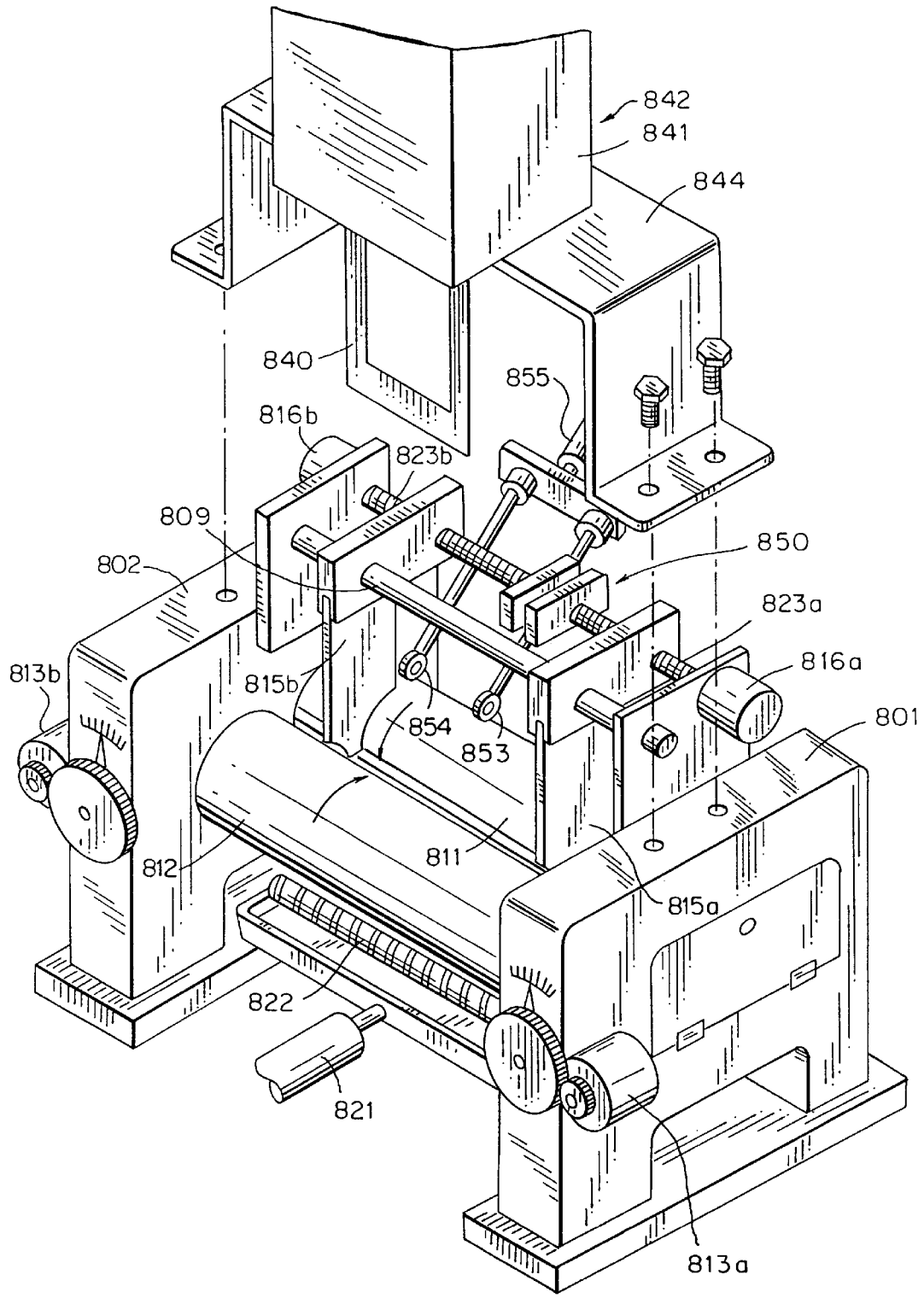
FIG. 48 is a schematic perspective view of another embodiment of the sheet testing sample making apparatus of the present invention.

This second kneading apparatus should preferably be provided with such blades as the ones 815a and 815b shown in FIG. 48 so as to regulate or limit the width of the rolled sheet wound on the peripheral surface of the sheet winding roll 302.

When sheet material is kneaded in the gap between the sheet winding roll and the counter roll and a bank of the material is formed, the opposite ends of a rolled sheet formed on the sheet-winding roll are scooped up and these scooped sheet ends are folded backwardly of the rotation of the rolled sheet as well as toward the opposite ends of the rolled sheet to form a complicated mass of folded sheet which is then moved to the bank and mixed and kneaded therewith. Accordingly, this embodiment of the present invention provides a kneading apparatus which provides a superior kneading effect and, at the same time, is operative to control the width of a rolled sheet formed on the sheet winding roll.

Figure 33:
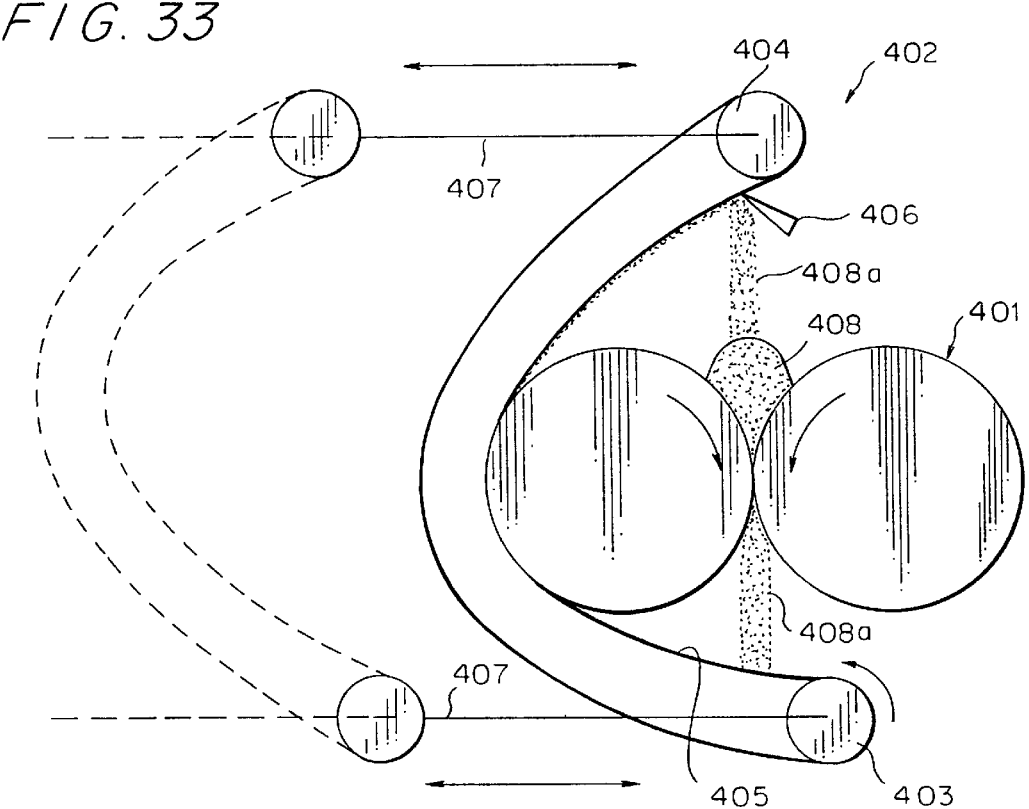
FIG. 33 is a schematic illustration of an embodiment of the present invention.

FIG. 33 shows a third embodiment of the kneading apparatus of the present invention.

As shown in FIG. 33, the kneading apparatus comprises a pair of heating rolls 401 and fallen material returning means 402.

The pair of heating rolls 401 are arranged in opposed relationship with their axes extending in parallel and a predetermined gap defined between the rolls. The pair of heating rolls 401 can be rotated by a driver, not shown, at predetermined speeds and in predetermined directions. The gap between the pair of heating rolls 401 can be freely adjusted by a gap adjustment means, not shown. In addition, the heating rolls 401 can be heated to predetermined temperatures by a heating means, not shown.

The fallen material returning means 402 comprises a driven pulley 403 disposed below the gap between the heating rolls 401, a driving pulley 404 disposed above the gap between the heating rolls 401, an endless belt 405 extending around the driving and driven pulleys 404 and 403, and a scraper 406 for scraping a deposit adhered to the endless belt 405, the scraper being disposed adjacent the driving pulley 404 and so arranged that the belt 405 is faced to the gap between the heating rolls 401. Other preferred modes of the fallen material returning means are described below.

The driving pulley 404 and the pulley roll 403 are supported on rods 407 movable forwardly and rearwardly by suitable means such as a piston (not shown) and are horizontally movable by the forward and rearward movements of the rods 407. When the fallen material returning means is in operation, the forward movements of the rods 407 bring the belt 405 into contact with one of the heating rolls 401. When the rods 407 are rearwardly moved, the fallen material returning means in its entirety is moved away from the heating rolls 401 to a retracted position.

According to the apparatus of this embodiment, when an amount of powdered material 408a is first fed into the gap between the pair of heating rolls 401, a part of the material 408a drops through the gap. The dropped powdered material 408a is received on the belt 405 positioned below the gap between the heating rolls 401. Because this belt 405 is caused to run by the driving pulley 404 along an endless track, the powdered material 408a received on the belt 405 is carried by the belt 405. Because the surface of the powdered material 408a on the belt 405 has been softened or melted by the heating rolls 401, the powdered material is adhered to the surface of the belt 405. The powdered material 408a adhered to the surface of the belt 405 is transferred by the belt 405 toward the driving pulley 404. Because the scraper 406 is disposed adjacent the driving pulley 404, the scraper 406 scrapes the powdered material 408a adhering to and transferred by the belt 405. The thus scraped material falls onto the gap between the heating rolls 401 and is kneaded by the heating rolls 401.

As the kneading proceeds as above, the powdered material 408a comes to be in a partly or fully melted state, with a result that the kneaded material hangs down through the gap between the heating rolls 401 to form a sheet.

After the forward end of the sheet material hanging through the gap has reached the belt 405 disposed below the gap between the heating rolls 401, the sheet material further hangs downwardly until the leading end portion of the sheet material is adhered to and transferred by the rotation of the belt 405.

The thus transferred sheet material is scraped by the scraper 406, so that the leading end portion of the sheet material is dropped onto the gap between the heating rolls 401. Because the heating rolls 401 are being rotated, the dropped sheet portion is immediately wound on one of the heating rolls 401 even if the sheet material which hangs through the gap and is transferred by the belt 405 to the gap is slack. Thus, the kneading is carried out for a predetermined time in such a manner that the outer periphery of the heating roll 401 is wound with a rolled sheet and a bank of the material is formed in the gap between the pair of heating rolls 401.

As described above, the apparatus of this embodiment is operative to return to the gap between the heating rolls 401 the powdered material which falls through the gap between the heating rolls in the initial stage of the kneading operation, to thereby avoid any waste of the powdered material. At the same time, the apparatus is also operative, without requiring any human operation, to wind on a heating roll a sheet falling down through the gap between the heating rolls 401.

The fallen material returning means 402 of the apparatus of the described embodiment has the driving and driven pulleys 404 and 403. However, in the case where the belt 405 is engaged with a heating roll 401 and driven by the rotation of the heating roll 401, the fallen material returning means does not require any extra driving pulley and, instead, may have a pair of driven pulleys.

It is not essential that the fallen material returning means 402 has the belt 405 so long as the fallen material returning means is operative to return to the gap between the heating rolls 401 the powdered material 408 which falls through the gap between the heating rolls 401. For example, the fallen material returning means may be of a structure having buckets or cups circulated along an endless track.

Figure 34:
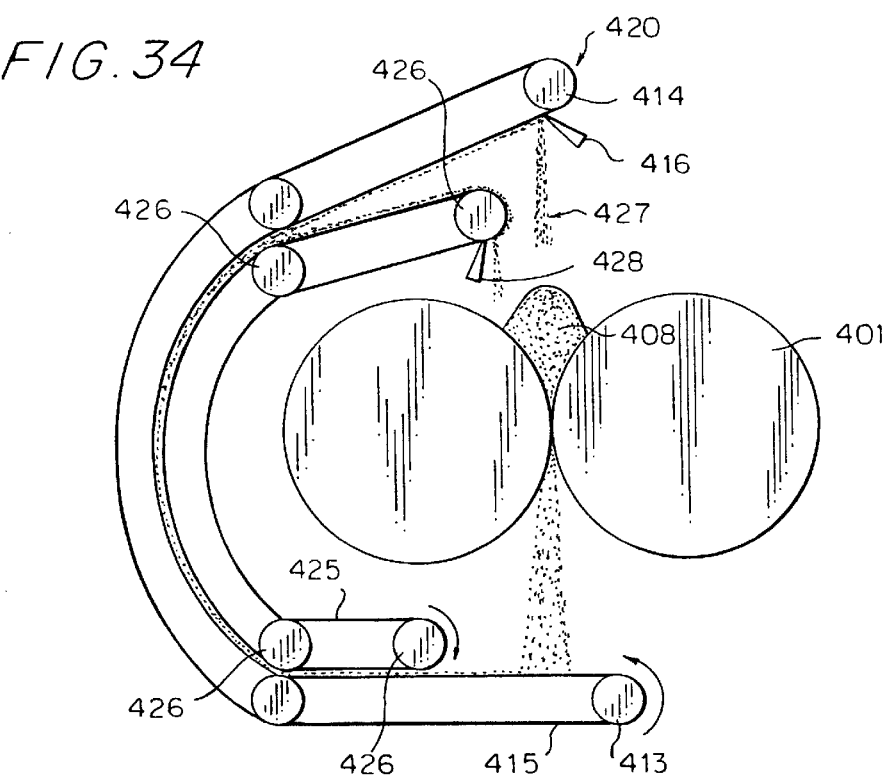
FIG. 34 is a schematic illustration of another embodiment of the present invention.

FIG. 34 shows another embodiment of the invention.

As shown in FIG. 34, a kneading apparatus comprises a pair of heating rolls 401; a first transferring section 420 having a driven pulley 413 disposed below the gap between the heating rolls 401, a driving pulley 414 disposed above the gap between the heating rolls 401 and an endless belt 415 extending around the driving and driven pulleys 414 and 413; a second transferring section 427 having an endless belt 425 facing the endless belt 415 of the first transferring section 420 and rolls 426 around which the endless belt 425 extends; a first scraper 416 disposed in sliding engagement with the belt 415 of the first transferring section 420; and a second scraper 428 disposed in sliding engagement with the belt 425 of the second transferring section 427.

In the apparatus of the described embodiment, when the powdered material 408 falls through the gap between the heating rolls 401 onto the belt 415 of the first transferring section 420, the powdered material 408 on the belt 415 of the first transferring section 420 is transferred by the belt and then sandwiched between the belt 415 of the first transferring section 420 and the belt 425 of the second transferring section 427 and carried by the belts. The powdered material 408 carried between the belts 415 and 425 of the first and second transferring sections 420 and 427 is scraped by the first scraper 416 onto the gap between the heating rolls 401. The powdered material 408 adhered to the belt 525 of the second transferring section 427 is scraped by the second scraper 428 into the gap between the heating rolls 401.

Figure 35:
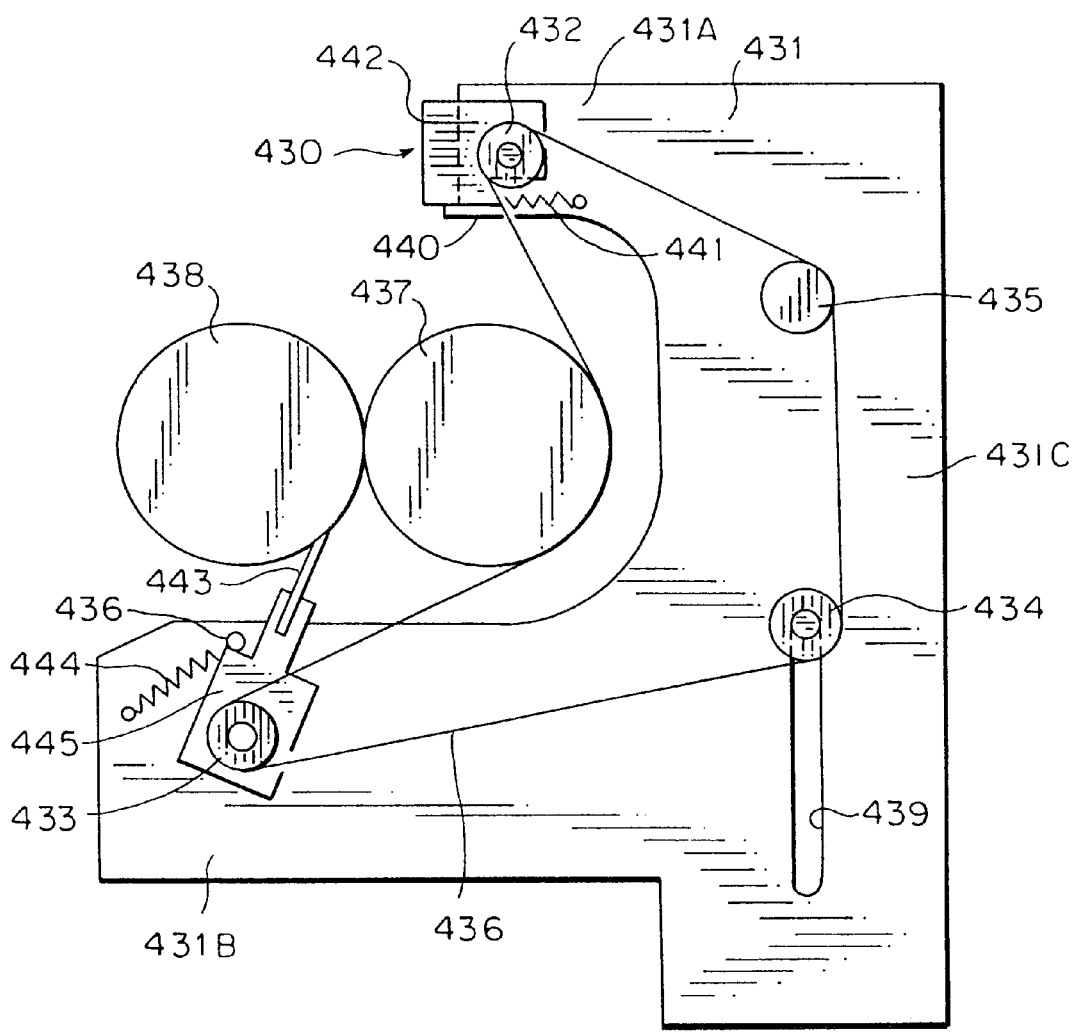
FIG. 35 illustrates an embodiment of a fallen material-returning apparatus of the present invention.
Figure 36:
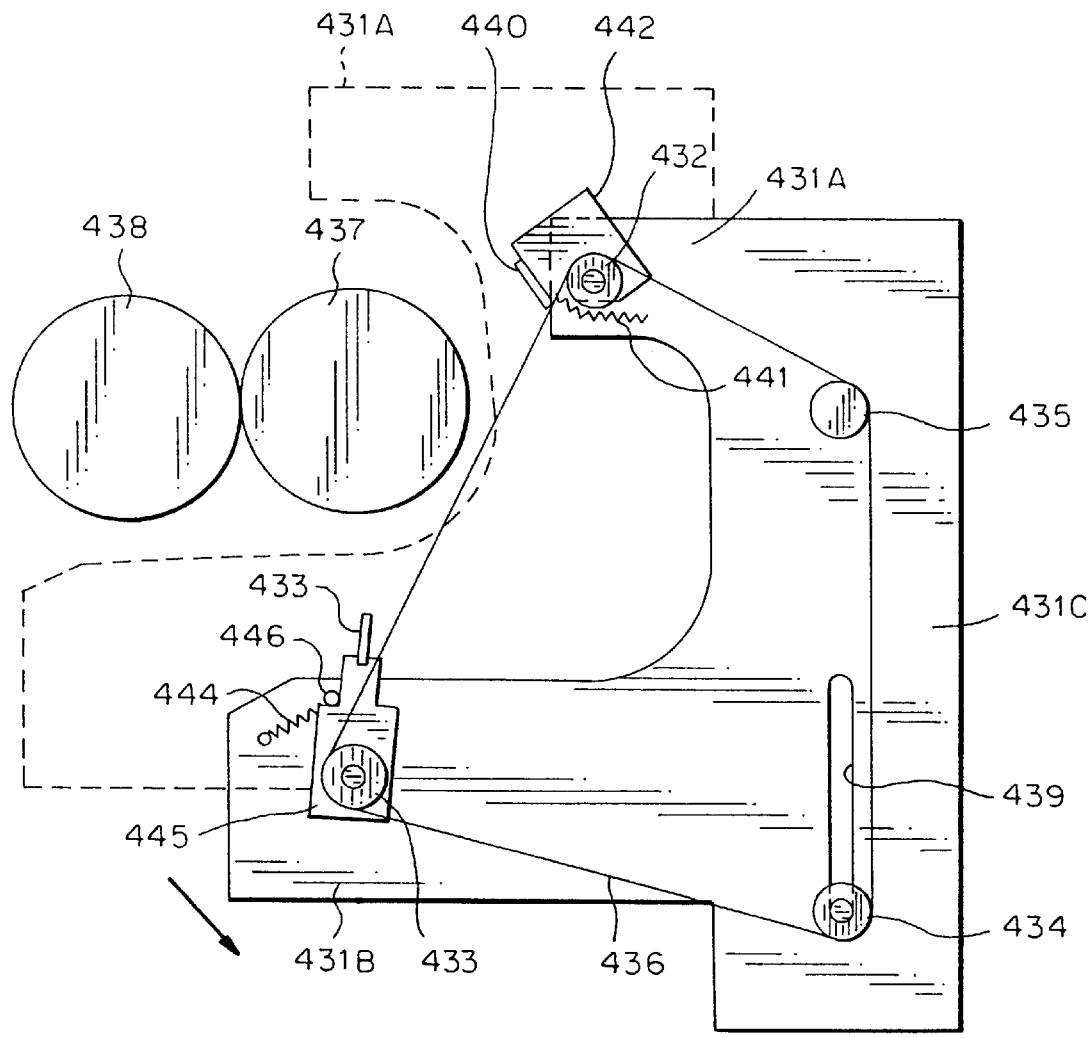
FIG. 36 illustrates an embodiment of the fallen material returning apparatus of the present invention.

FIGS. 35 and 36 show another preferred embodiment of the fallen material returning apparatus of the present invention.

As shown in FIG. 35, the fallen material returning apparatus 430 comprises a pair of supporting bases 431, a first driven roll 432, a second driven roll 433, a third driven roll 434, a fourth driven roll 435, an endless belt 436 and means (not shown) for driving the supporting bases.

The pair of supporting bases 431 are disposed in parallel relationship and spaced a distance equal to the axial dimension of a pair of heating rolls 437 and 438.

The pair of supporting bases 431 comprises first supporting portion 431A disposed above one 437 of the pair of heating rolls 437 and 438, i.e., the heating roll 437 disposed adjacent the supporting bases 431, when the fallen material returning apparatus 430 is in operation; second supporting portions 431B extending to the other 438 of the pair of heating rolls 437 and 438 and disposed below the pair of heating rolls 437 and 438; and third supporting portion 431C connected to and supporting the first and second supporting portions 431A and 431B.

The pair of supporting bases 431 have symmetrical shapes. Between the pair of first supporting portions 431A is rotatably supported the first driven roll 432.

Between the pair of second supporting portions 431B is rotatably supported the second driven roll. Each of the third supporting portions 431C has formed therein a slot 439 of a predetermined length extending in the vertical direction. The third driven roll 434 is rotatably supported in the slots 439 in the pair of supporting sections 431C and freely movable along the slots 439. The pair of third supporting portions 431C rotatably support the fourth driven roll 435 disposed above the slots 439.

The endless belt 436 extends around the first, second, third and fourth driven rolls 432, 433, 434 and 435.

On the pivot shaft of the first driven roll 432 at the first supporting portions 431A is rotatably mounted a first rotary plate 442 which supports a first doctor blade 440 in sliding contact with the endless belt 436 and is so biased by a first biasing member 441, such as a coil spring, as to always urge the edge of the first doctor blade 440 against the endless belt 436.

On the pivot shaft of the second driven roll 433 at the second supporting portions is rotatably mounted a second rotary plate 445 which supports a second doctor blade 443 in sliding contact with the peripheral surface of the other heating roll 438 which is not engaged with the endless belt 436, the rotary plate 445 being so biased by a second biasing member 444, such as a coil spring, as to always urge the edge of the second doctor blade 443 against the peripheral surface of the heating roll 438.

The pair of supporting bases 431, the first driven roll 432, the second driven roll 433, the third driven roll 434, the fourth driven roll 435, the endless belt 436, the first rotary plate 442 and the second rotary plate 445 cooperate together to form an assembly which is movable forwardly by a base driving means (not shown) into a position in which the endless belt 436 is engaged with and extends around a predetermined part of the peripheral surface of the one heating roll 437. The assembly is also movable rearwardly by the base driving means to a position in which the endless belt 436 is disengaged from the one heating roll 437.

The operation of the fallen material returning apparatus 430 is described hereinunder.

The initial position of the fallen material returning apparatus 430 is shown in FIG. 36.

In FIG. 36, the third driven roll 434 is positioned by gravity in the lower ends of the slots 439, so that the endless belt 436 extends around the first driven roll 432, the second driven roll 433, the third driven roll 434 and the fourth driven roll 435 and the endless belt is not slack. The portion of the endless belt 436 which extends between the first driven roll 432 and the second driven roll 433 is positioned a distance away from the heating roll 437. In this position, the first rotary plate 442, which supports the first doctor blade 440 in sliding contact with the endless belt 436, is rotated against the first biasing member 441 by the endless belt 436 tensioned between the first driven roll 432 and the second driven roll 433, as will be seen in FIG. 36. The second rotary plate 445 is rotated by the second biasing member 444 to a stop pin 446 which limits the rotational movement of the rotary plate 445.

In the case where the pair of heating rolls 437 and 438 are operated to knead an amount of powdered vinyl chloride resin so as to form a film or sheet of the vinyl chloride resin, the supporting bases 431 are moved by the base driving means toward the pair of heating rolls 437 and 438 disposed in opposed relationship with a predetermined gap defined therebetween.

As the supporting bases 431 are moved forwardly, the part of the endless belt 436 extending between the first driven roll 432 and the second driven roll 433 is moved into contact with the peripheral surface of the heating roll 437. As the supporting bases 431 are further moved forwardly, the part of the endless belt 436 takes a position to surround a predetermined length of the periphery of the one heating roll 437. When the part of the endless belt 436 which extended initially linearly between the first driven roll 432 and the second driven roll 433 is wound around the one heating roll, the initial tangential length of the endless belt 436 between the first driven roll 432 and the second driven roll 433 is now required to have an additional part of the length of the endless belt 436. The length of the other part of the endless belt 436 must therefore be reduced to comply with this requirement for such an additional length. Accordingly, the third driven roll 434 is lifted along the slots 439 so that the parts of the endless belt 436 extending between the first driven roll 432 and the forth driven roll 435, between the second driven roll 433 and the third driven roll 434 and between the third driven roll 434 and the fourth driven roll 435 may take a straight position, and is then stopped at a predetermined position.

When the endless belt 436 takes a position in which the belt extends around a predetermined length of the peripheral surface of the one heating roll 437, the forward movement of the supporting bases 431 is stopped.

At this stage of the operation, the first rotary plate 442 has already been rotated and the edge of the first doctor blade 440 is urged by the first biasing member 441 into sliding engagement with the part of the endless belt 436. The second rotary plate 445 has also been already rotated against the biasing force of the second biasing member 444. In the position in which the forward movement of the supporting bases 431 is stopped, the edge of the second doctor blade 443 is urged by the biasing force of the second biasing member 444 into sliding engagement with the peripheral surface of the other heating roll 438.

Then, when the powdered resin is fed to the nip between the pair of rotating heating rolls 437 and 438, a part of the thus fed powdered resin falls through a small gap between the pair of heating rolls 437 and 438, while another part of the powdered resin is adhered to the peripheral surface of the other heating roll 438 which is not surrounded by the endless belt 436.

The part of the powdered resin adhered to the peripheral surface of the other heating roll 438 is moved with the rotation of the other heating roll 438 and then scraped by the second doctor blade 433 away from the peripheral surface of the other heating roll 438 onto the upper surface of the part of the endless belt 436 extending between the second driven roll 433 and the one heating roll 437. The part of the powdered resin which has fallen through the gap between the pair of heating rolls 437 and 438 is dropped onto the upper surface of the part of the endless belt which extends between the second driven roll 433 and the peripheral surface of the one heating roll 437. These parts of the powdered resin which have been scraped and dropped onto said part of the endless belt 436 are conveyed toward the first driven roll 432 by the endless belt 436 driven by the rotation of the heating rolls. A part of the powdered resin which is conveyed by the endless belt 436 is adhered to the heating roll at the point where the endless belt 436 is separated from the heating roll, while the other part of the powdered resin is adhered to and conveyed by the endless belt toward the first driven roll 432. The part of the powdered resin conveyed toward the first driven roll 432 is scraped by the first doctor blade 440 away from the endless belt 436 onto the gap between the pair of heating rolls 437 and 438.

In the described manner, the parts of the powdered resin dropped through the gap between the pair of heating rolls 437 and 438 and adhered to the other heating roll 438 are carried by the endless belt 436 and returned to the gap between the pair of heating rolls 437 and 438.

When a film or sheet of resin begins to be wound on the one heating roll 437 by the kneading of the powdered resin by the pair of heating rolls 437 and 438, a part of the film or sheet of the resin may be dropped through or suspended from the gap between the pair of heating rolls 437 and 438. Such a part of the film or sheet of the resin is also similarly returned by the endless belt 436 to the upper surfaces of the pair of heating rolls 437 and 438.

The fallen material returning apparatus 430 can automatically return to the nip between the pair of heating rolls the powdered resin dropped through the gap between the heating rolls and does not require any manual fallen material-returning operation of an operator.

Accordingly, the present invention provides a kneading apparatus which is operative to easily and reliably return to the gap between the heating rolls the material falling through the gap between the heating rolls and which does not require any manual assistance for the fallen material-returning operation.

Figure 37:
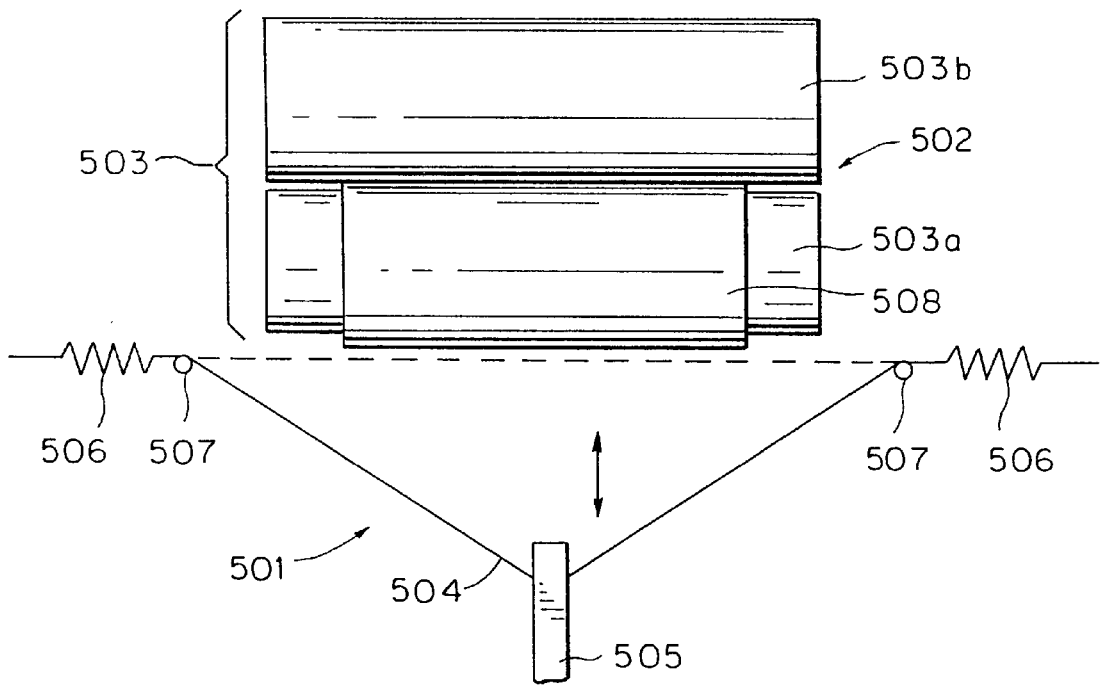
FIG. 37 is a schematic illustration of a rolled sheet cutting apparatus of an embodiment of the present invention.

FIG. 37 is a diagrammatic illustration of an embodiment of the present invention.

As shown in FIG. 37, a roll sheet cutting device 501 is incorporated in a kneading roll device 502.

The kneading roll device 502 comprises a pair of heating rolls 503 one of which is a sheet-winding roll 503a capable of taking a sheet material up on the peripheral surface thereof. The other heating roll is a counter roll 503b disposed in opposed relationship with the sheet-winding roll 503a with the axis of the rolls extending in parallel relationship.

The roll sheet cutting device 502 has a wire 504 and an engagement means 505.

The wire 504 is disposed in parallel relationship with the axis of the sheet winding roll 503a and spaced a predetermined distance from the peripheral surface of the sheet winding roll 503a. In this embodiment, the wire 504 has its opposite ends respectively connected with biasing means such as, for example, springs. Position control pins 507 are disposed in engagement with the wire 504 adjacent the opposite ends thereof.

The material and dimension of the wire 504 may be suitably determined so long as the wire achieves the object of the invention. More specifically, a length of high strength music wire may preferably be used to form the wire 504.

Figure 38:
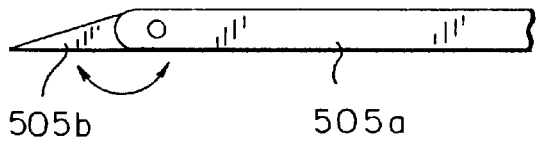
FIG. 38 is a schematic illustration of an engagement means in the rolled sheet cutting apparatus of an embodiment of the invention.

The engagement means 505 may be of any mechanism so long as it is operative to positively move the part of the wire 504 extending between the position control pins 507 away from the sheet-winding roll 503a and then release the wire part. In the illustrated embodiment of the invention, the engagement means 505 is of a mechanism comprising a stem 505a movable toward and away from the sheet winding roll 503a and upwardly and downwardly and a pawl member 505b pivotally provided on the forward end of the stem 505a, as shown in FIG. 38. In the position of the engagement means 505 shown in FIG. 37, the stem 505a having the pawl member 505b at the forward end thereof, as shown in FIG. 38, is initially retracted from the sheet-winding roll 503 with the stem 505a bent at right angles relative to the stem 505a. The engagement means 505 is structured such that, when it is required to engage the part of the wire 504 between the position control pins 507, the stem 505a is moved forwardly until the pawl member 505b engages with the wire 504 and, then the stem 505a is moved away from the sheet-winding roll 503a with the pawl member engaged with the wire 504, as shown in FIG. 39, and, thereafter, the pawl member 505b is swung to disengage the wire 504 from the pawl member 505b.

The roll sheet cutting device 501 is provided with a wire cleaning means for cleaning the wire 504 between the position control pins 507, although the wire cleaning means is not shown in the drawings. The wire cleaning means may be of any mechanism operative to remove dirt from the wire 504. For example, the wire cleaning means may comprise a pair of cleaning pads vertically movable to pinch the wire 504 and a pad driving means operative to horizontally move the pads along the wire 504 while the wire is pinched by the pads.

Then, the operation of this embodiment is described hereunder.

A roll-shaped sheet 508 is wound on the peripheral surface of the sheet winding roll 503a. The wire 504 is disposed to extend in parallel with the axis of the sheet winding roll 503a with a predetermined clearance left between the wire and the peripheral surface of the sheet winding roll 503a. The opposite ends of the wire 504 are pulled by biasing members. The engagement means 505 is in its retracted position.

In the mentioned position of the apparatus, when the sheet 508 on the sheet-winding roll 503a is to be cut, the engagement means 505 is first moved toward the sheet winding roll 503a. The pawl member 505b at the forward end of the stem 505a of the engagement means 505 extends downwardly from the stem 505a at right angles, for example, with respect to the stem. When the forward end of the stem 505a approaches the sheet winding roll 503a sufficiently, the forward end of the stem 505a is lowered to cause the pawl member 505b to be engaged with the wire 504. The stem 505a is then retracted away from the sheet winding roll 503a with the pawl member 505b engaged with the wire 504. When the stem 505a is retracted to a predetermined position, the pawl member 505b is rotated to release the wire 504. Because the wire 504 is tensioned by the biasing members 506, the rotation of the pawl member 505b allows the wire 504 to be sprung toward the sheet-winding roll 503a with the wire 504 not slackened until the spring wire collides with the sheet on the sheet-winding roll 503a and is immediately and speedily moved through the thickness of the sheet to the surface of the sheet-winding roll 503a and then stopped thereby, as shown in FIG. 40, with a result that the sheet 508 on the sheet-winding roll 503a is severed, as shown in FIG. 41.

Immediately after the sheet 508 is severed, the wire 504 is returned by the forces of the biasing members 506 to the initial position adjacent the sheet winding roll 503a. Then, the not shown cleaning means for the wire 504 removes residuals of the sheet from the wire.

Figure 41:
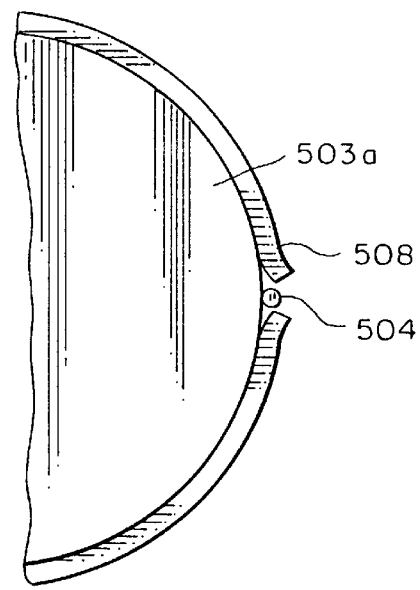
FIG. 41 is a schematic illustration of a sheet on a sheet-winding roll which sheet has just been cut by a wire of the rolled sheet cutting apparatus shown in FIG. 37.

The wire 504 is shown in FIG. 41 circular cross-section. In the present invention, however, there is no limitation in respect of the cross-sectional configuration of the wire 504 so long as the wire can sever the sheet and various cross-sectional configurations, such as triangular cross-section, diamond cross-section and oval cross-section, may be employed optionally.

Figure 42:
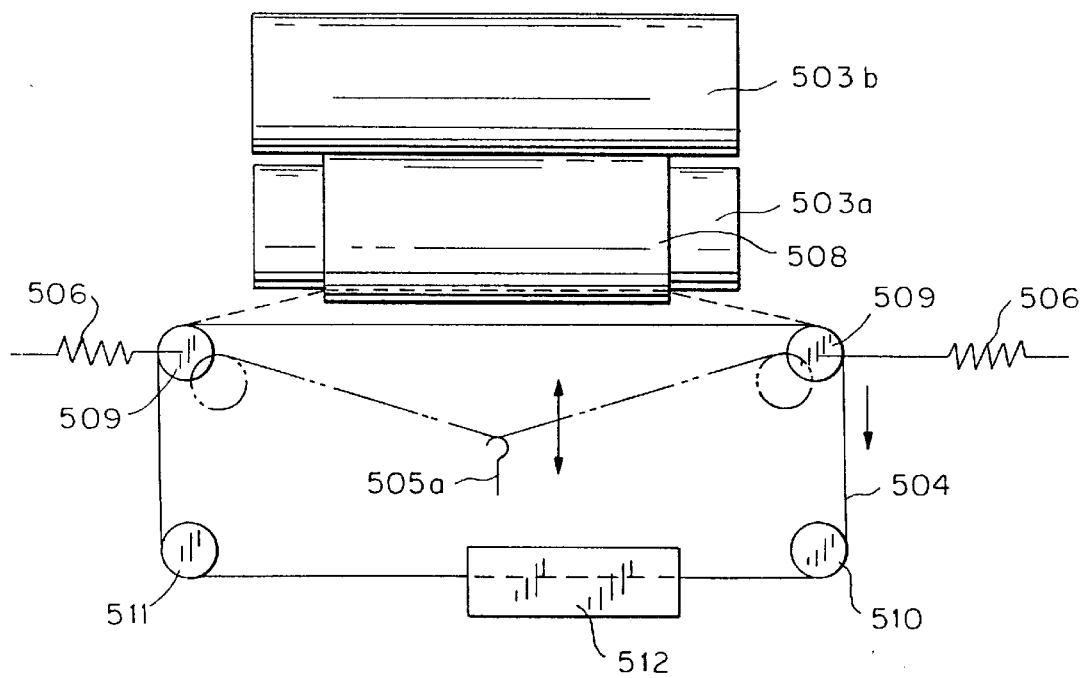
FIG. 42 is a schematic illustration of a rolled sheet cutting apparatus of another embodiment of the present invention.

For example, a modification may comprise a rolled sheet cutting device 501 of a structure shown in FIG. 42.

The rolled sheet-cutting device 501 shown in FIG. 42 comprises a pair of rotatable driven pulleys 509 biased by biasing members 506, a guide pulley 510, a driving pulley 511, an endless wire 504 extending around the driven pulleys 509, the guide pulley 510 and the driving pulley 511, an engagement means 505a, and wire cleaning means 512, all of which are disposed in a plane adjacent a sheet winding roll 503a.

The pair of driven pulleys 509 are arranged along a direction parallel to the axis of the sheet-winding roll 503a and suitably disposed at a space greater than the distance between the opposite ends of a sheet 508 on the sheet-winding roll 503a such that the part of the wire 504 between the driven pulleys 509 extends parallel to the axis of the sheet-winding roll 503a and at a predetermined distance from the surface of the sheet winding roll 503a.

The wire cleaning means 512 comprises a pair of cleaning pads (not shown) for pinching the wire 504, the cleaning pads being fixed with the wire 504 pinched thereby.

The engagement means 505a may be of the mechanism shown in FIG. 38 referred to above or comprise a hook which is movable upwardly, downwardly, forwardly and backwardly.

In the rolled sheet cutting device 501 shown in FIG. 42, the wire 504 is initially positioned at rest by the pair of driven pulleys 509 at a position adjacent the sheet winding roll 503a. When the sheet 508 is to be severed, the engagement means 505a engages with the wire 504 between the driven pulleys 509 and is retracted away from the sheet winding roll 503a with the wire kept engaged with the engagement means 505a. Thus, the wire 504 is pulled. As the wire is pulled, the driven pulleys 509 are appropriately rotated. Because the driven pulleys 509 are connected with the biasing members 506, the tension in the wire 504 is increased as the wire is pulled by the engagement means 505a.

When the engagement means 505a is retracted to a predetermined position, the wire 504 is disengaged from the engagement means 505a.

Because a large tension is being applied to the wire by the biasing members 506, the thus released wire 504 is sprung toward the sheet 508 on the sheet-winding roll 503a and immediately severs the sheet 508 on the sheet winding roll 503a and, thereafter, is returned to the initial position, as in the embodiment shown in FIGS. 37–41. When the wire 504 is returned to the initial position, the driving pulley 511 is rotated to move a part of the wire 504 which part is of a length at least equal to the width of the sheet on the sheet-winding roll 503a. This movement of the wire 504 places, adjacent the sheet on the sheet-winding roll 503a, a fresh part of the wire which is not spoiled by the sheet 508. The part of the wire 504 spoiled by the severed sheet is cleaned by the wire cleaning means 512.

According to the sheet cutting device of the present invention, the sheet can be severed automatically and without any manual operation in such a manner that no damage is caused to the surface of the sheet winding roll and the cut ends of the severed sheet present precisely linear surfaces.

The sheet wound on the sheet winding roll 503a and severed by the wire 504 is pinched in, for example, its cut end by a clamp or clip and peeled away from the peripheral surface of the sheet winding roll 503a at a speed the same as the speed of rotation of the sheet winding roll 503a and then is applied to the frame. As a result, a sheet testing sample is obtained.

Figure 43:
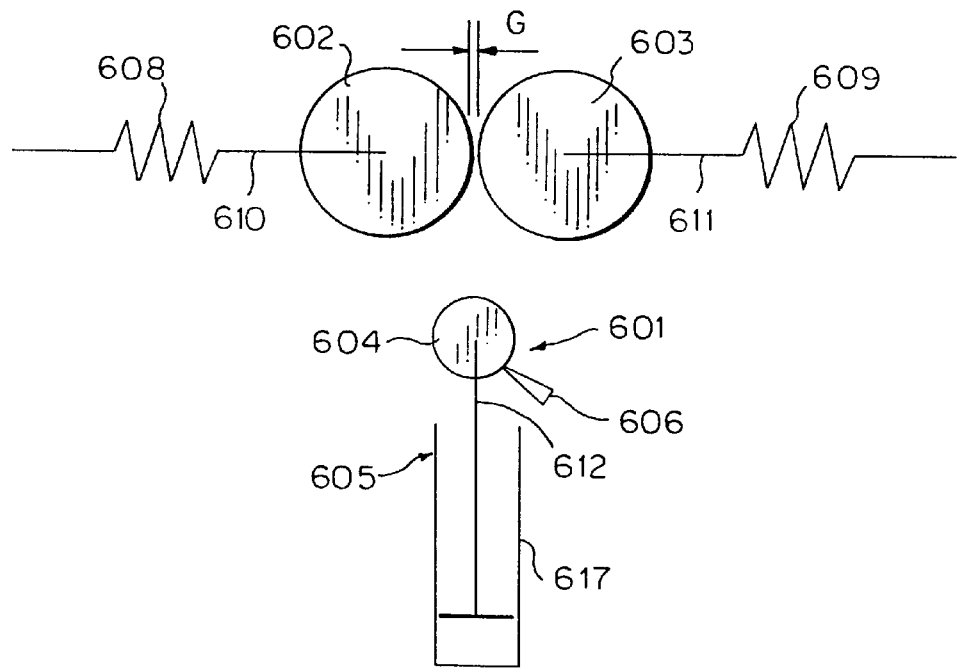
FIG. 43 is a schematic illustration of an arrangement of an apparatus of an embodiment of the invention.

A heating roll cleaning device 601 shown in FIG. 43 is disposed under a pair of heating rolls 602 and 603 arranged in a parallel relationship to define therebetween a gap G of 0.2 mm for kneading a plastic resin to make a kneaded product.

The heating roll cleaning device 601 comprises a cleaning roll 604 adapted to clean the pair of heating rolls 602 and 603 and made of a material the same as said plastic resin and having a surface of a hardness lower (softer) than that of the heating rolls 602 and 603, a cleaning roll displacing means 605 disposed beneath the nip between the heating rolls 602 and 603 and operative to bring the cleaning roll 604 into sliding engagement with the surfaces of the heating rolls 602 and 603, and a scraper 606 for removing dirt from the surface of the cleaning roll 604.

Figure 44:
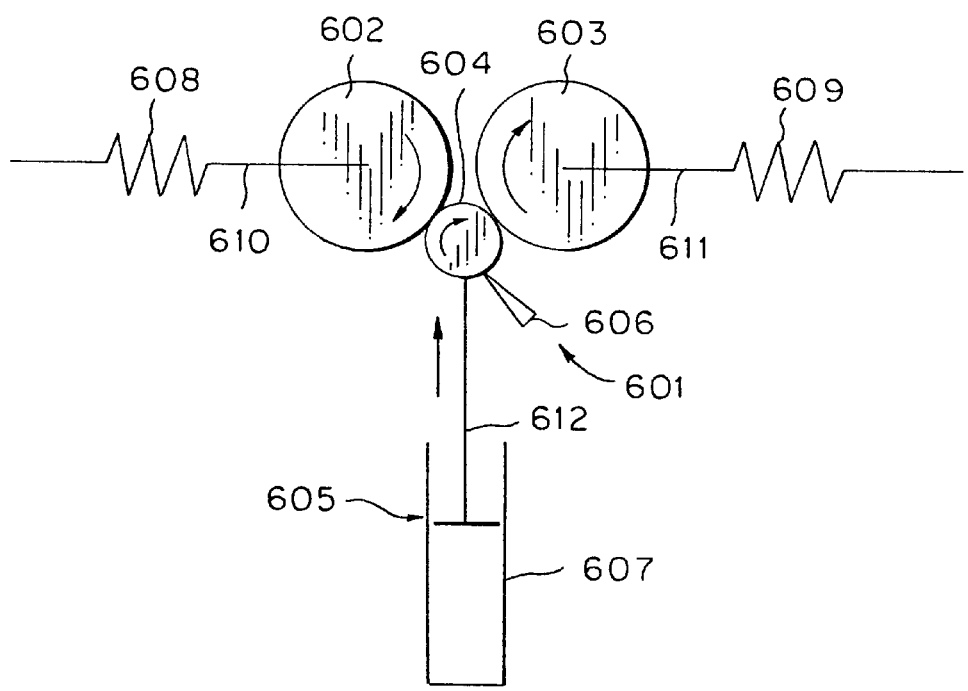
FIG. 44 is a schematic illustration of the operation of the embodiment of the apparatus of the invention.

The heating rolls 602 and 603 are adapted to be driven by different driving means, not shown, at different speeds and in directions indicated by arrows shown in FIG. 44.

The heating rolls 602 and 603 are supported by supporting members 610 and 611 having springs 608 and 609, respectively, and are arranged such that the distance between the rolls can be varied optionally.

The cleaning roll 604 is provided with its own driving means and adapted to be driven at a speed different from those of the heating rolls 602 and 603 and in a direction the same as the direction of rotation of, for example, the heating roll 603, as shown in FIG. 44.

The cleaning roll displacing means 605 comprises a support 612 for the cleaning roll 604 and a hydraulic cylinder 607 operative to displace the support 612 to move the cleaning roll 604 into sliding contact with the surfaces of the heating rolls 602 and 603. The heating roll cleaning device 601 is operative in a manner to be described hereunder.

An amount of the plastic resin is fed to the nip between the pair of heating rolls 602 and 603. Then, the heating rolls 602 and 603 are driven in the directions indicated by the arrows shown in FIG. 44 in such a manner as to drag the plastic resin, so that the heating rolls 602 and 603 cooperate together to make a kneaded product. As a result of the operation of both heating rolls 602 and 603, melted or partly melted plastic resin is adhered to the heating rolls 602 and 603, which may become dirty.

Such heating rolls 602 and 603 are so positioned by the supporting members 610 and 611 that the distance between the heating rolls is of the order of several cm. With the heating rolls held in this position, the hydraulic cylinder 607 of the cleaning roll displacing means 605 displaces the cleaning roll 604 and the scraper 606 via the support 612 toward the heating rolls 602 and 603 until the cleaning roll 604 is brought into sliding engagement with the surfaces of both heating rolls 602 and 603. At this time, the heating rolls 602 and 603 and the cleaning roll 604 are so set as to be rotated in the directions indicated by arrows shown in FIG. 44 and at different speeds.

Accordingly, the cleaning roll 604 positively wipes away from the surfaces of the heating rolls 602 and 603 the plastic resin which has been adhered thereto. As a result of the operation of the cleaning roll 604, the surface of the cleaning roll 604 is spoiled by the plastic resin wiped from the heating rolls 602 and 603. This plastic resin, however, is scraped away from the surface of the cleaning roll 606.

As a result, the surfaces of the heating rolls 602 and 603 can be reliably and automatically cleaned to improve the rate of the operation of the heating rolls.

The described heating roll cleaning device 601, moreover, can eliminate the necessity for manual cleaning operation and thus insures safety of the operator.

Another embodiment of the present invention will now be described with reference to FIG. 45.

Figure 45:
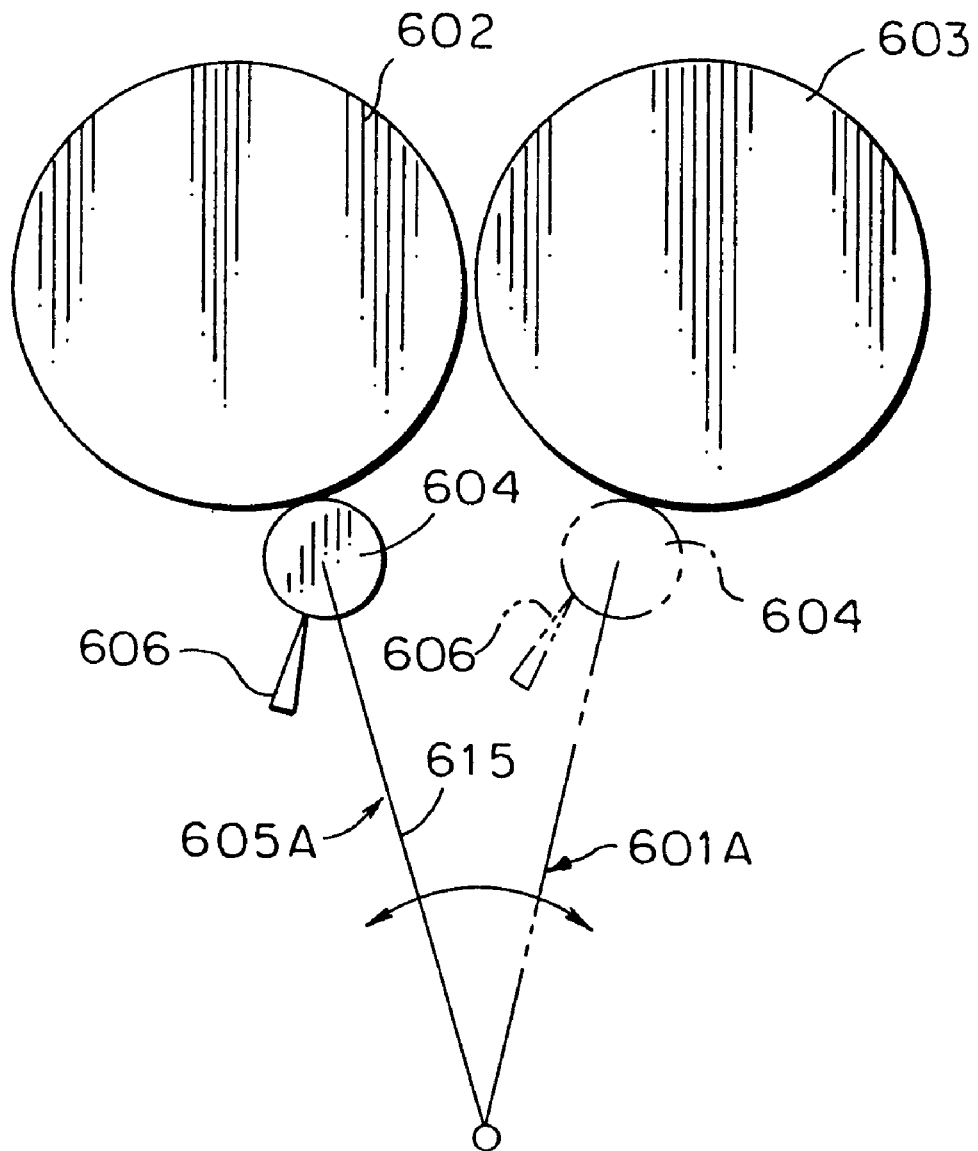
FIG. 45 is a schematic illustration of an arrangement of an apparatus of another embodiment of the present invention.

A heating roll cleaning device 601A shown in FIG. 45 is characterized in that a cleaning roll displacing means 605A is employed which comprises a rotating support 615 used in place of the aforementioned hydraulic cylinder 607 and the support 612 for supporting the cleaning roll 604 and the scraper 606 and a rotary driving mechanism, not shown, for driving the rotating support 615 in directions indicated by arrows shown in FIG. 45.

According to this heating roll cleaning device 601A, the cleaning roll displacing means 605A is operative to move the cleaning roll 604 into sliding engagement with the surface of either one of the heating rolls 602 and 603.

Accordingly, the cleaning roll 604 is rotated to wipe from the surface of the heating roll 602 or 603 the plastic resin which has been adhered thereto. As a result of such wiping operation of the cleaning roll 604, the surface of the cleaning roll 604 is spoiled by the plastic resin wiped away from the heating roll 602 or 603. However, the scraper 606 removes the dirt from the surface of the cleaning roll 604.

As a result, the surfaces of both heating rolls 602 and 603 can be cleaned selectively, reliably and automatically to improve the rate of operation of the heating rolls 602 and 603 and the safety as well.

The present invention is not limited to the described embodiments and various modifications can be made within the gist of the invention.

For example, the cleaning roll displacing means 605 may be of a structure which utilizes an electromagnetic plunger and a spring rather than the hydraulic cylinder 612.

As the present invention is structured as described above, the invention can provide a first heating roll cleaning device which is automatically and reliably operative to clean a pair of heating rolls adhered by plastic resin and which can realize improvement in the rate of operation of the pair of heating rolls and assurance of safe operation.

In addition, because the present invention is structured as described above, the invention can provide a second heating roll cleaning device which is operative to selectively, automatically and reliably clean a pair of heating rolls adhered by plastic resin and which can provide advantages similar to those pointed out above.

Figure 46:
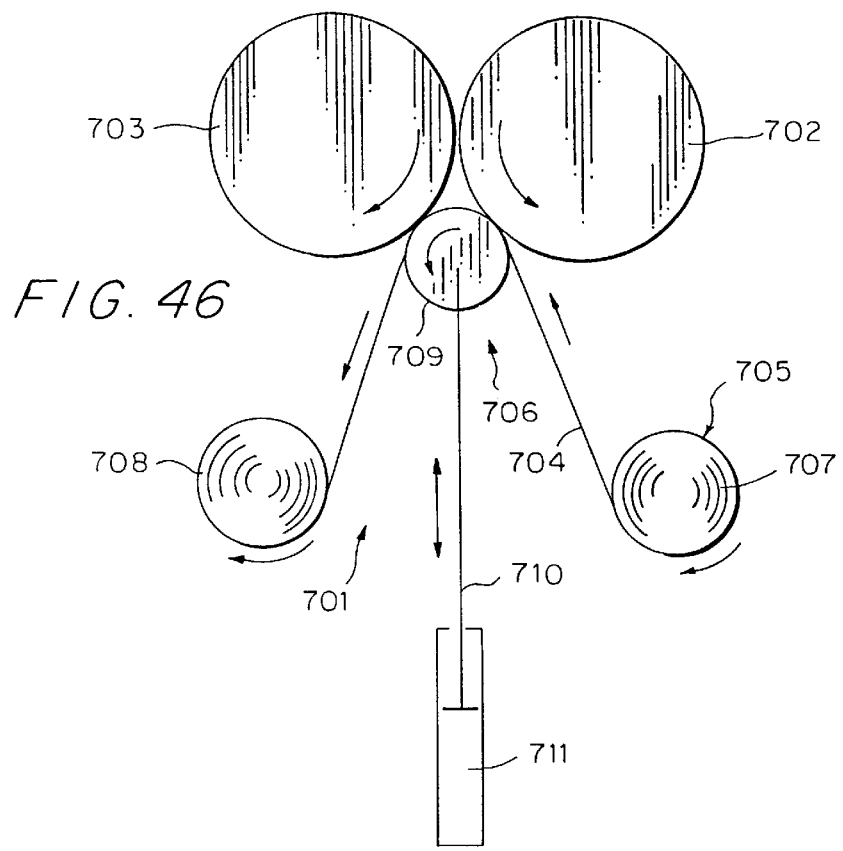
FIG. 46 is a schematic illustration of the operation of the apparatus of the other embodiment of the invention.

A heating roll cleaning device 701 shown in FIG. 46 is disposed under a pair of heating rolls 702 and 703 arranged in parallel relationship with a gap of the order of 0.2 mm defined therebetween to knead plastic resin and make kneaded product.

The heating roll cleaning device 701 comprises a cleaning member feeding means 705 for feeding, transporting and taking up elongated cloth-like cleaning member 704 operative to clean the surfaces of the pair of heating rolls 702 and 703 and a cleaning member contacting means 706 operative to bring into sliding contact with the heating rolls 702 and 703 the cleaning member 704 in its way in the feeding path of the cleaning member feeding means 705.

The cleaning member 704 is made of a material impregnated with organic solvent and selected from a group consisting of fabric (woven fabric, knitted fabric, non-woven fabric or the like), leather sheet, or synthetic leather and the like material, the cleaning member being elongated and having a width corresponding to the length of each of the heating rolls 702 and 703.

The cleaning member feeding means 704 comprises a feeding roll 707 disposed beneath the heating roll 702 and driven by a driver, not shown, to feed and transport the cleaning member 704, and a take-up roll 708 disposed beneath the heating roll 703 and driven by a driver, not shown, to take up the cleaning member 704 fed from the feeding roll 707.

The cleaning member contacting means 706 comprises a feeding roll 709 disposed in the path of transportation of the cleaning member 704 between the feeding roll 707 and the take-up roll 708, a support 710 rotatably supporting the feeding roll 709, and a hydraulic cylinder 711 operative to move the support 710 toward the heating rolls 702 and 703 to cause the feeding roll 709 to urge the cleaning member 704 engaged therewith against both heating roll 702 and 703.

The heating rolls 702 and 703 are adapted to be independently driven by different driving sources and rotated at different speeds and in directions indicated by arrows shown in FIG. 46.

The feeding roll 709 has its own driving source operative to drive the feeding roll at a speed different from those of the heating rolls 702 and 703 to feed the cleaning member 704 toward the take-up roll 708, as shown in FIG. 46.

Now, the operation of the heating roll cleaning device 701 is described hereunder.

An amount of plastic resin is fed to a gap between the pair of heating rolls 702 and 703 and the heating rolls are driven in the directions indicated by arrows shown in FIG. 46 so as to drag the plastic resin, so that the heating rolls 702 and 703 cooperate together to make kneaded product. As a result of such operation of the heating rolls, melted or partly melted plastic resin is adhered to respective heating rolls 702 and 703.

The hydraulic cylinder 711 of the cleaning member contacting means 706 is operated to move, via the support 710 and the feeding roll 709 (driven at a speed different from those of the heating rolls 702 and 703), the cleaning member 704, which lies in the path of feed from the feeding roll 707 of the cleaning member feeding means 705, to be moved into sliding engagement with the heating rolls 702 and 703.

Accordingly, the cleaning member 704 is fed and transported while the cleaning member wipes away from the surfaces of the heating rolls 702 and 703 the plastic resin which has been adhered thereto. The feeding of the cleaning member 704 and the taking-up operation of the take-up roll 708 are continued to assure that a fresh part of the cleaning member 704 is always brought into sliding engagement with the surfaces of the heating rolls 702 and 703. As a result, the surfaces of the heating rolls 702 and 703 can be reliably and automatically cleaned, whereby the rate of operation of the heating rolls 702 and 703 can be improved.

The heating roll cleaning device 701 can eliminate the requirement for manual cleaning operation, which was required in the past, as well as assure the safety of operators.

Another embodiment of the present invention will be described with reference to FIG. 47.

Figure 47:
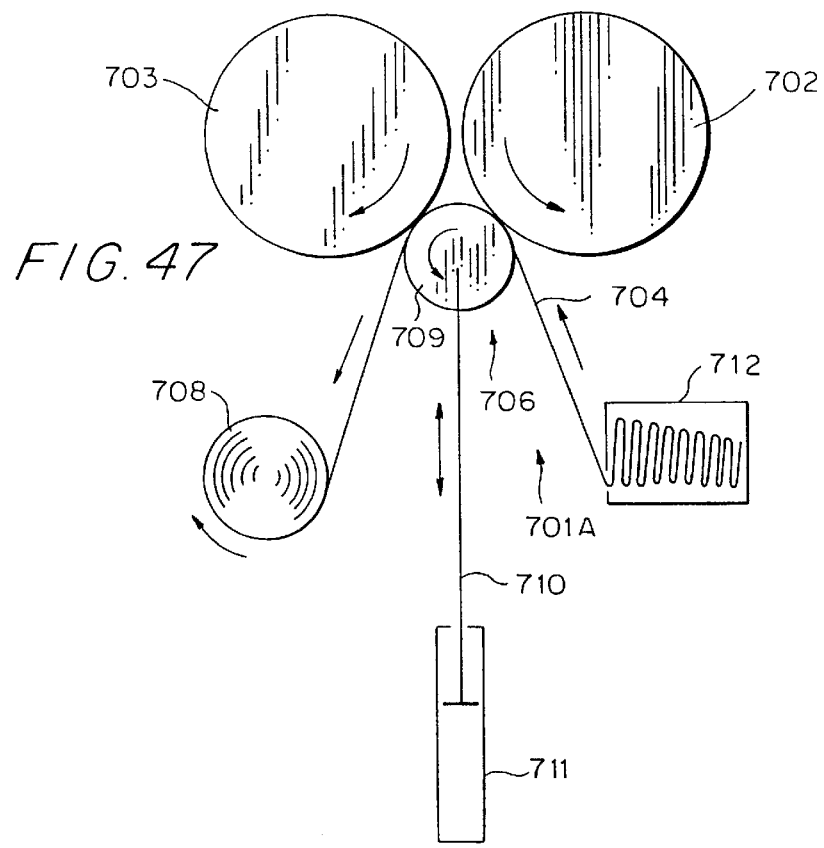
FIG. 47 is a schematic illustration of an arrangement of the apparatus of another embodiment of the present invention.

A heating roll cleaning device 701A shown in FIG. 47 is characterized in that a box-like feeding cassette 712 accommodating the cleaning member 704 in folded state is employed in place of the aforementioned feeding roll 707.

In this heating roll cleaning device 701A, the feeding roll 709 and the take-up roll 708 are driven in the direction indicated by arrows so that the cleaning member 704 from the cassette 712 is fed and transported, as in the above-described heating roll cleaning device 701, to wipe from the heating rolls 702 and 703 the plastic resin which has been adhered thereto. Thus, the heating roll cleaning device 701A also provides advantages as in the described embodiment.

The present invention is not limited to the described embodiments and various modifications may be made within the gist of the invention.

For example, the cleaning member contacting means 706 may be of a structure that utilizes an electromagnetic plunger and a spring in place of the hydraulic cylinder 711.

The cleaning member 704 is not limited to the described fabric and so on and may alternatively comprise an elongated brush having bristles provided on a surface thereof.

A further preferred embodiment of the present invention will be described with reference to FIG. 48 which is a schematic perspective view of another embodiment of the sheet testing sample making apparatus of the present invention.

As shown in FIG. 48, the sheet testing sample making apparatus incorporates a kneading apparatus.

As will be seen in FIG. 48, the kneading apparatus is assembled with a pair of left and right symmetrical side frames 801 and 802 which rotatably support a pair of parallel kneading rolls 811 and 812 extending therebetween. The kneading rolls 811 and 812 are arranged in opposed and closely spaced relationship to define therebetween a valley. The kneading rolls 811 and 812 are drivingly connected to independent driving motors. The bearings which support the shaft of the kneading roll 811 are disposed fixedly in the side frames 801 and 802, whereas members supporting the shaft of the other kneading roll 812 are threadably engaged with screw rods connected to motors 813a and 813b so that the rotations of the motors 813a and 813b cause a translational movement of the kneading roll 812 toward and away from the kneading roll 811. The screw rods have mounted thereon indicators 814a and 814b which indicate the spacing between the two kneading rolls 811 and 812. The kneading rolls 811 and 812 accommodate high frequency induction coils (not shown) connected to an electrical power source so that the rolls are heated by the coils.

The kneading roll 811 shown in FIG. 48 corresponds to the sheet winding roll 6a shown in FIG. 1, the sheet winding roll 46 shown in FIG. 16, the heating roll 201 shown in FIGS. 20, 23 and 24 on which the resin is wound to form a rolled sheet, the sheet winding roll 302 shown in FIG. 25, the heating roll 401 shown in FIGS. 33 and 34 on which the resin is wound to form a rolled sheet, the heating roll 437 shown in FIG. 36 on which the resin is wound to form a rolled sheet, the heating roll 503 shown in FIG. 37 on which the resin is wound to form a rolled sheet, the heating roll 602 shown in FIGS. 43–45 on which the resin is wound to form a rolled sheet, and the heating roll 702 shown in FIG. 46 on which the resin is wound to form a rolled sheet.

Moreover, the kneading roll 812 shown in FIG. 48 corresponds to the heating roll 6 on which no resin is wound, the counter roll 47 shown in FIG. 16, the heating roll 201 shown in FIGS. 20, 23 and 24 on which no resin is wound, the counter roll 303 shown in FIG. 25, the heating roll 401 shown in FIGS. 33 and 34 on which no resin is wound, the heating roll 438 shown in FIG. 36 on which no resin is wound, the heating roll 503a shown in FIG. 37, the heating roll 603 shown in FIGS. 43–45 on which no resin is wound, and the heating roll 703 shown in FIG. 46 on which no resin is wound.

A pair of blades 815a and 815b are operative to limit the spread of the resin to be kneaded by the kneading rolls 811 and 812 such that the distance between the blades 815a and 815b substantially determines the effective widths or lengths of the kneading rolls 811 and 812. The blades 815a and 815b are slidably mounted on a guide rod 809 and respectively threadably engaged with screw rods 823a and 823b which are drivingly connected to pulse motors 816a and 816b so that the rotations of the pulse motors 816a and 816b move the blades 815a and 815b toward and away from each other to vary the effective distance therebetween.

In place of these blades 815a and 815b, the kneading apparatus may alternatively employ the blades 304 shown in FIGS. 25–29.

This apparatus shown in FIG. 48 is provided with a fall returning device which is disposed behind the members shown in FIG. 48 and thus is not shown in this figure.

The fall returning device has the structure shown in FIG. 35 and described hereinbefore and, thus, is not described in more detail hereunder. The heating rolls 437 and 438 shown in FIG. 35 correspond to the kneading rolls 811 and 812 shown in FIG. 48.

The sheet testing sample making apparatus shown in FIG. 48 is provided with a heating roll cleaning device comprising a cleaning roll 822 disposed beneath the kneading rolls 811 and 812 and connected to a pneumatic cylinder 821 so as to be movable thereby into contact with the kneading rolls 811 and 812 and away therefrom.

The heating roll cleaning device comprising the pneumatic cylinder 821 and the cleaning roll 822 both shown in FIG. 48 provides a function similar to that of the heating roll cleaning roll 601 shown in FIG. 43 and, therefore, can be replaced therewith. Similarly, the heating roll cleaning device shown in FIG. 48 may also be replaced by the heating roll cleaning device shown in any of FIGS. 44–47.

It is added that the cleaning roll 822 shown in FIG. 48 and the cleaning roll 604 shown in FIG. 43 are both cylindrical members having axes respectively parallel to the axes of the kneading rolls 811 and 812 and the axes of the kneading rolls 602 and 603 and have rows of brushes mounted thereon so as to extend spirally around the peripheral surfaces of the cylindrical surfaces of the cleaning rolls.

In addition to the above-described kneading apparatus and the fall returning device, the sheet testing sample making apparatus shown in FIG. 48 has a frame feeding device 842.

The frame feeding device 842 is essentially of the structure shown in FIGS. 16 and 17. The frame feeding device 842 shown in FIG. 48 is slightly distinguished from the structure shown in FIGS. 16 and 17 in that a housing 841 corresponding to the housing 41 shown in FIG. 16 is mounted on the frames 801 and 802 via a bracket 844. Because the structure of the frame feeding device 842 is substantially the same as that shown in FIGS. 16 and 17, the description made with reference to FIGS. 16 and 17 will represent a detailed description of the frame feeding device 842.

A frame 840 fed by the frame feeding device 842 shown in FIG. 48 is identical with the frame 30 shown in FIGS. 13–15. Thus, the description of the frame 30 shown in FIGS. 13–15 will represent a description of the frame 840 shown in FIG. 48.

The sheet testing sample making apparatus shown in FIG. 48 further incorporates an automatic sheet thickness detection apparatus 850.

The automatic sheet thickness detection apparatus 850 shown in FIG. 48 has a first surface displacement meter 853 disposed between the blades 815a and 815b, namely, within the effective width of the roll 811, and in contact with the surface of the roll 811 or with a sheet wound thereon, and a second surface displacement meter 854 disposed outside the blades 815a and 815b and in contact with the surface of the roll 811, these meters being connected to a pneumatic cylinder 855 so as to be movable thereby forwardly and backwardly. The first and second surface displacement meters 853 and 854 have measuring tips in the form of rollers which roll on the surface of the roll 811 and/or on the sheet wound thereonto output electrical signals representative of displacements of the centers of the rollers.

The automatic sheet thickness detection apparatus shown in FIG. 48 provides a function equivalent to that of the automatic sheet thickness detection apparatus 101 shown in FIG. 18 and, therefore, may be replaced by the latter sheet thickness detection apparatus 101. In this concern, it is to be noted that the surface displacement member 853 shown in FIG. 48 corresponds to the measuring element 109 and the first gauge 108a shown in FIG. 18, the surface displacement meter 854 shown in FIG. 48 corresponds to the measuring element 109 and the second gauge 108b shown in FIG. 18, and the pneumatic cylinder 855 shown in FIG. 48 is not shown in FIG. 18. The operation of the automatic sheet thickness detection apparatus 850 shown in FIG. 48 may be easily understood by referring to the description of the automatic sheet thickness detection apparatus 101 shown in FIG. 18.

The sheet testing sample making apparatus shown in FIG. 48 may be added with the foreign matter detecting means 5 so that the apparatus acts as an apparatus for automatically detecting fish eyes included in a resin material.

The operation of the above-described sheet testing sample making apparatus shown in FIG. 48 will be described hereunder.

Initially, the high frequency induction coils are electrically energized to heat the kneading rolls 811 and 812 to a predetermined temperature. The motors are actuated and the indicators are read to set the spacing between the kneading rolls 811 and 812 to an initial set value. Then, the motors for the kneading rolls 811 and 812 are started to drive the rolls such that one of the rolls is rotated at a speed higher than that of the other roll.

At this time, the pneumatic cylinder 821 is actuated to keep the cleaning roll 822 spaced away from the kneading rolls 811 and 812. The other pneumatic cylinder 855 is also actuated to keep the surface displacement meters 853 and 854 spaced away from the kneading rolls 811 and 812.

The kneading rolls 811 and 812 are then supplied with an amount of resin compound comprising, for example, a mixture of powdery vinyl chloride, a plasticizer, a stabilizer and a coloring material added as desired. The fall returning device shown in FIG. 35 is operated to return onto the kneading rolls 811 and 812 the resin compound which falls through the gap therebetween.

Due to the rotations of the kneading rolls 811 and 812, the kneading rolls 811 and 812 become to be wound with sheet-like materials.

More specifically, motors are rotated to cause a translational movement of the kneading roll 812 relative to the kneading roll 811 to vary the gap therebetween. In addition, the pulse motors 816a and 816b are rotated to move the pair of blades 815a and 815b toward or away from each other to vary the effective kneading width of the kneading rolls 811 and 812. After the gap between the kneading rolls 811 and 812 and the distance between the blades 815a and 815b have been adjusted to determined values, kneading of the resin compound is performed. At this time, the amount of the rotation of the motors and the amount of the rotation of the pulse motors may be accorded such that the distance between the blades 815a and 815b is decreased or increased with the increase or decrease in the gap between the kneading rolls 811 and 812, respectively, to assure an adequate amount of bank. When the kneading is finished, the motors 813a and 813b are operated to match the space between the kneading rolls 811 and 812 to the thickness of a testing sheet of resin to be made by the apparatus. The pulse motors 816a and 816b are also operated to match the distance between the blades 815a and 815b to the width of the testing resin sheet to be made.

In this state, the rotations of the kneading rolls 811 and 812 are continued and the thickness of the sheet wound on the kneading rolls 811 and 812 is measured by the automatic sheet thickness detection apparatus 850. The operation of the automatic sheet thickness detection apparatus 850 can be understood by referring to the description of the automatic sheet thickness detection apparatus shown in FIG. 18.

When it is confirmed from this measurement that the sheet thickness measured is of a predetermined value, the frame feeding apparatus 842 feeds a frame 840 into the space between the kneading rolls 811 and 812 so that the sheet wound on the kneading rolls 811 and 812 is transferred to the frame 840. The operation which starts with the feeding of the frame 840 and ends with the transfer of the sheet to the frame 840 can be easily understood by referring to the description of the frame feeding apparatus 41 shown in FIGS. 16 and 17.

After the initial test sheet has been made and the sheet has been transferred to the frame to form a sheet testing sample, the sheet testing sample is fed into the foreign matter detecting means 5 shown in FIG. 1 so that the sheet is examined as to whether a foreign matter, such as fish eye, is included in the sheet or not. On the other hand, as a preparation for a succeeding kneading operation, the surfaces of the kneading rolls 811 and 812 are cleaned by the heating roll cleaning device.

The cleaning of the kneading rolls 811 and 812 by the heating roll cleaning device can be easily understood by referring to the description of the heating roll cleaning device 610 shown in FIGS. 43 and 44. The heating rolls 602 and 603 referred to in the description of the heating roll cleaning device 601 shown in FIGS. 43 and 44 correspond to the kneading rolls 811 and 812 shown in FIG. 48 while the cleaning roll 604 shown in FIGS. 43 and 44 corresponds to the cleaning roll 822 shown in FIG. 48.

The examination of the sheet testing sample by the foreign matter detecting means 5 can be easily understood by referring to the previous description of the foreign matter detecting means 5.

In the foreign matter detecting means 5 shown in FIG. 1, the light irradiation means 17 with a light source and the image pick-up means 18 are both fixed. However, this arrangement may be modified such that the light irradiation means 17 and the image pick-up means 18 are disposed on the opposite sides of a table (not shown) on which a sheet testing sample made by the sheet testing sample making apparatus and carried therefrom by a transferring means such as a belt convey or disposed adjacent a sheet testing sample outlet of the apparatus is placed and such that the light irradiation means 17 and the image pick-up means 18 are moved in parallel so that the sheet surface of the sheet testing sample placed on the table can be scanned by the image pick-up means 18 and the light irradiation means 17.

Since the present invention is structured as described in detail hereinabove, the invention provides a heating roll cleaning device which is operative to automatically and reliably clean a pair of heating rolls adhered by plastic resin and can realize improvement in the rate of operation of the pair of heating rolls and assurance of safety operation.

Several embodiments of the invention have been described in detail above. However, the present invention is not limited to the described embodiments and appropriate modifications can be made within the gist of the present invention.

What is claimed is:

1. A kneading apparatus including:

a pair of kneading rolls; and a pair of blades;

said pair of kneading rolls being arranged such that axes of said kneading rolls extend in parallel relationship, said kneading rolls being slightly spaced from each other so that said rolls define therebetween a valley for accumulating an amount of resin supplied thereto from above said valley, said kneading rolls including a movable kneading roll having a shaft and being connected to driving source means through shaft supporting members such that said movable kneading roll is movable toward and away from the other kneading roll to vary a distance between said axes, thereby producing a sheet of resin wound on one of the kneading rolls;

said pair of blades each including a portion so shaped as to extend substantially along said valley and being positioned close to said kneading rolls, said pair of blades being spaced by a predetermined distance from each other and movable in the axial direction of said kneading rolls; and further including a fall returning device including an endless belt below said valley to catch a part of said resin which falls from said valley through a gap between said kneading rolls and to return said part to said valley, said endless belt having a width substantially equal to an effective width of each of said kneading rolls and being movable into and out of contact with one of said kneading rolls;

and wherein said fall returning device further comprises a pair of supporting bases each including a first support so disposed as to face tops of said kneading rolls, a second support so disposed as to face bottoms of said kneading rolls, and a third support interconnecting said first and second supports, said supporting bases being disposed in opposed relationship;

a group of driven rolls comprising at least a first driven roll rotatably disposed between the pair of first supports, a second driven roll rotatably disposed between the pair of said second supports, and a moveably supported third driven roll;

said endless belt extending around the rolls of said group of driven rolls; and base driving means operative to move said supporting bases forwardly and backwardly to bring said endless belt into and out of contact with heating rolls.

2. A kneading apparatus according to claim 1, further including a first blade for scraping a surface of said endless belt engaged with said first driven roll and a second blade disposed adjacent said second driven roll to scrape one of said heating rolls which is not engaged by said endless belt.

3. A kneading apparatus including:

a pair of kneading rolls; and a pair of blades;

said pair of kneading rolls being arranged such that axes of said kneading rolls extend in parallel relationship, said kneading rolls being slightly spaced from each other so that said rolls define therebetween a valley for accumulating an amount of resin supplied thereto from above said valley, said kneading rolls including a movable kneading roll having a shaft and being connected to driving source means through shaft supporting members such that said movable kneading roll is movable toward and away from the other kneading roll to vary a distance between said axes, thereby producing a sheet of resin wound on one of the kneading rolls;

said pair of blades each including a portion so shaped as to extend substantially along said valley and being positioned close to said kneading rolls, said pair of blades being spaced by a predetermined distance from each other and movable in the axial direction of said kneading rolls;

further including a fall returning device including an endless belt below said valley to catch a part of said resin which falls from said valley through a gap between said kneading rolls and to return said part to said valley, said endless belt having a width substantially equal to an effective width of each of said kneading rolls and being movable into and out of contact with one of said kneading rolls;

wherein said fall returning device further includes a first doctor blade operative to scrape resin adhered to a run of said endless belt engaged with a one of said kneading rolls and drop the thus scraped resin onto the one kneading roll, and a second doctor blade engaged with an other of said kneading rolls and operative to scrape resin adhered to the other kneading roll and drop the thus scraped resin onto said endless belt.

4. A kneading apparatus including:

a pair of kneading rolls; and a pair of blades;

said pair of kneading rolls being arranged such that axes of said kneading rolls extend in parallel relationship, said kneading rolls being slightly spaced from each other so that said rolls define therebetween a valley for accumulating an amount of resin supplied thereto from above said valley, said kneading rolls including a movable kneading roll having a shaft and being connected to driving source means through shaft supporting members such that said movable kneading roll is movable toward and away from the other kneading roll to vary a distance between said axes, thereby producing a sheet of resin wound on one of the kneading rolls;

said pair of blades each including a portion so shaped as to extend substantially along said valley and being positioned close to said kneading rolls, said pair of blades being spaced by a predetermined distance from each other and movable in the axial direction of said kneading rolls;

further including a roll cleaning device including a cleaning roll so mounted as to be movable into contact with lower surfaces of said pair of kneading rolls.

* * * * *